(12) United States Patent
Clarke et al.

(10) Patent No.: US 10,669,578 B2
(45) Date of Patent: *Jun. 2, 2020

(54) SAMPLE PREPARATION METHOD

(71) Applicant: Oxford Nanopore Technologies Ltd., Oxford (GB)

(72) Inventors: James Anthony Clarke, Kidlington (GB); Marion Louise Crawford, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/120,186

(22) PCT Filed: Feb. 19, 2015

(86) PCT No.: PCT/GB2015/050483
§ 371 (c)(1),
(2) Date: Aug. 19, 2016

(87) PCT Pub. No.: WO2015/124935
PCT Pub. Date: Aug. 27, 2015

(65) Prior Publication Data
US 2017/0067101 A1 Mar. 9, 2017

(30) Foreign Application Priority Data
Feb. 21, 2014 (GB) .................................. 1403096.9

(51) Int. Cl.
*C12Q 1/6869* (2018.01)

(52) U.S. Cl.
CPC ................................. *C12Q 1/6869* (2013.01)

(58) Field of Classification Search
CPC ......... C12Q 1/6869; C12Q 1/68; C07H 19/20
See application file for complete search history.

(56) References Cited

U.S. PATENT DOCUMENTS

| | | | |
|---|---|---|---|
| 5,215,899 A | 6/1993 | Dattagupta | |
| 5,424,413 A | 6/1995 | Hogan et al. | |
| 5,561,043 A | 10/1996 | Cantor et al. | |
| 5,777,078 A | 7/1998 | Bayley et al. | |
| 5,795,782 A | 8/1998 | Church et al. | |
| 5,817,771 A | 10/1998 | Bayley et al. | |
| 5,866,328 A | 2/1999 | Bensimon et al. | |
| 5,866,336 A | 2/1999 | Nazarenko et al. | |
| 5,985,834 A | 11/1999 | Engel et al. | |
| 6,015,714 A | 1/2000 | Baldarelli et al. | |
| 6,087,099 A | 7/2000 | Gupte et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,627,067 B1 | 9/2003 | Branton et al. | |
| 6,787,308 B2 | 9/2004 | Balasubramanian et al. | |
| 6,824,659 B2 | 11/2004 | Bayley et al. | |
| 6,863,833 B1 | 3/2005 | Bloom et al. | |
| 6,916,665 B2 | 7/2005 | Bayley et al. | |
| 6,927,070 B1 | 8/2005 | Bayley et al. | |
| 7,087,729 B1 | 8/2006 | Prive | |
| 7,189,503 B2 | 3/2007 | Akeson et al. | |
| 7,238,485 B2 | 7/2007 | Akeson et al. | |
| 7,361,466 B2 | 4/2008 | Korlach et al. | |
| 7,507,575 B2 | 3/2009 | Bedingham et al. | |
| 8,105,846 B2 | 1/2012 | Bayley et al. | |
| 8,143,030 B2 | 3/2012 | Maxham et al. | |
| 8,343,746 B2 * | 1/2013 | Rank ...................... | C12P 19/34 435/183 |
| 8,383,369 B2 | 2/2013 | Maxham et al. | |
| 8,628,940 B2 | 1/2014 | Sorenson et al. | |
| 8,652,779 B2 | 2/2014 | Turner et al. | |
| 8,785,211 B2 | 7/2014 | Bayley et al. | |
| 8,822,160 B2 | 9/2014 | Bayley et al. | |
| 8,828,208 B2 | 9/2014 | Canas et al. | |
| 8,889,348 B2 | 11/2014 | Ju | |
| 9,057,102 B2 | 6/2015 | Turner et al. | |
| 9,116,118 B2 | 8/2015 | Turner et al. | |
| 9,127,313 B2 | 9/2015 | Brown et al. | |
| 9,145,623 B2 | 9/2015 | Kavanagh et al. | |
| 9,150,918 B2 | 10/2015 | Turner et al. | |

(Continued)

FOREIGN PATENT DOCUMENTS

| | | |
|---|---|---|
| CN | 101495656 | 7/2009 |
| CN | 102245760 | 11/2011 |

(Continued)

OTHER PUBLICATIONS

[No Author Listed] HyperMu(TM)TransposonTools HyperMu(TM)<CHL-1>InsertionKit. Jan. 1, 2011. Retrieved from http://arb-ls.com/download/epi protocol/search/document/197p10611.pdf on Oct. 8, 2014.
[No Author Listed] Nucleic acid double helix, Wikipedia.com (accessed May 24, 2016).
[No Author Listed] PreCR Repair Mix—Product Information, FAQs, Protocols, Other Tools & Resources, Related Products etc. Jan. 1, 2010. Retrieved from https://www.neb.com/products/m0309-preer-repair-mix on Oct. 8, 2014.
[No Author Listed] Thermo Scientific Mutation Generation System Kit. Technical Manual. 2012.

(Continued)

*Primary Examiner* — Narayan K Bhat
(74) *Attorney, Agent, or Firm* — Wolf, Greenfield & Sacks, P.C.

(57) ABSTRACT

The invention relates to an improved method for characterising a template polynucleotide. The method involves using a polymerase to prepare a modified polynucleotide which makes it easier to characterise than the template polynucleotide.

16 Claims, 21 Drawing Sheets
Specification includes a Sequence Listing.

(56) References Cited

U.S. PATENT DOCUMENTS

| | | | |
|---|---|---|---|
| 9,222,082 B2 | 12/2015 | Jayasinghe et al. | |
| 9,542,527 B2 | 1/2017 | Travers et al. | |
| 9,546,400 B2 | 1/2017 | Turner et al. | |
| 9,551,023 B2 * | 1/2017 | Turner | C12Q 1/6806 |
| 9,556,480 B2 | 1/2017 | Turner et al. | |
| 9,670,526 B2 | 6/2017 | Kokoris et al. | |
| 9,678,056 B2 | 6/2017 | Turner et al. | |
| 9,738,929 B2 | 8/2017 | Turner et al. | |
| 9,957,560 B2 | 5/2018 | Brown et al. | |
| 10,131,944 B2 | 11/2018 | Bernick et al. | |
| 10,221,450 B2 | 3/2019 | Heron et al. | |
| 2002/0028458 A1 | 3/2002 | Lexow | |
| 2002/0094526 A1 | 7/2002 | Bayley et al. | |
| 2002/0098530 A1 | 7/2002 | Pfeifer et al. | |
| 2002/0197618 A1 | 12/2002 | Sampson | |
| 2003/0044816 A1 | 3/2003 | Denison et al. | |
| 2003/0059778 A1 | 3/2003 | Berlin et al. | |
| 2003/0087232 A1 | 5/2003 | Christians et al. | |
| 2003/0099951 A1 | 5/2003 | Akeson et al. | |
| 2003/0108902 A1 | 6/2003 | Abarzua | |
| 2003/0118595 A1 | 6/2003 | Niemeyer et al. | |
| 2003/0165936 A1 | 9/2003 | Rabbani et al. | |
| 2003/0166137 A1 | 9/2003 | Zuker et al. | |
| 2003/0211502 A1 | 11/2003 | Sauer et al. | |
| 2003/0215881 A1 | 11/2003 | Bayley et al. | |
| 2004/0055901 A1 | 3/2004 | Petersen et al. | |
| 2004/0214177 A1 | 10/2004 | Bension | |
| 2004/0229315 A1 | 11/2004 | Lee et al. | |
| 2005/0053961 A1 | 3/2005 | Akeson et al. | |
| 2005/0142559 A1 | 6/2005 | Makrigiorgos | |
| 2005/0221316 A1 | 10/2005 | Pedersen et al. | |
| 2005/0227239 A1 | 10/2005 | Joyce | |
| 2005/0260655 A1 | 11/2005 | Liu et al. | |
| 2006/0063171 A1 | 3/2006 | Akeson et al. | |
| 2006/0086626 A1 | 4/2006 | Joyce | |
| 2006/0141516 A1 | 6/2006 | Kobold et al. | |
| 2006/0292611 A1 | 12/2006 | Berka et al. | |
| 2007/0015182 A1 | 1/2007 | Abarzua | |
| 2007/0031857 A1 | 2/2007 | Makarov et al. | |
| 2007/0122885 A1 | 5/2007 | Reeves et al. | |
| 2007/0224613 A1 | 9/2007 | Strathmann | |
| 2008/0166724 A1 | 7/2008 | Gerber et al. | |
| 2008/0206252 A1 | 8/2008 | Pennica et al. | |
| 2008/0311582 A1 | 12/2008 | Bayley et al. | |
| 2009/0167288 A1 | 7/2009 | Reid et al. | |
| 2009/0256116 A1 | 10/2009 | Shumaker-Parry et al. | |
| 2009/0280538 A1 | 11/2009 | Patel et al. | |
| 2009/0298075 A1 | 12/2009 | Travers et al. | |
| 2010/0003560 A1 | 1/2010 | Shibata | |
| 2010/0035260 A1 | 2/2010 | Olasagasti et al. | |
| 2010/0075309 A1 | 3/2010 | Maxham et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2010/0276588 A1 | 11/2010 | Syms | |
| 2010/0331194 A1 | 12/2010 | Turner et al. | |
| 2011/0019186 A1 | 1/2011 | Himmelhaus et al. | |
| 2011/0136676 A1 | 6/2011 | Greene | |
| 2011/0177498 A1 | 7/2011 | Clarke et al. | |
| 2011/0214991 A1 | 9/2011 | Kim et al. | |
| 2011/0224106 A1 | 9/2011 | Eshoo et al. | |
| 2011/0229877 A1 | 9/2011 | Jayasinghe et al. | |
| 2011/0281768 A1 | 11/2011 | Travers et al. | |
| 2011/0311965 A1 | 12/2011 | Maglia et al. | |
| 2012/0010085 A1 | 1/2012 | Rava et al. | |
| 2012/0058468 A1 | 3/2012 | Mckeown | |
| 2012/0064599 A1 | 3/2012 | Jayasinghe et al. | |
| 2012/0100530 A1 | 4/2012 | Moysey et al. | |
| 2012/0107802 A1 | 5/2012 | Stoddart et al. | |
| 2013/0017978 A1 | 1/2013 | Kavanagh et al. | |
| 2013/0078624 A1 | 3/2013 | Holmes et al. | |
| 2013/0143802 A1 | 6/2013 | Chilkoti | |
| 2013/0195908 A1 | 8/2013 | Leonetti et al. | |
| 2013/0327644 A1 | 12/2013 | Turner et al. | |
| 2014/0051069 A1 | 2/2014 | Jayasinghe et al. | |
| 2014/0134618 A1 | 5/2014 | Kokoris et al. | |
| 2014/0134629 A1 | 5/2014 | Turner et al. | |
| 2014/0206842 A1 | 7/2014 | Majeed et al. | |
| 2014/0255921 A1 | 9/2014 | Moysey et al. | |
| 2014/0262784 A1 | 9/2014 | Clarke et al. | |
| 2014/0296089 A1 | 10/2014 | Holmes et al. | |
| 2014/0308661 A1 | 10/2014 | Holmes et al. | |
| 2014/0335512 A1 | 11/2014 | Moysey et al. | |
| 2015/0008126 A1 | 1/2015 | Maglia et al. | |
| 2015/0045257 A1 | 2/2015 | Kavanagh et al. | |
| 2015/0065354 A1 | 3/2015 | Moysey et al. | |
| 2015/0152492 A1 | 6/2015 | Brown et al. | |
| 2015/0167075 A1 | 6/2015 | Turner et al. | |
| 2015/0175663 A1 | 6/2015 | Yokoi et al. | |
| 2015/0191709 A1 | 7/2015 | Heron et al. | |
| 2015/0197796 A1 | 7/2015 | White et al. | |
| 2015/0218629 A1 | 8/2015 | Heron et al. | |
| 2015/0265994 A1 | 9/2015 | Hyde et al. | |
| 2015/0285781 A1 | 10/2015 | Heron et al. | |
| 2015/0307934 A1 | 10/2015 | Turner et al. | |
| 2016/0010147 A1 | 1/2016 | Heron et al. | |
| 2016/0010148 A1 | 1/2016 | Turner et al. | |
| 2016/0011169 A1 | 1/2016 | Turner et al. | |
| 2016/0076092 A1 | 3/2016 | Jayasinghe et al. | |
| 2016/0194677 A1 | 7/2016 | Stoddart et al. | |
| 2016/0257942 A1 | 9/2016 | Bruce et al. | |
| 2016/0281159 A1 | 9/2016 | Brown et al. | |
| 2016/0362739 A1 | 12/2016 | Brown et al. | |
| 2017/0002406 A1 | 1/2017 | Bowen et al. | |
| 2017/0240955 A1 | 8/2017 | White | |
| 2017/0314062 A1 | 11/2017 | Kokoris et al. | |
| 2017/0321266 A1 | 11/2017 | Mckeown | |
| 2018/0291440 A1 | 10/2018 | McKeown | |
| 2018/0291441 A1 | 10/2018 | Brown et al. | |
| 2019/0194722 A1 | 6/2019 | Stoddart et al. | |
| 2019/0211390 A1 | 7/2019 | Heron et al. | |

FOREIGN PATENT DOCUMENTS

| | | |
|---|---|---|
| EP | 2682460 A1 | 1/2014 |
| GB | 2130219 | 5/1984 |
| GB | 2237390 | 5/1991 |
| GB | 2453377 | 4/2009 |
| JP | H11-137260 | 5/1999 |
| JP | 2012-506704 A | 3/2012 |
| WO | WO 1994/023065 | 10/1994 |
| WO | WO 1999/005167 | 2/1999 |
| WO | WO 2000/028312 | 5/2000 |
| WO | WO 2001/040516 | 6/2001 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2005/056750 | 6/2005 |
| WO | WO 2005/118877 | 12/2005 |
| WO | WO 2005/124888 | 12/2005 |
| WO | WO 2006/020775 | 2/2006 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/146158 | 12/2007 |
| WO | WO 2008/045575 | 4/2008 |
| WO | WO 2008/083554 | 7/2008 |
| WO | WO 2008/102120 | 8/2008 |
| WO | WO 2008/102121 | 8/2008 |
| WO | WO 2008/124107 | 10/2008 |
| WO | WO 2009/035647 | 3/2009 |
| WO | WO 2009/044170 A1 | 4/2009 |
| WO | WO 2009/077734 A2 | 6/2009 |
| WO | WO 2010/004265 | 1/2010 |
| WO | WO 2010/004273 | 1/2010 |
| WO | WO 2010/034018 | 3/2010 |
| WO | WO 2010/048605 A1 | 4/2010 |
| WO | WO 2010/051773 | 5/2010 |
| WO | WO 2010/086602 A1 | 8/2010 |
| WO | WO 2010/086603 | 8/2010 |
| WO | WO 2010/086622 | 8/2010 |

(56) References Cited

FOREIGN PATENT DOCUMENTS

| WO | WO 2010/094040 |   | 8/2010 |
|---|---|---|---|
| WO | WO 2010/109107 | A1 | 9/2010 |
| WO | WO 2010/109197 |   | 9/2010 |
| WO | WO 2010/122293 |   | 10/2010 |
| WO | WO 2011/067559 |   | 6/2011 |
| WO | WO 2012/033524 | A2 | 3/2012 |
| WO | WO 2012/061832 |   | 5/2012 |
| WO | WO 2012/083249 | A2 | 6/2012 |
| WO | WO 2012/098561 | A2 | 7/2012 |
| WO | WO 2012/098562 | A2 | 7/2012 |
| WO | WO 2012/103545 | A1 | 8/2012 |
| WO | WO 2012/107778 | A2 | 8/2012 |
| WO | WO 2012/164270 | A1 | 12/2012 |
| WO | WO 2013/014451 | * | 1/2013 |
| WO | WO 2013/014451 | A1 | 1/2013 |
| WO | WO 2013/041878 | A1 | 3/2013 |
| WO | WO 2013/057495 | A2 | 4/2013 |
| WO | WO 2013/098561 | A2 | 7/2013 |
| WO | WO 2013/098562 | A2 | 7/2013 |
| WO | WO 2013/131962 | A1 | 9/2013 |
| WO | WO 2013/153359 | A1 | 10/2013 |
| WO | WO 2013/185137 | A1 | 12/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/108810 | A2 | 7/2014 |
| WO | WO 2014/135838 | A1 | 9/2014 |
| WO | WO 2014/153408 |   | 9/2014 |
| WO | WO 2015/022544 | A1 | 2/2015 |
| WO | WO 2015/031909 | A1 | 3/2015 |
| WO | WO 2015/055981 | A2 | 4/2015 |
| WO | WO 2015/056028 | A1 | 4/2015 |
| WO | WO 2015/110777 | A1 | 7/2015 |
| WO | WO 2015/110813 | A1 | 7/2015 |
| WO | WO 2015/189636 | A1 | 12/2015 |
| WO | WO 2015/200609 | A1 | 12/2015 |
| WO | WO 2016/003814 | A1 | 1/2016 |
| WO | WO 2016/059363 | A1 | 4/2016 |

OTHER PUBLICATIONS

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Alzbutas et al., MuA Transposase enzyme enables fast and easy DNA library preparation for next generation sequencing. Thermo Fisher Scientific. Jan. 1, 2012. Retrieved from URL:http://www.gene-quantification.de/qper-ngs-2013/posters/P013-qPCR-NGS-2013.pdf on May 18, 2017.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrameas et al., Coupling of enzymes to proteins with glutaraldehyde. Use of the conjugates for the detection of antigens and antibodies. Immunochemistry. Jan. 1996;6(1):43-52.

Baker, De novo genome assembly: what every biologist should know. Nature methods. Apr. 2012;9(4):333-337.

Bayley et al., Stochastic sensors inspired by biology. Nature. Sep. 13, 2001;413(6852):226-30.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bowie et al., Deciphering the message in protein sequences: tolerance to amino acid substitutions. Science. Mar. 16, 1990;247(4948):1306-10.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

(56) References Cited

OTHER PUBLICATIONS

Cheley et al., Spontaneous oligomerization of a staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Coros et al., Effect of mutations in the Mu-host junction region on transpososome assembly. J Mol Biol. Jul. 6, 2001;310(2):299-309.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Deamer et al., Three decades of nanopore sequencing. Nat Biotechnol. May 6, 2016;34(5):51824. doi: 10.1038/nbt.3423.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Eoff et al., Chemically modified DNA substrates implicate the importance of electrostatic interactions for DNA unwinding by Dda helicase. Biochemistry. Jan. 18, 2005;44(2):666-74.

Erie et al., A dumbbell-shaped, double-hairpin structure of DNA: a thermodynamic investigation. Biochemistry. Nov. 3, 1987;26(22):7150-9.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Flicek et al., Sense from sequence reads: methods for alignment and assembly. Nat Methods. Nov. 2009;6(11 Suppl):S6-S12. doi: 10.1038/nmeth.1376.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fu et al., Selective bypass of a lagging strand roadblock by the eukaryotic replicative DNA helicase. Cell. Sep. 16, 2011;146(6):931-41. doi:10.1016/j.cell.2011.07.045.
Garcillán-Barcia et al., The diversity of conjugative relaxases and its application in plasmid classification. FEMS Microbiol Rev. May 2009;33(3):657-87.
GenPept Accession No. XP 003728286. Jun. 7, 2012.
Genschel et al., Interaction of E. coli single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Green et al., Quantitative evaluation of the lengths of homobifunctional protein cross-linking reagents used as molecular rulers. Protein Sci. Jul. 2001;10(7):1293-304.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Gui-Jiang et al., Advances in next-generation sequencing technologies. Progress in Modern Biomedicine. 2012;12(19):3789-3793.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.

(56) References Cited

OTHER PUBLICATIONS

Haque et al., Solid-State and Biological Nanopore for Real-Time Sensing of Single Chemical and Sequencing of DNA. Nano Today. Feb. 2013;8(1):56-74.
Heger, Nanopore Sequencing Makes Strides in 2010 as Technology Improves, Investment Grows. GenomeWeb. Jan. 11, 2011. Retrieved from https://www.genomeweb.com/sequencing/nanopore-sequencing-makes-strides-2010-technology-improves-investment-grows on Oct. 4, 2017.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6. 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Ivanov et al., DNA tunneling detector embedded in a nanopore. Nano Lett. Jan. 12, 2011;11(1):279-85. doi: 10.1021/nl103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, 2005;97:104317:1-7.
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Kozlov et al., Regulation of single-stranded DNA binding by the C termini of Escherichia coli single-stranded DNA-binding (SSB) protein. J Biol Chem. May 28, 2010;285(22):17246-52. doi: 10.1074/jbc.M110.118273. Epub Apr. 1, 2010.
Kumar et al., Nonradioactive labeling of synthetic oligonucleotide probes with terminal deoxynucleotidyl transferase. Anal Biochem. Mar. 1998;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Lee et al., Importance of the conserved CA dinucleotide at Mu termini. J Mol Biol. Nov. 30, 2001;314(3):433-44.
Li et al., DNA molecules and configurations in a solid-state nanopore microscope. Nat Mater. Sep. 2003;2(9):611-5. Epub Aug. 24, 2003.
Li et al., DNA Sequencing Method Based on Electro-Mechanical Effects Between DNA and Nano-Structures. Advances in Mechanics. Nov. 25, 2011;41(6):722-729.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Lodish et al., Molecular Cell Biology. Fourth Edition. New York: W.H. Freeman; 2000. Section 4.1, Structure of Nucleic Acids, pp. 101-110.
Lohman et al., Mechanisms of helicase-catalyzed DNA unwinding. Annu Rev Biochem. 1996;65:169-214.
Lohman et al., Non-hexameric DNA helicases and translocases:mechanisms and regulation. Nat Rev Mol Cell Biol. May 2008;9(5):391-401. doi:10.1038/nrm2394.
Lovett et al., Identification and purification of a single-stranded-DNA-specific exonuclease encoded by the recJ gene of Escherichia coli. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Ma et al., Bright functional rotaxanes. Chem Soc Rev. Jan. 2010;39(1):70-80. doi: 10.1039/b901710k. Epub Jul. 21, 2009.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Martin et al., Nanoscale protein pores modified with PAMAM dendrimers. J Am Chem Soc. Aug. 8, 2007;129(31):9640-9. Epub Jul. 18, 2007.
Martinez et al., The mRNA cap structure stimulates rate of poly(A) removal and amplifies processivity of degradation. J Biol Chem. Jul. 27, 2001;276(30):27923-9. Epub May 18, 2001.

(56) References Cited

OTHER PUBLICATIONS

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.

Mitchell et al., Chemical tags facilitate the sensing of individual DNA strands with nanopores. Angew Chem Int Ed Engl. 2008;47(30):5565-8. doi:10.1002/anie.200800183.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Mol et al., Structure and function of the multifunctional DNA-repair enzyme exonuclease III. Nature. Mar. 23, 1995;374(6520):381-6.

Montal et al., Formation of bimolecular membranes from lipid monolayers and a study of their electrical properties. Proc Natl Acad Sci U S A. Dec. 1972;69(12):3561-6.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365-R1393 (2003).

Niemeyer et al., DNA-directed assembly of bienzymic complexes from in vivo biotinylated NAD(P)H:FMN oxidoreductase and luciferase. Chembiochem. Mar. 1, 2002;3(2-3):242-5.

Nikolov et al., Behavior of giant vesicles with anchored DNA molecules. Biophys J. Jun. 15, 2007;92(12):4356-68. Epub Mar. 23, 2007.

Nwe et al., Growing applications of "click chemistry" for bioconjugation in contemporary biomedical research. Cancer Biother Radiopharm. Jun. 2009;24(3):289-302. doi: 10.1089/cbr.2008.0626.

O'Shea et al., X-ray structure of the GCN4 leucine zipper, a two-stranded, parallel coiled coil. Science. Oct. 25, 1991;254(5031):539-44.

Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.

Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.

Pfeiffer et al., Bivalent cholesterol-based coupling of oligonucletides to lipid membrane assemblies. J Am Chem Soc. Aug. 25, 2004;126(33):10224-5.

Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Press release: Oxford Nanopore introduces DNA 'strand sequencing' on the high-throughput GridION platform and presents MinION, a sequencer the size of a USB; memory stick, Feb. 2012.

Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.

Remaut et al., Protein-protein interaction through beta-strand addition. Trends Biochem Sci. Aug. 2006;31(8):436-44. Epub Jul. 7, 2006.

Richards et al., Structure of the DNA repair helicase he1308 reveals DNA binding and autoinhibitory domains. J Biol Chem. Feb. 22, 2008;283(8):5118-26. Epub Dec. 4, 2007.

Saariaho et al., Characteristics of MuA transposase-catalyzed processing of model transposon end DNA hairpin substrates. Nucleic Acids Res. Jun. 6, 2006;34(10):3139-49. Print 2006.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.

Sauer-Budge et al., Unzipping kinetics of double-stranded DNA in a nanopore. Phys Rev Lett. Jun. 13, 2003;90(23):238101. Epub Jun. 9, 2003.

Savilahti et al., The phage Mu transpososome core: DNA requirements for assembly and function. Embo J. Oct. 2, 1995;14(19):4893-903.

Schneider et al., DNA sequencing with nanopores. Nat Biotechnol. Apr. 10, 2012;30(4):326-8. doi: 10.1038/nbt.2181.

Seeman, Nucleic acid junctions and lattices. J Theor Biol. Nov. 21, 1982;99(2):237-47.

Seo et al., Click chemistry to construct fluorescent oligonucleotides for DNA sequencing. J Org Chem. Jan. 24, 2003;68(2):609-12.

Seol et al., Stretching of homopolymeric RNA reveals single-stranded helices and base-stacking. Phys Rev Lett. Apr. 13, 2007;98(15):158103. Epub Apr. 12, 2007.

Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.

Shin et al., Kinetics of a reversible covalent-bond-forming reaction observed at the single-molecule level. Angew Chem Int Ed Engl. Oct. 4, 2002;41(19):3707-9; 3523.

Smeets et al., Salt dependence of ion transport and DNA translocation through solid-state nanopores. Nano Lett. Jan. 2006;6(1):89-95.

Song et al., Structure of staphylococcal alpha-hemolysin, a heptameric transmembrane pore. Science. Dec. 13, 1996;274(5294):1859-66.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad

(56) References Cited

OTHER PUBLICATIONS

Sci U S A. May 12, 2009;106(19):7702-7. doi: 10.1073/pnas. 0901054106. Epub Apr. 20, 2009.

Suhasini et al., Mechanistic and biological aspects of helicase action on damaged DNA. Cell Cycle. Jun. 15, 2010;9(12):2317-29. Epub Jun. 15, 2010.

Sutherland et al., An analysis of mismatched duplex DNA unzipping through a bacterial nanopore. Biochem Cell Biol. Jun. 2004;82(3):407-12.

Tackett et al., Unwinding of unnatural substrates by a DNA helicase. Biochemistry. Jan. 16, 2001;40(2):543-8.

Tadey et al., Capillary electrophoretic separation of nucleotide isomers via complexation with cyclodextrin and borate. J Chromatogr B Biomed Appl. Jul. 15, 1994;657(2):365-72.

Thomas et al., Processivity of DNA exonucleases. J Biol Chem. Jan. 25, 1978;253(2):424-9.

Tohda et al., "Channel Mimetic Sensing Membranes for Nucleotides Based on Multitopic Hydrogen Bonding," Israel Journal of Chemistry, vol. 37:267-275 (1997).

Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.

Tung et al., Preparation and applications of peptide-oligonucleotide conjugates. Bioconjug Chem. Sep.-Oct. 2000;11(5):605-18.

Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.

UniProt Database accession No. a4slel sequence. May 15, 2007.
UniProt Database accession No. b4kac8 sequence. Sep. 23, 2008.
UniProt Database accession No. elqus6 sequence. Nov. 30, 2010.
UniProt Database accession No. i3d0e7 sequence. Jul. 11, 2012.
UniProt Database accession No. k0im99 sequence. Nov. 28, 2012.
United States District Court for the District of Delaware Order. *Pacific Biosciences of California, Inc.* v. *Oxford Nanopore Technolgoies, Inc.* Civil Action No. 17-275-RGA. Nov. 9, 2017.

Van De Goor, Nanopore Detection: Threading DNA Through a Tiny Hole. PharmaGenomics, vol. 4 (3):28-30 (2004).

Van Heel et al., Single-particle electron cryo-microscopy:towards atomic resolution. Q Rev Biophys. Nov. 2000;33(4):307-69.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Venkatesan et al., Nanopore sensors for nucleic acid analysis. Nat Nanotechnol. Sep. 18, 2011;6(10):615-24. doi: 10.1038/nnano.2011.129.

Vinson, Proteins in motion. Introduction. Science. Apr. 10, 2009;324(5924):197. doi: 10.1126/science.324.5924.197.

Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.

Wang et al., Bioconjugation by copper(I)-catalyzed azide-alkyne [3 + 2] cycloaddition. J Am Chem Soc. Mar. 19, 2003;125(11):3192-3.

Wang et al., Nanopores with a spark for single-molecule detection. Nat Biotechnol. Jul. 2001;19(7):622-3.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wemmer et al., Preparation and melting of single strand circular DNA loops. Nucleic Acids Res. Dec. 9, 1985;13(23):8611-21.

Winters-Hilt et al., Highly accurate classification of Watson-Crick basepairs on termini of single DNA molecules. Biophys J. Feb. 2003;84(2 Pt 1):967-76.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Woodman et al., Archaeal He1308 domain V couples DNA binding to ATP hydrolysis and positions DNA for unwinding over the helicase ratchet. J Mol Biol. Dec. 14, 2007;374(5):1139-44. Epub Oct. 10, 2007.

Wu et al., Protein nanopores with covalently attached molecular adapters. J Am Chem Soc. Dec. 26, 2007;129(51):16142-8. Epub Nov. 30, 2007.

Xie et al., Single-molecule observation of the catalytic subunit of cAMP-dependent protein kinase binding to an inhibitor peptide. Chem Biol. Jan. 2005;12(1):109-20.

Yamagata et al., Overexpression, purification and characterization of RecJ protein from Thermus thermophilus HB8 and its core domain. Nucleic Acids Res. Nov. 15, 2001;29(22):4617-24.

Yoshina-Ishii et al., Arrays of mobile tethered vesicles on supported lipid bilayers. J Am Chem Soc. Apr. 2, 2003;125(13):3696-7.

Berger et al., Universal bases for hybridization, replication and chain termination. Nucleic Acids Res. Aug. 1, 2000;28(15):2911-4.

Heredia et al., In vitro double transposition for DNA identification. Anal Biochem. Apr. 1, 2010;399(1):78-83. doi:10.1016/j.ab.2009.11.030. Epub Nov. 26, 2009.

Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas. 0800741105. Epub Jun. 30, 2008.

Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.

Hobbs et al., SSB protein limits RecOR binding onto single-stranded DNA. J Biol Chem. Apr. 13, 2007;282(15):11058-67. Epub Feb. 1, 2007.

Kozlov et al., Regulation of Single-stranded DNA Binding by the C Termini of *Escherichia coli* Single-stranded DNA-binding (SBB) Protein. J. Biol. Chem. May 28, 2010;285(22):17246-52.

North et al., Host factors that promote transpososome disassembly and the PriA-PriC pathway for restart primosome assembly. Mol Microbiol. Jun. 2005;56(6):1601-16.

Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.

* cited by examiner

SAMPLE PREPARATION METHOD

RELATED APPLICATIONS

This Application is a national stage filing under 35 U.S.C. § 371 of International Application No. PCT/GB2015/050483, which has an international filing date of Feb. 19, 2015; and claims foreign priority benefits under 35 U.S.C. § 119(a)-(d) or 35 U.S.C. § 365(b) of British application No. 1403096.9, filed Feb. 21, 2014, the contents of each of which are herein incorporated by reference in their entireties.

FIELD OF THE INVENTION

The invention relates to an improved method for characterising a template polynucleotide. The method involves using a polymerase to prepare a modified polynucleotide which makes it easier to characterise than the template polynucleotide.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to modify a template polynucleotide to produce a modified polynucleotide which provides different information from the original template polynucleotide when it is characterized using a transmembrane pore, such as by strand sequencing. Subsequent characterisation of the modified polynucleotide using a transmembrane pore allows the character of the template polynucleotide to be more easily determined.

The improved method uses a polymerase and a population of free nucleotides which are capable of hybridising to the template polynucleotide. The polymerase uses the template polynucleotide as a template to form a modified polynucleotide from the population of free nucleotides. The identity of the free nucleotides is chosen such that the polymerase replaces one or more of the nucleotide species in the template polynucleotide with a different nucleotide species when forming the modified polynucleotide. For instance, the polymerase may replace deoxyguanosine monophosphate (dGMP) in the template polynucleotide with deoxyinosine monophosphate (dIMP) in the modified polynucleotide.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the template polynucleotide with different nucleotide species in the modified nucleotide, the modified polynucleotide contains k-mers which differ from those in the template polynucleotide. The different k-mers in the modified polynucleotide are capable of producing different current measurements from the k-mers in the template polynucleotide and so the modified polynucleotide provides different information from the template polynucleotide. The additional information from the modified polynucleotide can make it easier to characterise the template polynucleotide. In some instances, the modified polynucleotide itself may be easier to characterise. For instance, the modified polynucleotide may be designed to include k-mers with an increased separation or a clear separation between their current measurements or k-mers which have a decreased noise. The information from the modified polynucleotide can also be combined with information from the template polynucleotide to improve the overall accuracy of characterisation.

Accordingly, the invention provides a method of characterising a template polynucleotide, comprising:

a) contacting the template polynucleotide with a polymerase and a population of free nucleotides under conditions in which the polymerase forms a modified polynucleotide using the template polynucleotide as a template, wherein the polymerase replaces one or more of the nucleotide species in the template polynucleotide with a different nucleotide species when forming the modified polynucleotide;

b) contacting the modified polynucleotide with a transmembrane pore such that the modified polynucleotide moves through the pore; and c) taking one or more measurements as the modified polynucleotide moves with respect to the pore wherein the measurements are indicative of one or more characteristics of the modified polynucleotide and thereby characterising the template polynucleotide. The polymerase preferably does not form a complementary polynucleotide if the template polynucleotide is RNA.

The invention also provides a kit for characterising a template polynucleotide comprising (a) a polymerase and (b) a population of free nucleotides comprising a nucleotide species which differs from one or more of the nucleotide species in the template polynucleotide, wherein the polymerase is capable of forming a modified polynucleotide from the free nucleotides using the template polynucleotide as a template and wherein the polymerase is capable of replacing one or more of the nucleotide species in the template polynucleotide with the different nucleotide species.

The invention further provides a method of characterising a homopolynucleotide, comprising:

a) contacting the homopolynucleotide with a polymerase and a population of free nucleotides under conditions in which the polymerase forms a modified polynucleotide using the homopolynucleotide as a template, wherein the modified polynucleotide is not the reverse complement of the homopolynucleotide;

b) contacting the modified polynucleotide with a transmembrane pore such that the modified polynucleotide moves through the pore; and c) taking one or more measurements as the modified polynucleotide moves with respect to the pore wherein the measurements are indicative of one or more characteristics of the modified polynucleotide and thereby characterising the homopolynucleotide.

DESCRIPTION OF THE SEQUENCE LISTING

Figure 1:
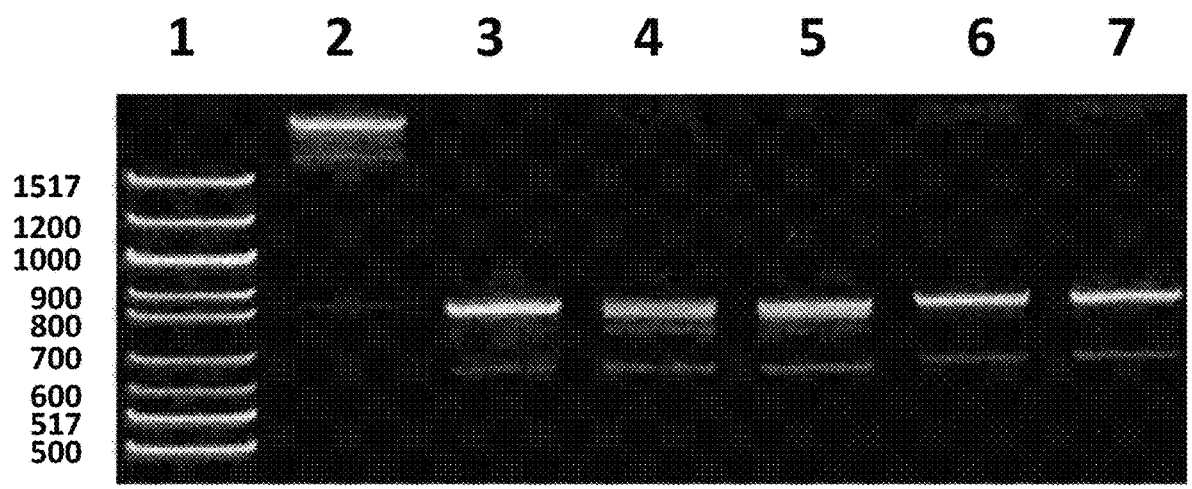
FIG. 1 shows a PAGE of a number of DNA samples produced using the method outlined in Example 1. Lane 1 corresponds to a DNA ladder (masses of the bands are shown on the left-hand side of the gel (1517, 1200, 1000, 900, 800, 700, 600, 517 and 500 bps)). Lane 2 shows the ssDNA control strand (SEQ ID NO: 34 attached at its 3' end to four iSpC3 spacers which are attached at the opposite end to SEQ ID NO: 41). Lane 3 shows the dsDNA control (SEQ ID NO: 34 is attached at its 3' end to four iSpC3 spacers which are attached at the opposite end to the 5' end of SEQ ID NO: 38). Lane 4 shows the dsDNA produced by providing the following dNTP's—dATP, dTTP, dGTP and dCTP. Lane 5 shows the dsDNA sample produced by providing the following dNTP's—dATP, dCTP, dGTP and 5-propynyl-2'-deoxyuridine-5'-triphosphate. Lane 6 shows the dsDNA sample produced by providing the following dNTP's—dATP, dCTP, dTTP and 6-thio-2'-deoxyguanosine-5'-triphosphate. Lane 7 shows the dsDNA sample produced by providing the following dNTP's—dATP, dCTP, 5-propynyl-2'-deoxyuridine-5'-triphosphate and 6-thio-2'-deoxyguanosine-5'-triphosphate
Figure 2:
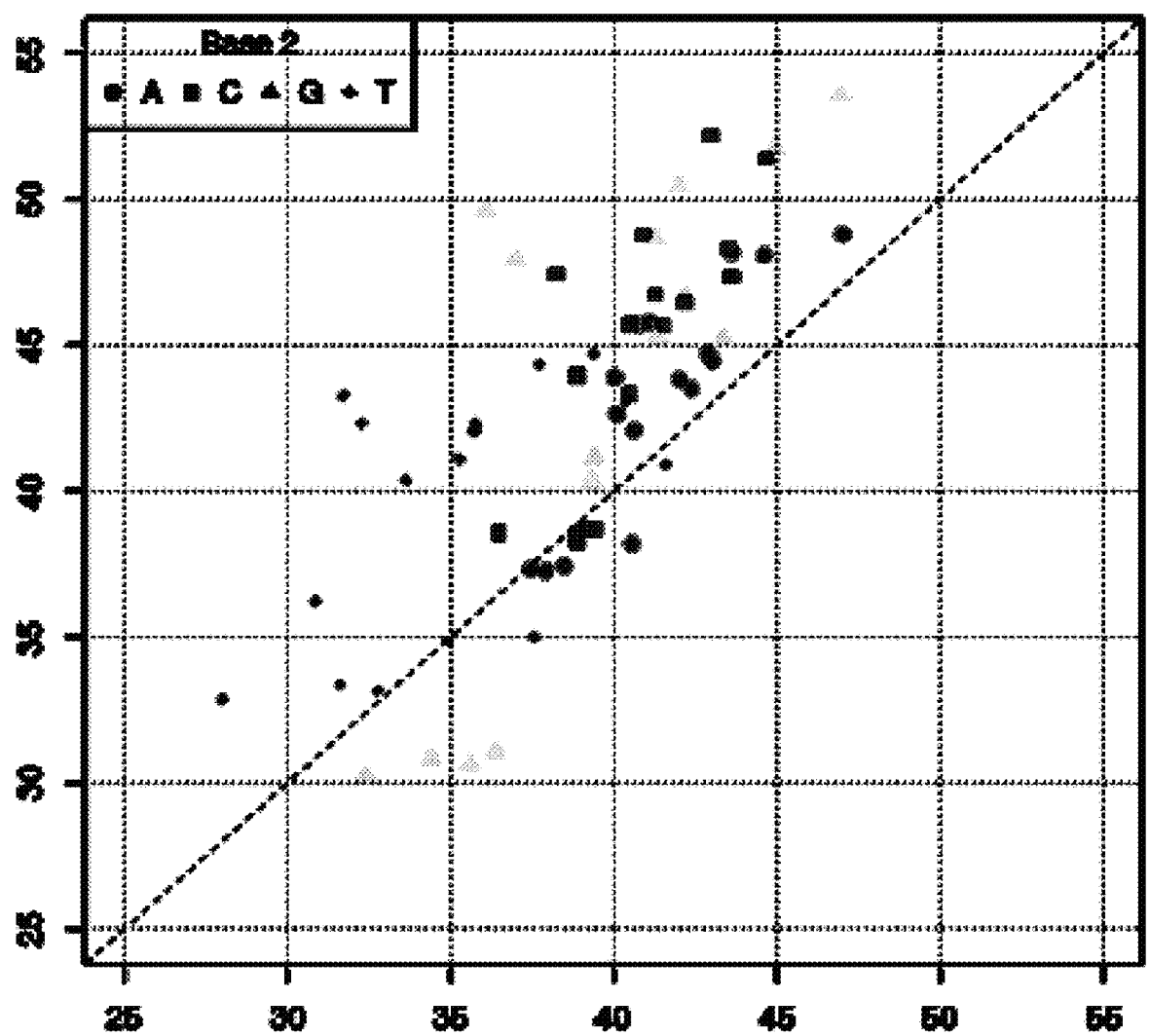
FIG. 2 shows a diagonal dot plot for the modified DNA construct which was made up of C, A, G and 5-propynyl-2'-deoxyuridine-5'-triphosphate. The diagonal dot plot displays the current level for each base combination in the modified strand plotted against its equivalent in an unmodified strand, such that the large changes in the current-sequence relationship are represented by large displacements from the diagonal.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from E. coli. It encodes the exonuclease I enzyme (EcoExo I) from E. coli.

SEQ ID NO: 11 shows the amino acid sequence of exonuclease I enzyme (EcoExo I) from E. coli.

SEQ ID NO: 12 shows the codon optimised polynucleotide sequence derived from the xthA gene from E. coli. It encodes the exonuclease III enzyme from E. coli.

SEQ ID NO: 13 shows the amino acid sequence of the exonuclease III enzyme from E. coli. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from T. thermophilus. It encodes the RecJ enzyme from T. thermophilus (TthRecJ-cd).

SEQ ID NO: 15 shows the amino acid sequence of the RecJ enzyme from T. thermophilus (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the amino acid sequence for the Klenow fragment.

SEQ ID NO: 27 shows the polynucleotide sequence, used in Example 1, for a 600 bp fragment of lambda DNA. This sequence shows the sense sequence of dsDNA.

SEQ ID NO: 28 shows the polynucleotide sequence of a primer used in Example 1.

SEQ ID NO: 29 shows the polynucleotide sequence of a primer used in Example 1.

SEQ ID NO: 30 shows the polynucleotide sequence used in Example 1. SEQ ID NO: 30 is attached at its 5 end to 28 iSpC3 spacers which are attached at the opposite end to two thymines.

SEQ ID NO: 30 is attached at the 3' end to four iSpC3 spacers which are attached at the opposite end to SEQ ID NO: 31. SEQ ID NO: 30 is attached in another polynucleotide sequence to four iSpC3 spacers which are attached at the opposite end to SEQ ID NO: 33.

SEQ ID NO: 31 shows the polynucleotide sequence used in Example 1 and 6. In Example 1 SEQ ID NO: 31 is attached at the 3' end to four iSpC3 spacers which are attached at the opposite end to SEQ ID NO: 30.

SEQ ID NO: 32 shows the polynucleotide sequence of a primer used in Example 1. The 5' end of the sequence contains a phosphate group.

SEQ ID NO: 33 shows a polynucleotide sequence used in Example 1. SEQ ID NO: 33 is attached at its 5' end to four iSpC3 spacers which are attached at the opposite end to SEQ ID NO: 30.

SEQ ID NO: 34 shows the polynucleotide sequence used in Examples 2-5. SEQ ID NO: 34 is attached at its 3' to four iSpC3 spacers which are attached at the opposite end to the 5' end of SEQ ID NO: 38.

SEQ ID NO: 35 shows a polynucleotide sequence used in Example 6.

SEQ ID NO: 36 shows a polynucleotide sequence used in Example 6 and 7.

SEQ ID NO: 37 shows a polynucleotide sequence used in Example 6.

SEQ ID NO: 38 shows a polynucleotide sequence used in Examples 2-5. SEQ ID NO: 38 is attached to four iSpC3 spacers which are attached at the opposite end to the 3' end of SEQ ID NO: 35.

SEQ ID NO: 39 shows a polynucleotide sequence used in Example 2. SEQ ID NO: 39 is attached at its 3' end to four iSpC3 spacers which are attached at the opposite end to the 5' end of SEQ ID NO: 40.

SEQ ID NO: 40 shows a polynucleotide sequence used in Example 2. SEQ ID NO: 40 is attached at its 5' end to four uracil bases and four iSpC3 spacers which were attached at the opposite end to the 3' end of SEQ ID NO: 39.

SEQ ID NO: 41 shows a polynucleotide sequence used in Example 1.

SEQ ID NO: 42 shows a polynucleotide sequence used in Examples 1-8. Attached to the 3' end of SEQ ID NO: 42 is six iSp18 spacer which are attached at the opposite end to two thymines and a 3' cholesterol TEG.

SEQ ID NO: 43 shows a polynucleotide sequence used in Example 7. The 5' end of the sequence contains a phosphate group. SEQ ID NO: 44 shows a polynucleotide sequence used in Example 7. The 5' end of the sequence contains a phosphate group.

SEQ ID NO: 45 shows a polynucleotide sequence used in Examples 6 and 7.

SEQ ID NO: 46 shows a polynucleotide sequence used in Examples 6 and 7.

SEQ ID NO: 47 shows a polynucleotide sequence used in Example 6.

SEQ ID NO: 48 shows a polynucleotide sequence used in Example 6.

SEQ ID NO: 49 shows a polynucleotide sequence used in Example 6.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes "polynucleotides", reference to "a polymerase" includes two or more such polymerase, reference to "a transmembrane pore" includes two or more such pores, and the like.

All publications, patents and patent applications cited herein, whether supra or infra, are hereby incorporated by reference in their entirety.

Method of the Invention

The present invention provides a method of characterising, such as sequencing, a template polynucleotide. The template polynucleotide is the polynucleotide that will ultimately be characterised, or sequenced, in accordance with the invention. This is discussed in more detail below.

An important component of sequencing polynucleotides using strand sequencing is the discrimination of polymer units made up of k nucleotides where k is a positive integer (i.e. 'k-mers'). In the past, to achieve k-mer discrimination the polynucleotide has been passed through a transmembrane pore, such as a mutant of hemolysin. This has provided current signatures that have been shown to be sequence dependent. It has also been shown that a large number of nucleotides (i.e. a high value of k) contribute to the observed current, making a direct relationship between observed current and polynucleotide sequence challenging. In addition, it has been observed that when polynucleotides are moved through a pore, some current states show high variance. It has also been shown that some mutant pores exhibit higher variance than others.

Pores produced from mutated MspA monomers may display an increased current range, which makes it easier to discriminate between different k-mers, and/or a reduced variance of states, which increases the signal-to-noise ratio. In addition, the number of nucleotides contributing to the current (i.e. the value of k) as the polynucleotide moves through pores constructed from the MspA mutants is decreased. This makes it easier to identify a direct relationship between the observed current as the polynucleotide moves through the pore and the polynucleotide sequence. The signals generated using such pores may still be quite complex and so it remains challenging to sequence certain polynucleotides.

The method involves the formation of a modified polynucleotide. The modified polynucleotide includes one or more modified k-mers which provide different current measurements from the k-mers in the template polynucleotide. The one or more modified k-mers preferably have an increased separation or a clear separation from the k-mers in the template polynucleotide and/or the other k-mers in the modified polynucleotide. The one or more modified k-mers preferably have a decreased (or lower) noise than the k-mers in the template polynucleotide and/or the other k-mers in the template polynucleotide. In some embodiments, the modified polynucleotide comprises one or more k-mers that are easier to characterise (for instance because of an increased or clear separation or decreased noise), but also one or more k-mers which are more difficult to characterise (for instance because of a decreased or lack of separation or increased noise).

The modified polynucleotide provides different information from the template polynucleotide, especially when using strand sequencing. The modified polynucleotide is preferably easier to characterise than the template polynucleotide, especially using strand sequencing. The modified polynucleotide is characterised in order to facilitate the characterisation of the template polynucleotide. Although it is not part of the method of the invention, the template polynucleotide may itself be characterised by contacting the template polynucleotide with a transmembrane pore such that it moves through the pore and by taking one or more measurements as the template polynucleotide moves with respect to the pore wherein the measurements are indicative of one or more characteristics of the template polynucleotide. The information about the character of the template polynucleotide itself may then be used in conjunction with the different information derived from the modified polynucleotide in accordance with the invention to more easily characterise the template polynucleotide.

The method of the invention is particularly advantageous for strand sequencing because the modified polynucleotide provides a different signal from the signal provided if the template polynucleotide is itself sequenced. This different information can be used to facilitate the sequencing of the template polynucleotide, especially if the template polynucleotide has itself undergone strand sequencing.

The method of the invention also has other advantages. For instance, the one or more different nucleotide species in the modified polynucleotide may also be designed to facilitate the addition of one or more chemical groups to the modified polynucleotide.

Template Polynucleotide

The method of the invention involves the modification of a template polynucleotide for characterisation. The template polynucleotide is the polynucleotide that will ultimately be characterised, or sequenced, in accordance with the invention. It may also be called the target polynucleotide or the polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the template polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the template polynucleotide may be attached to each other in any manner. The nucleotides are typically attached by their sugar and phosphate groups as in nucleic acids. The nucleotides may be connected via their nucleobases as in pyrimidine dimers.

The template polynucleotide may be single stranded or double stranded. At least a portion of the polynucleotide is preferably double stranded.

The template polynucleotide can be a nucleic acid, such as deoxyribonucleic acid (DNA) or ribonucleic acid (RNA). The template polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains.

The template polynucleotide is preferably DNA and the nucleotide species in the DNA preferably include deoxyadenosine monophosphate (dAMP), deoxyguanosine monophosphate (dGMP), deoxythymidine monophosphate (dTMP), deoxycytidine monophosphate (dCMP) and deoxymethylcytidine monophosphate.

Alternatively, the template polynucleotide is preferably RNA and the nucleotide species in the RNA preferably include adenosine monophosphate (AMP), guanosine monophosphate (GMP), uridine monophosphate (UMP), cytidine monophosphate (CMP) and 5-methylcytidine monophosphate.

The template polynucleotide can be any length. For example, the template polynucleotide can be at least 10, at least 50, at least 100, at least 150, at least 200, at least 250, at least 300, at least 400 or at least 500 nucleotide pairs in length. The template polynucleotide can be 1000 or more nucleotide pairs, 5000 or more nucleotide pairs in length or 100000 or more nucleotide pairs in length.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Polymerase

The template polynucleotide is contacted with a polymerase. The polymerase may be any of those discussed below with reference to the polynucleotide binding protein. The polymerase is preferably Klenow or 90 North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 90 North. A primer or a 3' hairpin is typically used as the nucleation point for polymerase extension.

Population of Free Nucleotides and Replacing Nucleotide Species

The template polynucleotide is contacted with a population of free nucleotides. The polymerase uses the free nucleotides to form the modified polynucleotide based on the template polynucleotide. The identities of the free nucleotides in the population determine the composition of the modified polynucleotide.

Many of the examples of different nucleotide species given below refer to their monophosphate form. This is because nucleotides contained in polynucleotides (such as the modified polynucleotide) are typically in their monophosphate form. When contacted with the polymerase, the free nucleotides in the population may be in their diphosphate form or triphosphate form or may comprise more than three phosphates, such as four or five phosphates. As a result, any of the nucleotides discussed below may have more than one phosphate when in their free form in the population. The different nucleotide species in the Examples are described with reference to their form in the population of free nucleotides, i.e. as triphosphates.

Each free nucleotide in the population is capable of hybridising or binding to one or more of the nucleotide species in the template polynucleotide. Each free nucleotide in the population is typically capable of specifically hybridising or specifically binding to (i.e. complementing) one or more of the nucleotide species in the template polynucleotide. A nucleotide specifically hybridises or specifically binds to (i.e. complements) a nucleotide in the template polynucleotide if it hybridises or binds more strongly to the nucleotide than to the other nucleotides in the template nucleotide. This allows the polymerase to use complementarity (i.e. base pairing) to form the modified polynucleotide using the template polynucleotide. Typically, each free nucleotide specifically hybridises or specifically binds to (i.e. complements) one of the nucleotides in the template polynucleotide. In some embodiments, a different nucleotide species used in the invention is capable of specifically hybridising or specifically binding to (i.e. complementing) more than one nucleotide species in the template polynucleotide. Universal nucleotides that are useful in these embodiments are discussed in more detail below.

Each different nucleotide species is capable of specifically hybridising or specifically binding to (i.e. complementing) the nucleotide species in the template polynucleotide which is complementary to the nucleotide species it is replacing. For instance, for a DNA template, the different nucleotide species being used to replace dAMP is capable of specifically hybridising or specifically binding to (i.e. complementing) dTMP. Each different nucleotide species used in the method typically hybridises or binds less strongly to those nucleotide species in the template polynucleotide which not are complementary to the nucleotide species it is replacing. For instance, for a DNA template, the different nucleotide species being used to replace dAMP is typically capable of hybridising or binding to dTMP more strongly than it hybridises or binds to dAMP, dGMP or dCMP. A skilled person can design suitable populations of free nucleotides. In some embodiments, the same different nucleotide species is used to replace different nucleotides species in the template polynucleotide. In such embodiments, the different nucleotide species is capable of specifically hybridising or specifically binding to (i.e. complementing) two or more nucleotide species in the template polynucleotide. This means that the different nucleotide species binds more strongly to the two or more nucleotide species it is replacing than the other nucleotides in the template polynucleotide. Universal nucleotides that are useful in these embodiments are discussed in more detail below.

Each free nucleotide is capable of being handled by the polymerase and incorporated into the modified polynucleotide.

The identities of the free nucleotides are such that the polymerase replaces one or more of the nucleotide species in the template polynucleotide with a different nucleotide species when forming the modified polynucleotide. For instance, the polymerase may replace all instances of dGMP in the template polynucleotide with deoxyinosine monophosphate (dIMP) or a modified version of dAMP in the modified polynucleotide. The one or more nucleotide species in the template polynucleotide that are being replaced do not typically appear in the modified polynucleotide.

The method of the invention is illustrated below.

```
Template      . . . ATGCATGCA . . .

Modified      . . . XACGXACGX . . .
```

In the illustration above, both strands are DNA. The template polynucleotide is shown on the top. The modified nucleotide is shown on the bottom. The polymerase has replaced the nucleotide species T (i.e. dTMP) with a different nucleotide species X in the modified polynucleotide. The different nucleotide species may be any of those discussed below. In order to do this, the template polynucleotide is contacted with a polymerase and a population of A, X, G and C. The polymerase is capable of handling X and inserting X at positions where T should appear in the modified polynucleotide, i.e. at positions where A (the nucleotide complementary to T) is present in the template polynucleotide.

One or more of the free nucleotides in the population are nucleotides which differ from the one or more nucleotide species being replaced. These are used to replace the one or more nucleotide species and are discussed in more detail below. The remaining nucleotides in the population are typically nucleotides present in the template polynucleotide. These may be any of the nucleotides discussed above.

Any number of nucleotide species in the template polynucleotide may be replaced with a different nucleotide species. For instance, the polymerase may replace two, three, four, five, six, seven, eight or more of the nucleotide species in the template polynucleotide with a different nucleotide when forming the modified polynucleotide. Wild-type DNA, such as human DNA, may contain more than four nucleotide species (i.e. more than just dAMP, dTMP, dGMP and dCMP) because of the plurality of naturally occurring nucleotide modifications. The polymerase may replace all of the nucleotide species in the template polynucleotide with a different nucleotide when forming the modified polynucleotide. For instance, the polymerase may replace dAMP, dTMP, dGMP and dCMP with modified versions of themselves, such as modified versions each comprising a halogen atom. This can be achieved for template DNA by contacting the DNA with a polymerase and a population of free nucleotides containing the modified versions of dAMP, dTMP, dGMP and dCMP.

In some preferred embodiments, the polymerase replaces each of the two or more nucleotide species in the template polynucleotide with a distinct nucleotide. In other words, each nucleotide species is replaced with distinct nucleotide. For instance, the polymerase may replace dAMP with a modified version of dAMP and replace dTMP with modified version of dTMP. This can be achieved for template DNA by contacting the DNA with a polymerase and a population of free nucleotides containing the modified version of dAMP, the modified version of dTMP, dGMP and dCMP. Alternatively, the polymerase may replace dAMP with a modified version of dAMP and replace dGMP with deoxyinosine monophosphate (dIMP). This can be achieved for template DNA by contacting the DNA with a polymerase and a population of free nucleotides containing the modified version of dAMP, dIMP, dGMP and dCMP.

In other preferred embodiments, the polymerase replaces each of the two or more nucleotide species in the template polynucleotide with the same nucleotide. For instance, the polymerase may replace dCMP and dTMP with dPMP (2'-Deoxy-P-nucleoside monophosphate). This can be achieved for template DNA by contacting the DNA with a polymerase and a population of free dPMP, dGMP and dCMP.

It is clear from the discussion above that the modified polynucleotide differs from the reverse complement of the template polynucleotide.

If the template polynucleotide is DNA, the polymerase may replace deoxycytidine monophosphate (dCMP) with deoxymethylcytidine monophosphate. If the template polynucleotide is DNA, the polymerase preferably does not only replace deoxymethylcytidine monophosphate with deoxycytidine monophosphate (dCMP).

If the template polynucleotide is RNA, the polymerase preferably replaces cytidine monophosphate (CMP) with methylcytidine monophosphate.

Different Nucleotide Species

The one or more different nucleotide species are typically chosen to provide the information of interest from the modified polynucleotide. For instance, T k-mers (i.e. k-mers in which the central nucleotide is thymine-based, such as TTA, GTC, GTG and CTA) typically have the lowest current states. Modified versions of T nucleotides may be introduced into the modified polynucleotide to reduce the current states further and thereby increase the total current range seen when the modified polynucleotides moves through the pore.

G k-mers (i.e. k-mers in which the central nucleotide is guanine-based, such as TGA, GGC, TGT and CGA) tend to be strongly influenced by other nucleotides in the k-mer and so modifying the G nucleotides in the modified polynucleotide may help them to have more independent current positions.

Replacing two nucleotide species with the same different nucleotide species may facilitate characterisation because it is then only necessary to map 3-nucleotide k-mers in the modified polynucleotide. However, such modifications do reduce the information provided by the modified polynucleotide and so it is typically necessary to also characterise the template polynucleotide itself (for instance using strand sequencing) to obtain full information about the template polynucleotide.

Replacing one or more nucleotide species with abasic nucleotides results in characteristic current spikes. This allows the clear highlighting of the positions of the one or more nucleotide species in the template polynucleotide.

Replacing all cytosine (C)-based nucleotides in the template polynucleotide with methyl-C (meC)-based nucleotides in the modified polynucleotide allows the building of a GTAmeC model from which the characteristics of meC containing k-mers may be determined. Such characteristics can then be used to distinguish these k-mers from normal C k-mers in the template polynucleotide.

If the template polynucleotide is DNA, the different nucleotide species in the modified polynucleotide preferably comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the template polynucleotide is RNA, the different nucleotide species in the modified polynucleotide preferably comprises a nucleobase which differs from adenine, guanine, uracil, cytosine or methylcytosine and/or comprises a nucleoside which differs from adenosine, guanosine, uridine, cytidine or methylcytidine. The different nucleobase and/or nucleoside is/are capable of complementing one or more of the nucleotides in the template polynucleotide. Commercially available nucleosides include, but are not limited to, 2,6-Diaminopurine-2'-deoxyriboside, 2-Aminopurine-2'-deoxyriboside, 2,6-Diaminopurine-riboside, 2-Aminopurine-riboside, Pseudouridine, Puromycin, 2,6-Diaminopurine-2'-O-methylriboside, 2-Aminopurine-2'-O-methylriboside and Aracytidine. The different nucleotide species may comprise any of these nucleosides.

The different nucleotide species may be a universal nucleotide. A universal nucleotide is one which will hybridise or bind to some degree to all of the nucleotides in the template polynucleotide. A universal nucleotide is preferably one which will hybridise or bind to some degree to nucleotides comprising the nucleosides adenosine (A), thymine (T), uracil (U), guanine (G) and cytosine (C). The universal nucleotide may hybridise or bind more strongly to some nucleotides than to others. For instance, a universal nucleotide (I) comprising the nucleoside, 2'-deoxyinosine, will show a preferential order of pairing of I-C>I-A>I-G approximately=I-T. The polymerase will replace a nucleotide species with a universal nucleotide if the universal nucleotide takes the place of the nucleotide species in the population. For instance, the polymerase will replace dGMP with a universal nucleotide, if it is contacted with a population of free dAMP, dTMP, dCMP and the universal nucleotide.

The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The different nucleotide species preferably comprises a chemical atom or group absent from the nucleotide species it is replacing. The chemical group is preferably a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

Commercially available nucleosides comprising chemical groups which are absent from naturally-occurring nucleosides include, but are not limited to, 6-Thio-2'-deoxyguanosine, 7-Deaza-2'-deoxyadenosine, 7-Deaza-2'-deoxyguanosine, 7-Deaza-2'-deoxyxanthosine, 7-Deaza-8-aza-2'-deoxyadenosine, 8-5'(5'S)-Cyclo-2'-deoxyadenosine, 8-Amino-2'-deoxyadenosine, 8-Amino-2'-deoxyguanosine, 8-Deuterated-2'-deoxyguanosine, 8-Oxo-2'-deoxyadenosine, 8-Oxo-2'-deoxyguanosine, Etheno-2'-deoxyadenosine, N6-Methyl-2'-deoxyadenosine, O6-Methyl-2'-deoxyguanosine, O6-Phenyl-2'deoxyinosine, 2'-Deoxypseudouridine, 2-Thiothymidine, 4-Thio-2'-deoxyuridine, 4-Thiothymidine, 5' Aminothymidine, 5-(1-Pyrenylethynyl)-2'-deoxyuridine, 5-(C2-EDTA)-2'-deoxyuridine, 5-(Carboxy) vinyl-2'-deoxyuridine, 5,6-Dihydro-2'-deoxyuridine, 5,6-Dihydrothymidine, 5-Bromo-2'-deoxycytidine, 5-Bromo-2'-deoxyuridine, 5-Carboxy-2'-deoxycytidine, 5-Fluoro-2'-deoxyuridine, 5-Formyl-2'-deoxycytidine, 5-Hydroxy-2'-deoxycytidine, 5-Hydroxy-2'-deoxyuridine, 5-Hydroxymethyl-2'-deoxycytidine, 5-Hydroxymethyl-2'-deoxyuridine, 5-Iodo-2'-deoxycytidine, 5-Iodo-2'-deoxyuridine, 5-Methyl-2'-deoxycytidine, 5-Methyl-2'-deoxyisocytidine, 5-Propynyl-2'-deoxycytidine, 5-Propynyl-2'-deoxyuridine, 6-O-(TMP)-5-F-2'-deoxyuridine, C4-(1,2,4-Triazol-1-yl)-2'-deoxyuridine, C8-Alkyne-thymidine, dT-Ferrocene, N4-Ethyl-2'-deoxycytidine, O4-Methylthymidine, Pyrrolo-2'-deoxycytidine, Thymidine Glycol, 4-Thiouridine, 5-Methylcytidine, 5-Methyluridine, Pyrrolocytidine, 3-Deaza-5-Aza-2'-O-methylcytidine, 5-Fluoro-2'-O-Methyluridine, 5-Fluoro-4-O-TMP-2'-O-Methyluridine, 5-Methyl-2'-O-Methylcytidine, 5-Methyl-2'-O-Methylthymidine, 2',3'-Dideoxyadenosine, 2',3'-Dideoxycytidine, 2',3'-Dideoxyguanosine, 2',3'-Dideoxythymidine, 3'-Deoxyadenosine, 3'-Deoxycytidine, 3'-Deoxyguanosine, 3'-Deoxythymidine and 5'-O-Methylthymidine. The different nucleotide species may comprise any of these nucleosides. The different nucleotide species is preferably one of those in Table 2. The different nucleotide species is most preferably 2'-fluoro-2'-deoxyadenosine or 5-carboxy-2'-deoxycytidine.

Alternatively, the different nucleotide species preferably lacks a chemical group or atom present in the nucleotide species it is replacing.

The different nucleotide species preferably has an altered electronegativity compared with the one or more nucleotides being replaced. The different nucleotide species having an altered electronegativity preferably comprises a halogen atom. The halogen atom may be attached to any position on the different nucleotide species, such as the nucleobase and/or the sugar. The halogen atom is preferably fluorine (F), chlorine (Cl), bromine (Br) or iodine (I). The halogen atom is most preferably F or I.

Commercially available nucleosides comprising a halogen include, but are not limited to, 8-Bromo-2'-deoxyadenosine, 8-Bromo-2'-deoxyguanosine, 5-Bromouridine, 5-Iodouridine, 5-Bromouridine, 5-Iodouridine, 5'-Iodothymidine and 5-Bromo-2'-O-methyluridine. The different nucleotide species may comprise any of these nucleosides.

Any of the nucleotides mentioned in the Examples may also be used in the method of the invention.

Template RNA

If the template polynucleotide is RNA, the polymerase preferably does not form a complementary polynucleotide, such as complementary DNA. The invention does not concern any of the methods of characterising a method of characterising a target RNA disclosed in International Application No. PCT/GB2014/053121.

Selective Removal of Nucleobases

Step a) of the method preferably further comprises selectively removing the nucleobases from the one or more different nucleotides species in the modified polynucleotide. This results in abasic nucleotides in the modified polynucleotide. An abasic nucleotide is a nucleotide that lacks a nucleobase. The abasic nucleotide typically contains a sugar and at least one phosphate group. The sugar is typically a pentose sugar, such as ribose and deoxyribose. The abasic nucleotide is typically an abasic ribonucleotide or an abasic deoxyribonucleotide. The abasic nucleotide typically contains a monophosphate, diphosphate or triphosphate. Phosphates may be attached on the 5' or 3' side of an abasic nucleotide.

The nucleobases may be selectively removed using any method known in the art. For instance, certain DNA repair proteins, such as human alkyladenine DNA glycosylase (hAAG), are capable of selectively removing 3-methyl adenine, 7-methyl guanine, 1, N6-ethenoadenine and hypoxanthine from nucleotides. Also, dUMP can be selectively removed using uracil DNA glycosylase.

Selective Modification of the One or More Different Nucleotides

Step a) of the method preferably further comprises selectively modifying the one or more different nucleotides species in the modified polynucleotide. Further modification can also be used to produce different k-mers with different current measurements. Further modification may also be used to label the modified polynucleotide or link it to another molecule or surface.

The one or more different nucleotide species may be selectively modified using any of the chemical groups or atoms discussed above. For instance, dPMP may be selectively modified to include a halogen atom.

The one or more different nucleotide species may be selectively modified by glycosylation or pegylation.

Single Stranded Template Polynucleotide

The template polynucleotide may be single stranded. A primer may be annealed to the template polynucleotide and used as a nucleation site for formation of the modified polynucleotide by the polymerase. Once the modified polynucleotide is formed, the template and modified polynucleotides may be linked using a hairpin adaptor. For instance, a hairpin adaptor may be ligated to the two hybridised polynucleotides.

If the template polynucleotide is single stranded, the method preferably further comprises before step a) ligating a hairpin adaptor to one end of the template polynucleotide such that in step a) the ligated hairpin adaptor acts as a primer for formation of the modified polynucleotide by the polymerase such that the modified and template polynucleotides are ligated by the hairpin adaptor.

Suitable hairpin adaptors can be designed using methods known in the art. The hairpin loop may be any length. The hairpin loop is typically 50 or fewer bases, such as 40 or fewer bases, 30 or fewer bases, 20 or fewer bases or 10 or fewer bases, in length. The hairpin loop is preferably from about 1 to 50, from 2 to 40 or from 6 to 30 bases in length. Longer lengths of the hairpin loop, such as from 15 to 50 bases, are preferred if the loop is involved in the differential selectability of the adaptor. Similarly, shorter lengths of the hairpin loop, such as from 1 to 5 bases, are preferred if the loop is not involved in the selectable binding as discussed below.

The hairpin adaptor may be ligated to either end of the template polynucleotide, i.e. the 5' or the 3' end. The hairpin adaptor may be ligated to the template polynucleotide using any method knows in the art. The hairpin adaptor may be ligated using a ligase, such as T4 DNA ligase, *E. coli* DNA ligase, Taq DNA ligase, Tma DNA ligase and 9° N DNA ligase.

The hairpin adaptor preferably comprises a selectable binding moiety. This allows the template polynucleotide and the modified polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridize) to a surface coated with homologus sequences. Alternatively, selectable nucleic acid sequences specifically bind to a surface coated with nucleic acid binding proteins.

The hairpin adaptor and/or the selectable binding moiety may comprise a region that can be cut, nicked, cleaved or hydrolysed. Such a region can be designed to allow the modified polynucleotide and temple polynucleotide (which may be attached together via the hairpin adaptor) to be removed from the surface to which it is bound following purification or isolation. It can also be designed to allow the modified polynucleotide to be separated from the template polynucleotide. Suitable regions are known in the art. Suitable regions include, but are not limited to, an RNA region, a region comprising desthiobiotin and streptavidin, a disulphide bond and a photocleavable region.

If the template polynucleotide is single stranded, the method preferably further comprises before step a) ligating a first hairpin adaptor to one end of the template polynucleotide such that in step a) the first ligated hairpin adaptor acts as a primer for formation of the modified polynucleotide by the polymerase such that the modified and template polynucleotides are ligated by the first hairpin adaptor and after step (a) but before step (b) ligating a second hairpin adaptor to the end of the template polynucleotide or the modified polynucleotide not ligated to the first hairpin adaptor, contacting the resulting construct with a polymerase and population of free nucleotides under conditions in which the polymerase forms a new polynucleotide using the template polynucleotide and the modified polynucleotide as templates to produce a double stranded construct in which the two strands are linked by the second hairpin adaptor. The population of free nucleotides in this embodiment may be any of the nucleotides discussed above, including the nucleotides in the template polynucleotide, DNA or RNA nucleotides or the different nucleotide species. The double stranded construct may then be characterised in accordance with the invention. The information in the single stranded template polynucleotide is not only doubled by the formation of the modified polynucleotide but also doubled again by the formation of the new polynucleotide.

Double Stranded Template Polynucleotide

The template polynucleotide may be double stranded. A hairpin adaptor which does not link the two strands may be ligated to one end of the double stranded template polynucleotide, i.e. to one end of one of the strands of the double stranded template polynucleotide. The hairpin adaptor may then be used as the nucleation site for primer extension.

If the template polynucleotide is double stranded, the method preferably further comprises before step (a) ligating a first hairpin adaptor to one end of the template polynucleotide and separating the two strands of the template polynucleotide to form a single stranded template polynucleotide construct. The single stranded template polynucleotide construct may then be used as a template to form the modified polynucleotide in accordance with the invention.

Suitable hairpins can be designed as described above. The hairpin loops may be any length as described above. The first hairpin adaptor may be ligated to either end of the template polynucleotide, i.e. the 5' or the 3' end, and the second hairpin adaptor is ligated to the other end. The hairpin adaptors may be ligated to the template polynucleotide as discussed above.

The two strands of the template polynucleotide may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea). The polymerase preferably simultaneously separates the two strands of the template polynucleotide and uses the strands as templates to form the modified polynucleotide.

The method preferably further comprises before step a) ligating a second hairpin adaptor to one end of the single stranded template polynucleotide construct such that in step (a) the ligated hairpin adaptor acts as a primer for formation of the modified polynucleotide by the polymerase such that the modified polynucleotide and the single stranded polynucleotide construct are ligated by the second hairpin adaptor.

The second hairpin may be any of the hairpins discussed above.

The second hairpin adaptor further comprises a region at which the hairpin can be cut, nicked, cleaved or hydrolysed and the method further comprises before step (c) cutting the second hairpin adaptor to open the circular polynucleotide construct and produce a double stranded polynucleotide. Suitable regions are discussed above.

The first or second hairpin adaptor preferably comprises a selectable binding moiety as discussed above.

Leader Sequence

Before step b), the method preferably comprises attaching to the modified polynucleotide a leader sequence which preferentially threads into the pore. The leader sequence facilitates the method of the invention. The leader sequence is designed to preferentially thread into the transmembrane pore and thereby facilitate the movement of target polynucleotide through the pore. The leader sequence typically comprises a polymer. The polymer is preferably negatively charged. The polymer is preferably a polynucleotide, such as DNA or RNA, a modified polynucleotide (such as abasic DNA), PNA, LNA, BNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises one or more spacers.

The leader sequence can be any length, but is typically 10 to 150 nucleotides in length, such as from 20 to 150 nucleotides in length. The length of the leader typically depends on the transmembrane pore used in the method.

Characterisation

Step b) comprises contacting the modified polynucleotide with a transmembrane pore such that the modified polynucleotide moves through the pore. The modified polynucleotide and the template polynucleotide may be contacted with a transmembrane pore such they both move through the pore.

Steps b) and c) of the method are preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the polynucleotide moves with respect to the pore is used to determine the sequence of the modified polynucleotide. This is strand sequencing. If the modified polynucleotide is sequenced, the sequence of the template polynucleotide may then be reconstructed.

The whole or only part of the modified polynucleotide and/or template polynucleotide may be characterized, for instance sequenced, using this method. The length of the template polynucleotide is discussed above. The modified polynucleotide(s) will be substantially the same length.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro. The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The modified polynucleotide and/or template polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the pore. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

Suitable methods of coupling are disclosed in International Application No. PCT/GB12/05119 1 (published as WO 2012/164270) and UK Application No. 1406155.0.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin (the sequence of one monomer or subunit of α-hemolysin-NN is shown in SEQ ID NO: 4), anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The method of the invention involves measuring one or more characteristics of the modified polynucleotide(s) or template polynucleotide. The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Step b) preferably further comprises contacting the modified polynucleotide with a polynucleotide binding protein such that the protein controls the movement of the modified polynucleotide through the pore. More preferably, the method comprises (a) contacting the modified polynucleotide with a transmembrane pore and a polynucleotide binding protein such that the polynucleotide moves through the pore and the protein controls the movement of the polynucleotide through the pore and (b) measuring the current passing through the pore as the polynucleotide moves with respect to the pore wherein the current is indicative of one or more characteristics of the polynucleotide and thereby characterising the modified polynucleotide.

In some instances, both the template and modified polynucleotides move through the pore, such as when they are ligated to one another. Step b) preferably further comprises contacting the modified polynucleotide and the template polynucleotide with a polynucleotide binding protein such that the protein controls the movement of both polynucleotides through the pore. More preferably, the method comprises (a) contacting the modified polynucleotide and the template polynucleotide with a transmembrane pore and a polynucleotide binding protein such that both polynucleotides move through the pore and the protein controls the movement of the polynucleotides through the pore and (b) measuring the current passing through the pore as the polynucleotides move with respect to the pore wherein the current is indicative of one or more characteristics of the polynucleotides and thereby characterising the template polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from E. coli (SEQ ID NO: 11), exonuclease III enzyme from E. coli (SEQ ID NO: 13), RecJ from T. thermophilus (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 20), TraI Eco (SEQ ID NO: 21), XPD Mbu (SEQ ID NO: 22) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925; PCT/GB2013/051924, PCT/GB2013/051928 and PCT/GB2014/052736.

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 8 comprises E94C/A360C and then (ΔM1)G1G2 (i.e. deletion of M1 and then addition G1 and G2).

Any number of helicases may be moved past the one or more spacers in accordance with the invention. For instance, 1, 2, 3, 4, 5, 6, 7, 8, 9, 10 or more helicases may be moved past the one or more spacers. In some embodiments, different numbers of helicases may be moved past each spacer. For instance, if two helicases are stalled using two separate spacers, one helicase (the first helicase) may be moved past the first spacer, but two helicases (the first and second helicases) may be moved past the second spacer.

The method of the invention preferably comprises moving two or more, such as three or more or four or more, stalled helicases past one or more spacers. The two or more helicases are typically the same helicases. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925; PCT/GB2013/051924; PCT/GB2013/051928; and PCT/GB2014/052736.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature.

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

The method of characterising a modified or a template polynucleotide preferably involves contacting the polynucleotide with a pore and a polynucleotide binding protein derived from a helicase. Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the bilayer. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the bilayer.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Steps b) and c) of the method are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:
(i) providing the/each polynucleotide with one or more helicases and one or more molecular brakes attached to the/each polynucleotide;
(b) contacting the/each polynucleotide with a transmembrane pore and applying a potential across the pore such that the one or more helicases and the one or more molecular brakes are brought together and both control the movement of at least one strand of the/each polynucleotide through the pore;
(c) taking one or more measurements as the/each polynucleotide moves with respect to the pore wherein the measurements are indicative of one or more characteristics of the polynucleotide and thereby characterising the modified or template polynucleotide.

This type of method is discussed in detail in the International Application No. PCT/GB2014/052737.

Kits

The present invention also provides a kit for characterising a template polynucleotide. The kit comprises (a) a polymerase and (b) a population of free nucleotides comprising a nucleotide species which differs from one or more of the nucleotide species in the template polynucleotide. The polymerase is capable of forming a modified polynucleotide from the free nucleotides using the template polynucleotide as a template. The polymerase is capable of replacing one or more of the nucleotide species in the template polynucleotide with the different nucleotide species.

The kit preferably further comprises a hairpin loop and/or a leader sequence which is capable of preferentially threading into a transmembrane pore. The kit preferably further comprises a transmembrane pore. The kit preferably further comprises a polynucleotide binding protein.

Any of the embodiments discussed above with reference to the method of the invention equally apply to the kits. The kit may further comprise the components of a membrane, such as the components of an amphiphilic layer or a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Homopolynucleotide Method

The invention also provides a method of characterising a homopolynucleotide. A homopolynucleotide is a polynucleotide composed of only one nucleotide species. The homopolynucleotide may comprise any of the nucleotide species discussed above. Homopolynucleotides include, but are not limited, to poly(A), poly(dA), poly(U), poly(dU), poly(C), poly(dC), poly(G), poly(dG), poly(T) and poly (dT). Homopolynucleotides are difficult to characterise using a pore, such as in strand sequencing, because the presence of a single nucleotide species results in a constant current signal as the homopolynucleotide passes through the pore. The method of the invention avoids this issue as discussed below, The homopolynucleotide may be any length. The homopolynucleotide may be from 2 to 100 nucleotides in length, such as from 5 to 50 or from 10 to 40 nucleotides in length. The homopolynucleotide may form part of a longer template polynucleotide.

The homopolynucleotide is contacted with a population of free nucleotides. The polymerase uses the free nucleotides to form the modified polynucleotide based on the homopolynucleotide. The identities of the free nucleotides in the population determine the composition of the modified polynucleotide.

Each free nucleotide in the population is capable of hybridising or binding to the nucleotide species in the homopolynucleotide. Each free nucleotide in the population is typically capable of specifically hybridising or specifically binding to (i.e. complementing) the nucleotide species in the template polynucleotide. This allows the polymerase to use complementarity (i.e. base pairing) to form the modified polynucleotide using the homopolynucleotide.

Each free nucleotide is capable of being handled by the polymerase and incorporated into the modified polynucleotide.

The modified polynucleotide is not the reverse complement of the homopolynucleotide. The polymerase when forming the modified polynucleotide randomly replaces some of the instances of the nucleotide species that is complementary to the nucleotide species in the homopolynucleotide with a different nucleotide species. For instance, the polymerase may replace some instances of dTMP with a modified version of dTMP in the modified polynucleotide when using a poly(dAMP) homopolynucleotide as a template.

The random replacement of some instances of the nucleotide species results in a modified polynucleotide which provides a variable current signal as it passes though the pore. This allows the homopolynucleotide to be more easily characterised.

The different nucleotide species is preferably a modified version of the nucleotide species being replaced. It may be modified in any of the way discussed above.

The method of the invention is illustrated below.

```
Homo        . . . AAAAAAAAA . . .
Modified    . . . XTTXXTTTX . . .
```

In the illustration above, both strands are based on DNA. The homopolynucleotide is shown on the top and is poly(dAMP). The modified nucleotide is shown on the bottom. The polymerase has randomly replaced some of the nucleotide species T (i.e. dTMP) with a different nucleotide species X in the modified polynucleotide. The different nucleotide species X may be any of those discussed above. X is preferably a modified version of T. It may be modified in any of the ways discussed above. In order to do this, the template polynucleotide is contacted with a polymerase and a population of T and X. The polymerase is capable of handling X and randomly inserting X at positions where T should appear in the modified polynucleotide.

Any number of instances of the nucleotide species may be replaced with a different nucleotide species. For instance, the polymerase may replace at least 5%, at least 10%, at least 20%, at least 30%, at least 40%, at least 50%, at least 60%, at least 70% or at least 80% of the nucleotide species with a different nucleotide species. The polymerase typically does not replace all of the nucleotide species with a different nucleotide species. The number of instances of the nucleotide species replaced with a different nucleotide species is typically dependent on the relative strengths of hybridisation or binding to the homopolynucleotide of the different nucleotide species and the nucleotide species being replaced and/or the ratio of the different nucleotide species and the nucleotide species being replaced in the population of free nucleotides.

In some preferred embodiments, the polymerase when forming the modified polynucleotide randomly replaces some of the instances of the nucleotide species that is complementary to the nucleotide species in the homopolynucleotide with a first different nucleotide species and randomly replaces other instances of the nucleotide species that is complementary to the nucleotide species in the homopolynucleotide with a second different nucleotide species. In other words, different instances of the nucleotide species are replaced with distinct nucleotide. For instance, the polymerase may replace some instances of dTMP with a modified version of dTMP, such as dTMP lacking a native chemical group, and replace other instances of dTMP with different modified version of dTMP, such as dTMP modified with a halogen atom. This can be achieved for template DNA by contacting the DNA with a polymerase and a population of free nucleotides containing dTMP, the modified version of dTMP and the different modified version of dTMP. Some instances of the nucleotide species may not be replaced.

This embodiment is illustrated below.

```
Homo        . . . AAAAAAAAA . . .
Modified    . . . XTXYXTYTX . . .
```

In the illustration above, both strands are based on DNA. The homopolynucleotide is shown on the top and is poly(dAMP). The modified nucleotide is shown on the bottom. The polymerase has randomly replaced some of the nucleotide species T (i.e. dTMP) with two different nucleotide species X and Y in the modified polynucleotide. The different nucleotide species X and Y may be any of those discussed above. X and Y are preferably different modified versions of T. They may be modified in any of the ways discussed above. In order to do this, the template polynucleotide is contacted with a polymerase and a population of T, X and Y. The polymerase is capable of handling X and Y and inserting them at positions where T should appear in the modified polynucleotide. The relative number of T, X and Y in the modified polynucleotide is typically dependent on the relative strengths of hybridisation or binding of T, X and Y to the homopolynucleotide and/or the ratio of T, X and Y in the population of free nucleotides.

Alternatively, all instances of the nucleotide species in template polynucleotide may be replaced, either with the first different nucleotide species or the second nucleotide species. This embodiment is illustrated below using the same key as above.

```
Homo        . . . AAAAAAAAA . . .
Modified    . . . XYXYXYYXX . . .
```

In order to do this, the template polynucleotide is contacted with a polymerase and a population of X and Y. The relative number of X and Y in the modified polynucleotide is typically dependent on the relative strengths of hybridisation or binding of X and Y to the homopolynucleotide and/or the ratio of X and Y in the population of free nucleotides.

The modified polynucleotide formed using the homopolynucleotide as a template then is contacted with a transmembrane pore such that the modified polynucleotide moves through the pore. One or more measurements are then taken as the modified polynucleotide moves with respect to the pore wherein the measurements are indicative of one or more characteristics of the modified polynucleotide and thereby characterising the homopolynucleotide. Any of the embodiments discussed above are applicable to these steps.

The following Examples illustrate the invention.

EXAMPLES

Example 1

This example describes how 600 bp strands of DNA were made by filling in ssDNA from a 5' leader and tether site and a 3' hairpin, using Klenow (SEQ ID NO: 26) and dNTPs (when at least one of the dNTPs was a different nucleotide species from dAMP, dGMP, dTMP and dCMP).

Materials and Methods 1.1 Preparation of ssDNA Sample

The 600 bp ssDNA fragment of Lambda DNA sample (SEQ ID NO: 33 which is attached at the 5' end to four iSpC3 spacers which are attached at the opposite end to SEQ ID NO: 30) needed for step 1.2 was produced using the following method. A 600 bp fragment of lambda (SEQ ID NO: 27 shows the sense sequence of dsDNA) was amplified using LongAmp™ Taq DNA polymerase (NEB, catalog No: M0323S) with the following primers SEQ ID NO: 28 and SEQ ID NO: 29. Reactions were cycled as follows; 94° C. for 30 secs, (94° C. for 15 secs, 57° C. for 30 secs, 65° C. for 1 min)$_{30}$, 65° C. 5 mins. The 600 bp fragment was run on a 5% TBE PAGE gel and PAGE purified, eluting in nuclease free water.

A second round of PCR was then carried out using the first round product as template, LongAmp™ Taq DNA polymerase (NEB, catalog No: M0323S) and the following primers (primer 1=SEQ ID NO: 30 is attached at its 5 end to 28 iSpC3 spacers which are attached at the opposite end to two thymines and at its 3' end to four iSpC3 spacers which are attached at the opposite end to SEQ ID NO: 31 and primer 2=SEQ ID NO: 32).

After PCR the product was then subjected to lambda exonuclease (NEB, catalog No. M0262S) digestion for 1 hour at 37° C. After digestion the product was run on a 5% TBE PAGE gel and the ssDNA purified from the gel (SEQ ID NO: 33 which is attached at the 5' end to four iSpC3 spacers which are attached at the opposite end to SEQ ID NO: 30), eluting in nuclease free water.

1.2 Preparation of Modified DNA Sample

The modified ssDNA sample was made via the following method outlined in the Table 1 and the paragraphs below. The example in the table substituted dGTP with 6-thio-2'-deoxyguanosine-5'-triphosphate, however, any of the dNTP's can be substituted for a different nucleotide species using the below procedure.

TABLE 1

| Component | Volume | Final Concentration |
|---|---|---|
| 600 bp ssDNA fragment of Lambda DNA (SEQ ID NO: 33 which is attached at the 5' end to four iSpC3 spacers which are attached at the opposite end to SEQ ID NO: 30), 500 nM | 20 µL | 100 nM |
| NEBuffer2 (10x) | 10 µL | N/A |
| DTT (100 mM) | 1 µL | 1 mM |
| dCTP, dTTP, dATP | 2 µL | 200 µM |
| 6-thio-2'-deoxyguanosine-5'-triphosphate | 2 µL | 200 µM |
| Klenow exo⁻ (SEQ ID NO: 26) | 2.5 µL | 25 U |
| nH$_2$O | 62.5 µL | N/A |

The above reaction mixture was incubated at 37° C. for 60 minutes. A 15 µL sample was added to RecJ$_f$ (purchased from New England Biolabs™) and incubated for 1 hour at 37° C. before it was run on a 5% TBE PAGE at 140 V for 55 minutes. An example of a PAGE gel is shown in FIG. 1. Lane 5 shows a gel of the modified DNA where dTTP had been replaced with 5-propynyl-2'-deoxyuridine-5'-triphosphate in the sample preparation procedure previously in table 1. Lane 6 shows a gel of the modified DNA where dGTP had been replaced with 6-thio-2'-deoxyguanosine-5'-triphosphate in the sample preparation procedure described in table 1. Lane 7 shows a gel of the modified DNA where dTTP and dGTP were replaced with 5-propynyl-2'-deoxyuridine-5'-triphosphate and 6-thio-2'-deoxyguanosine-5'-triphosphate respectively in the sample preparation procedure described previously in table 1. The band produced by the modified 600 bp fragment ran at the same position as the 600 bp control (lane 3), illustrating that the sample preparation had been successful.

The reaction mixture was then purified using SPRI beads (150 µL) and eluted in nuclease free water (40 µL). The sample was quantified using the Nanodrop and the concentration adjusted to 100 nM. The DNA sample (SEQ ID NO: 34 which is attached at the 3' end to four iSpC3 spacers which are attached at the opposite end to the 5' end of SEQ ID NO: 38 shows the non-modified sequence, where in this example all G's are substituted for 6-thio-2'-deoxyguanosine-5'-triphosphate) (100 nM) was then incubated with tether (SEQ ID NO: 42, 100 nM), 5x annealing buffer and nuclease free water and heated at 55° C. for 2 minutes and the cooled to 18° C. at 2° C. per minute.

Example 2

This example describes how a Trwc Cba (SEQ ID NO: 25) enzyme controlled the movement of modified polynucleotides through a single MspA nanopore (MS(B1-G75S/G77S/L88N/Q126R)8 MspA (MspA-B2C) (SEQ ID NO: 2 with mutations G75S/G77S/L88N/Q126R).

Materials and Methods

Prior to setting up the experiment, the modified DNA construct (SEQ ID NO: 34 which is attached at the 3' end to four iSpC3 spacers which are attached at the opposite end to the 5' end of SEQ ID NO: 38 where at least one of C, T, A or G was replaced with a different nucleotide triphosphate species in step 1.2 of Example 1; also including tether sequence SEQ ID NO: 42, final concentration 0.5 nM) and TrwC Cba (1 µM) were pre-incubated together for at least an hour at 23° C. in buffer (50 mM CAPS/NaOH, pH 10.0+100 mM NaCl).

Electrical measurements were acquired at 15° C. (by placing the experimental system on a cooler plate) from single MspA nanopores (MspA-B2C) inserted in block co-polymer in buffer (625 mM KCl, 100 mM HEPES, 75 mM Potassium Ferrocyanide (II), 25 mM Potassium ferricyanide (III), pH 8). After achieving a single pore inserted in the block co-polymer, then buffer (1 mL, 625 mM KCl, 100 mM HEPES, 75 mM Potassium Ferrocyanide (II), 25 mM Potassium ferricyanide (III), pH 8) was flowed through the system to remove any excess MspA nanopores (MspA-B2C). MgCl$_2$ (10 mM final concentration) and dTTP (5 mM final concentration) were mixed together with buffer (625 mM KCl, 100 mM HEPES, 75 mM Potassium Ferrocyanide (II), 25 mM Potassium ferricyanide (III), pH 8) and then added to the modified DNA construct (0.5 nM final concentration), TrwC Cba (1 µM final concentration) buffer (50 mM CAPS/NaOH, pH 10.0+100 mM NaCl) pre-mix. The pre-mix was then added to the single nanopore experimental system. Experiments were carried out for two hours following a potential flip process (120 mV with potential flips down of −100 mV for 2 seconds then 0 mV for 2 seconds every 20 minutes) and helicase-controlled DNA movement was monitored.

Results and Discussion

Helicase controlled DNA movement was observed for the modified DNA constructs tested (labelled construct Z in table 2 below, which corresponds to SEQ ID NO: 34 which is attached at the 3' end to four iSpC3 spacers which are attached at the opposite end to the 5' end of SEQ ID NO: 38 where at least one of C, T, A or G was replaced with a different nucleotide tri-phosphate species in step 1.2 of Example 1; also including tether sequence SEQ ID NO: 42). A list of other tested modified polynucleotides which were investigated is provided at the end of this example (for example entries 2-4 the buffer used was 600 mM KCl, 25 mM potassium phosphate, 75 mM potassium ferrocyanide (II), 25 mM potassium ferricyanide, pH 8.0 and the potential flip protocol used was 120 mV with potential flips down of −100 mV for 2 seconds then 0 mV for 2 seconds every 10 minutes). Table 2 below highlights a number of examples which were investigated.

TABLE 2

| Experiment No. | Base replaced in step 1.2 in construct Z | Modified Nucleotide tri-phosphate Species used in step 1.2 | Chemical Structure | FIG. No. |
|---|---|---|---|---|
| 1 | T | 5-propynyl-2'-deoxyuridine-5'-triphosphate | 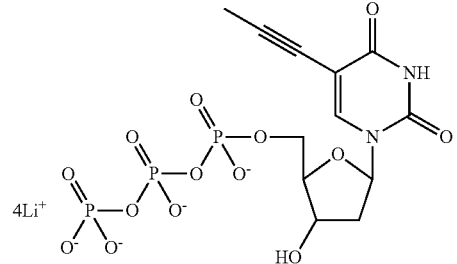 [SMILES: CC#Cc1cn(C2CC(O)C(COP(=O)([O-])OP(=O)([O-])OP(=O)([O-])[O-])O2)c(=O)[nH]c1=O] | 2 and 3 |
| 2 | A | 2'-fluoro-2'-deoxyadenosine-5'-triphosphate | 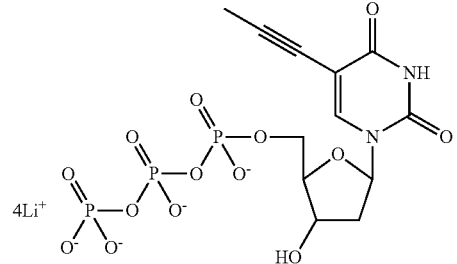 [SMILES: CC#Cc1cn(C2CC(O)C(COP(=O)([O-])OP(=O)([O-])OP(=O)([O-])[O-])O2)c(=O)[nH]c1=O] | 4 |
| 3 | A | 2-fluoro-adenosine-5'triphosphate | 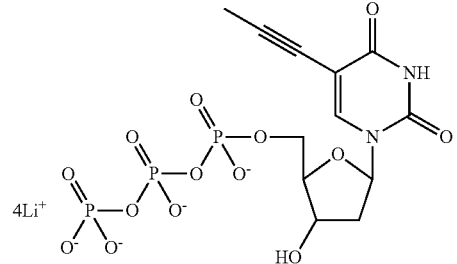 [SMILES: CC#Cc1cn(C2CC(O)C(COP(=O)([O-])OP(=O)([O-])OP(=O)([O-])[O-])O2)c(=O)[nH]c1=O] | 5 |
| 4 | G | 7-deaza-7-iodo-2'-deoxy-guanosine-5'triphosphate | 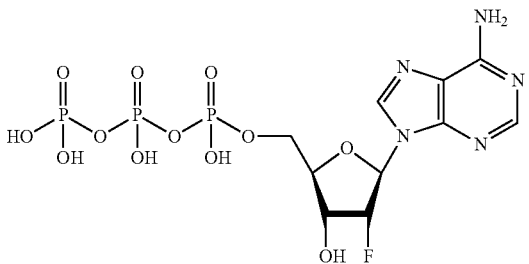 | 6 |

TABLE 2-continued

| Experiment No. | Base replaced in step 1.2 in construct Z | Modified Nucleotide tri-phosphate Species used in step 1.2 | Chemical Structure | FIG. No. |
|---|---|---|---|---|
| 5 | G | 2'-fluoro-2'deoxyguanosine-5'-triphosphate | 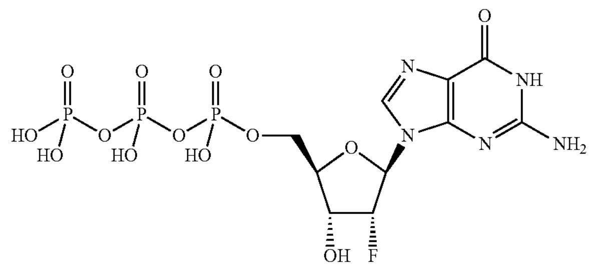 [SMILES: Nc1nc2c(ncn2[C@@H]2O[C@H](COP(=O)(O)OP(=O)(O)OP(=O)(O)O)[C@@H](O)[C@H]2F)c(=O)[nH]1] | 7 |
| 6 | C | 5-formyl-2'deoxycytidine-5'-triphosphate | 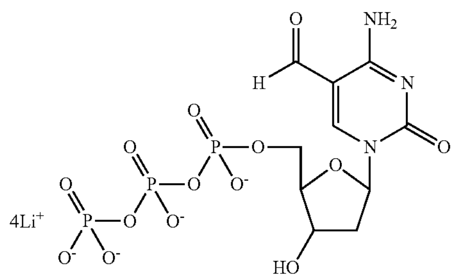 [SMILES: Nc1nc(=O)n(C2CC(O)C(COP(=O)([O-])OP(=O)([O-])OP(=O)([O-])[O-])O2)cc1C=O] | 8 |

Figure 3:
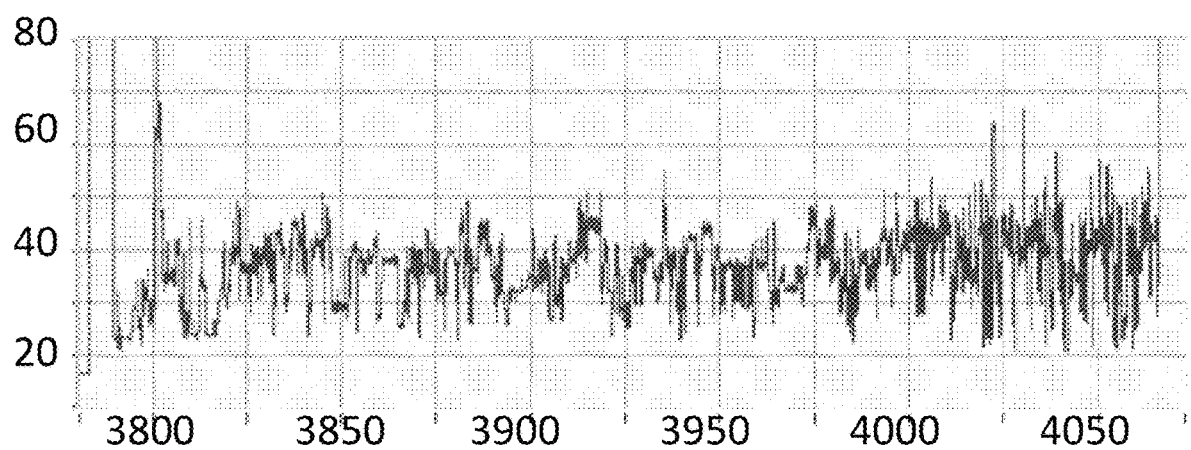
FIG. 3 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where T was replaced with 5-propynyl-2'-deoxyuridine-5'-triphosphate in step 1.2 of Example 1; also including tether sequence SEQ ID NO: 42, 0.5 nM) through a nanopore (MS(B1-G75S/G77S/L88N/Q126R)8 MspA (MspA-B2C) (SEQ ID NO: 2 with mutations G75S/G77S/L88N/Q126R)). The lower current trace is a zoomed in region of the trace above.
Figure 3:
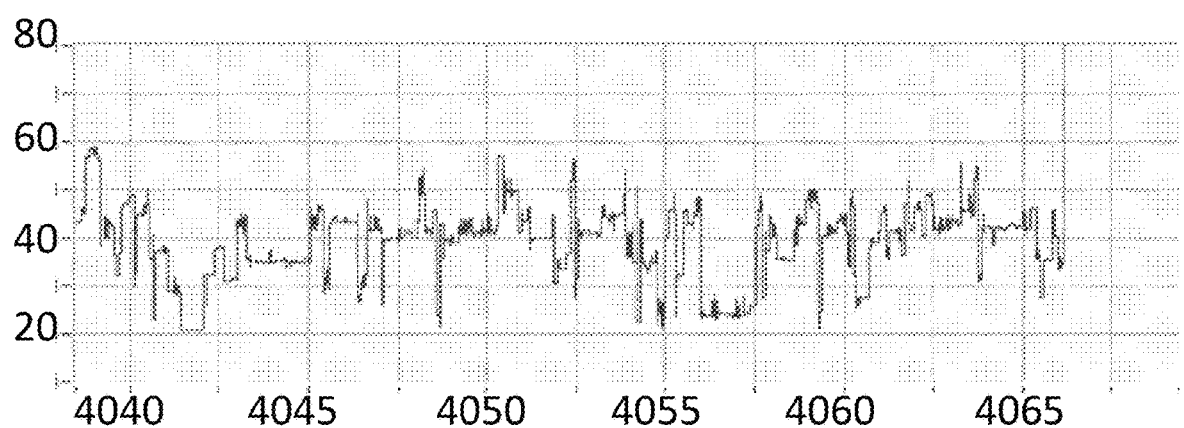
Figure 4:
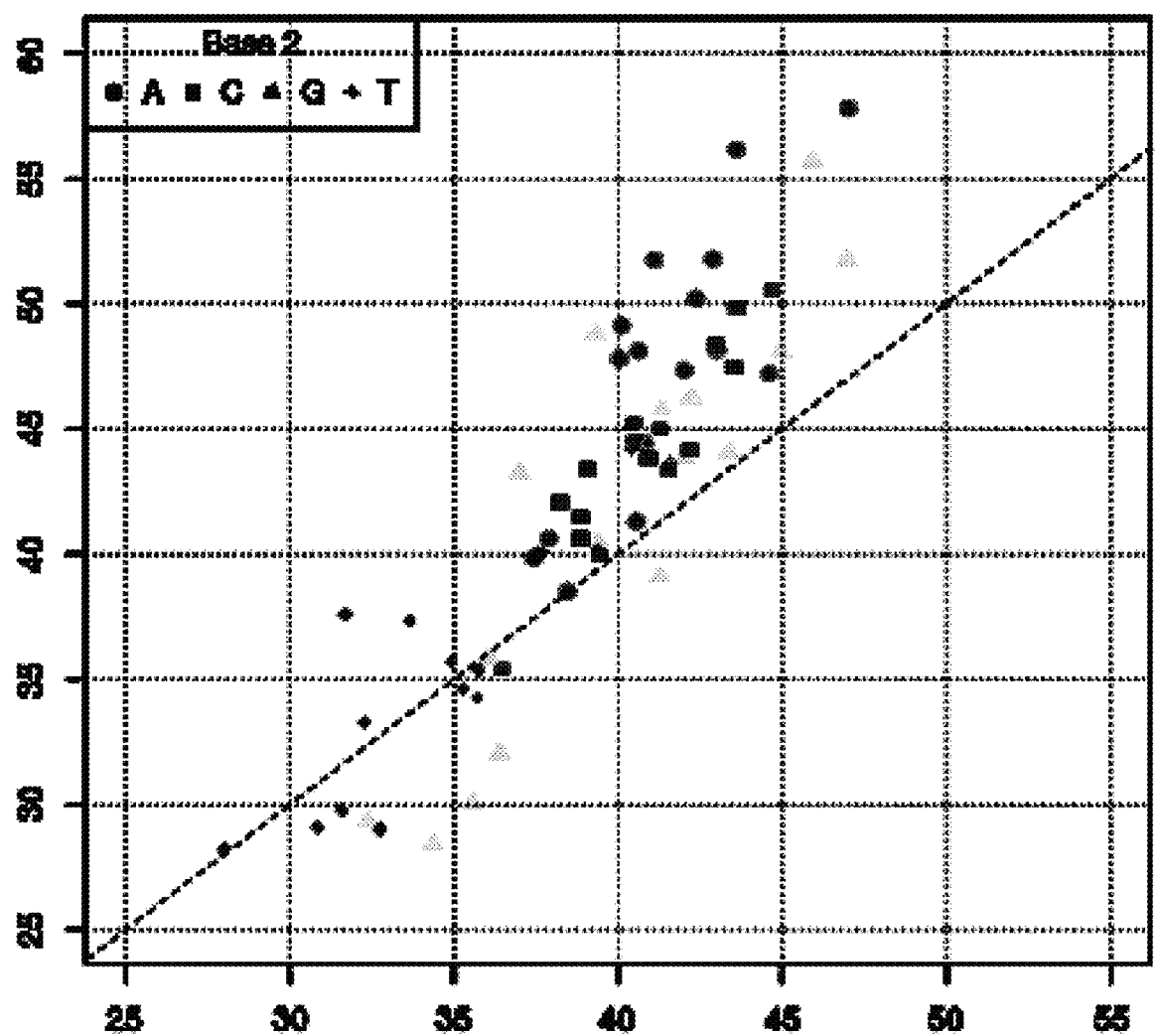
FIG. 4 shows a diagonal dot plot for the modified DNA construct which was made up of C, T, G and 2'-fluoro-2'-deoxyadenosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 5:
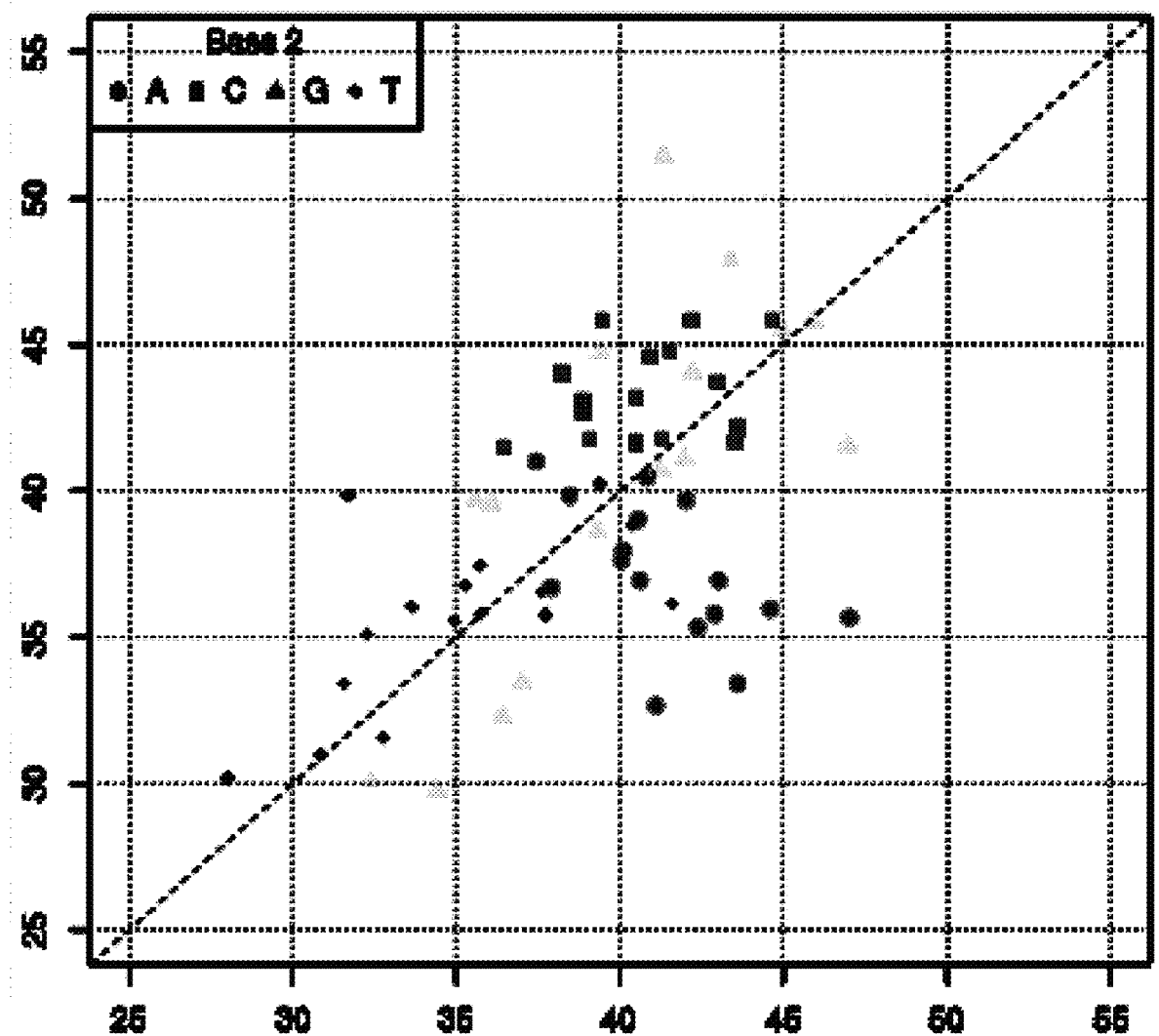
FIG. 5 shows a diagonal dot plot for the modified DNA construct which was made up of C, T, G and 2-fluoro-adenosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 6:
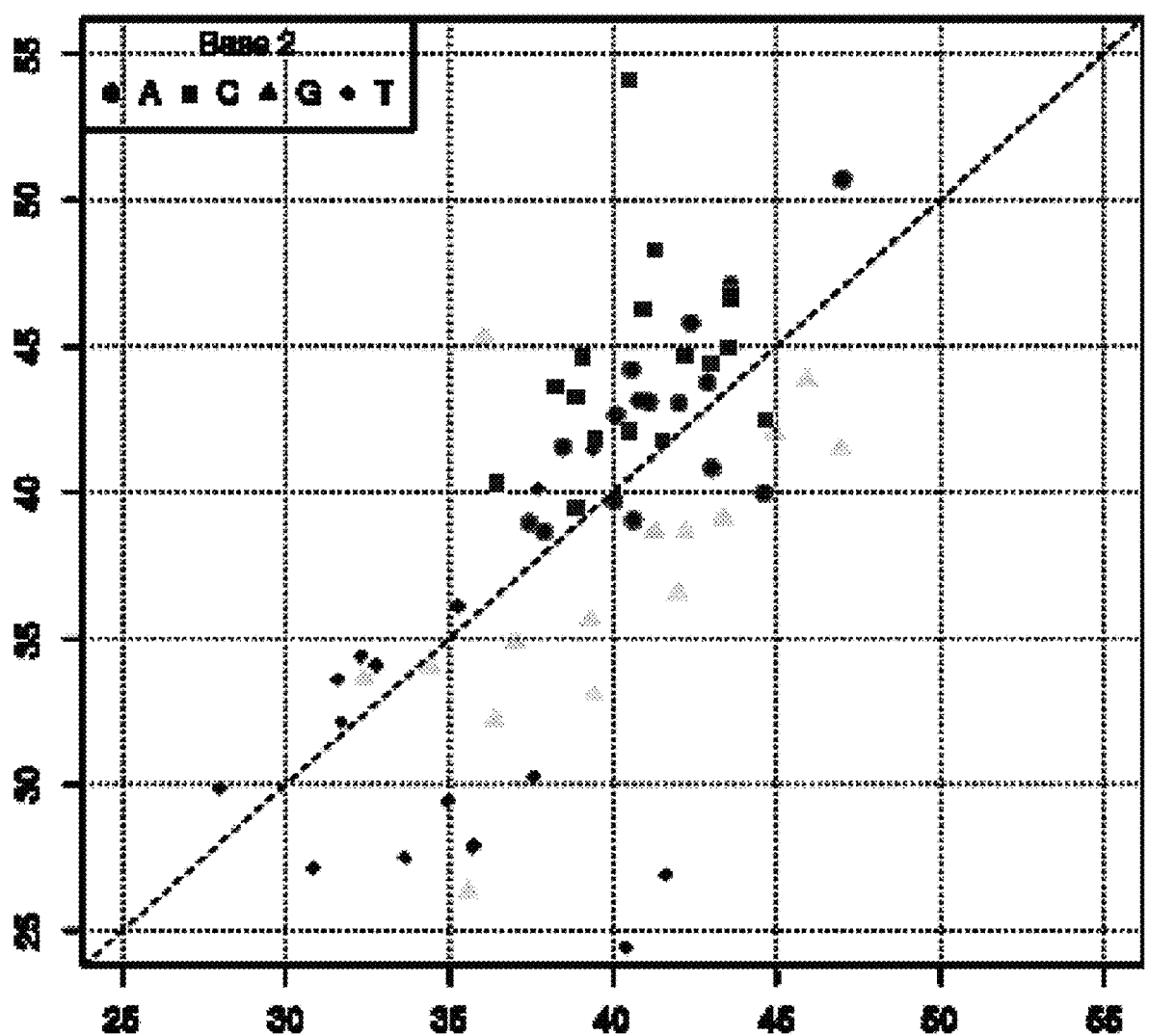
FIG. 6 shows a diagonal dot plot for the modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 7:
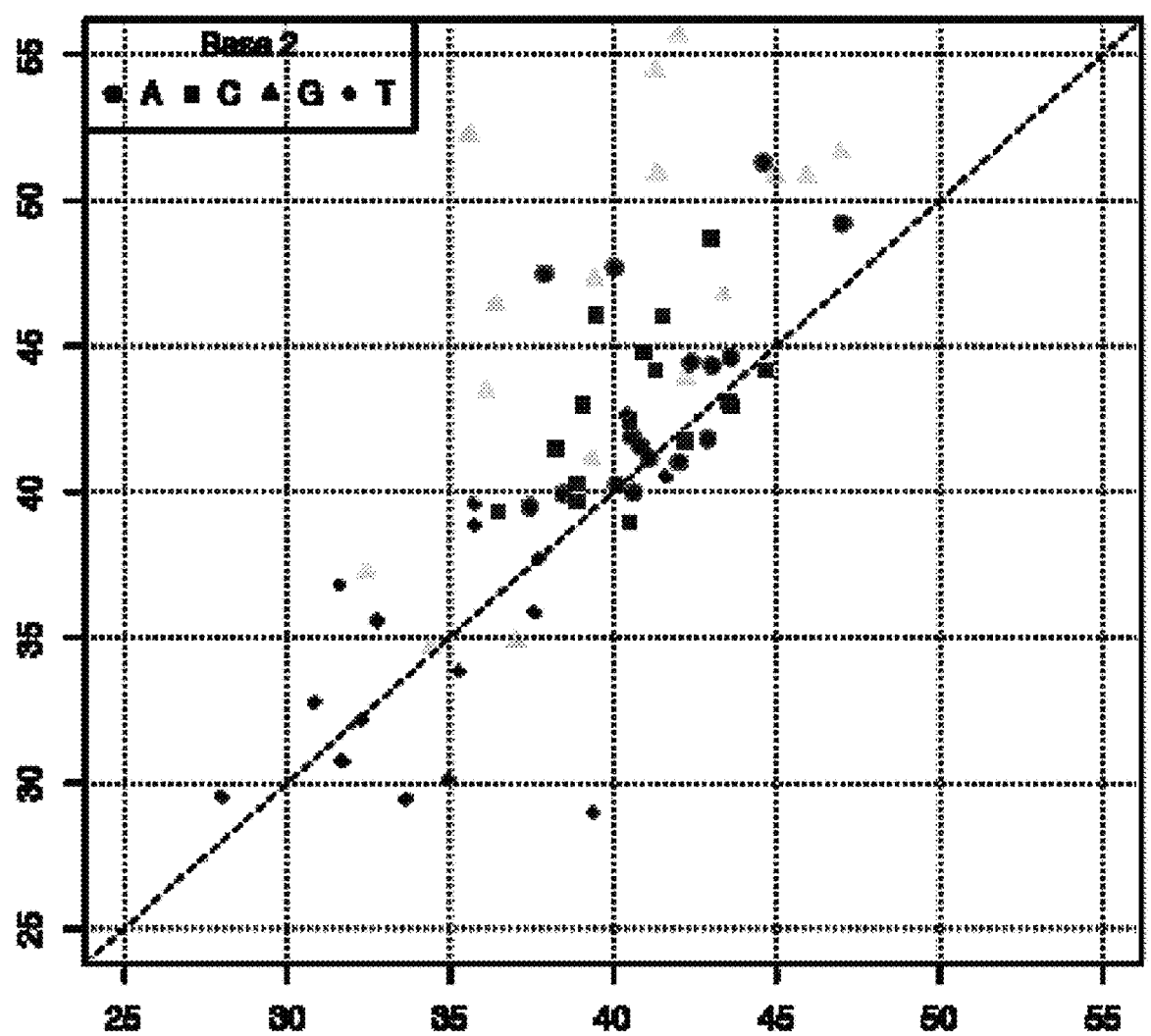
FIG. 7 shows a diagonal dot plot for the modified DNA construct which was made up of C, T, A and 2'-fluoro-2'deoxyguanosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 8:
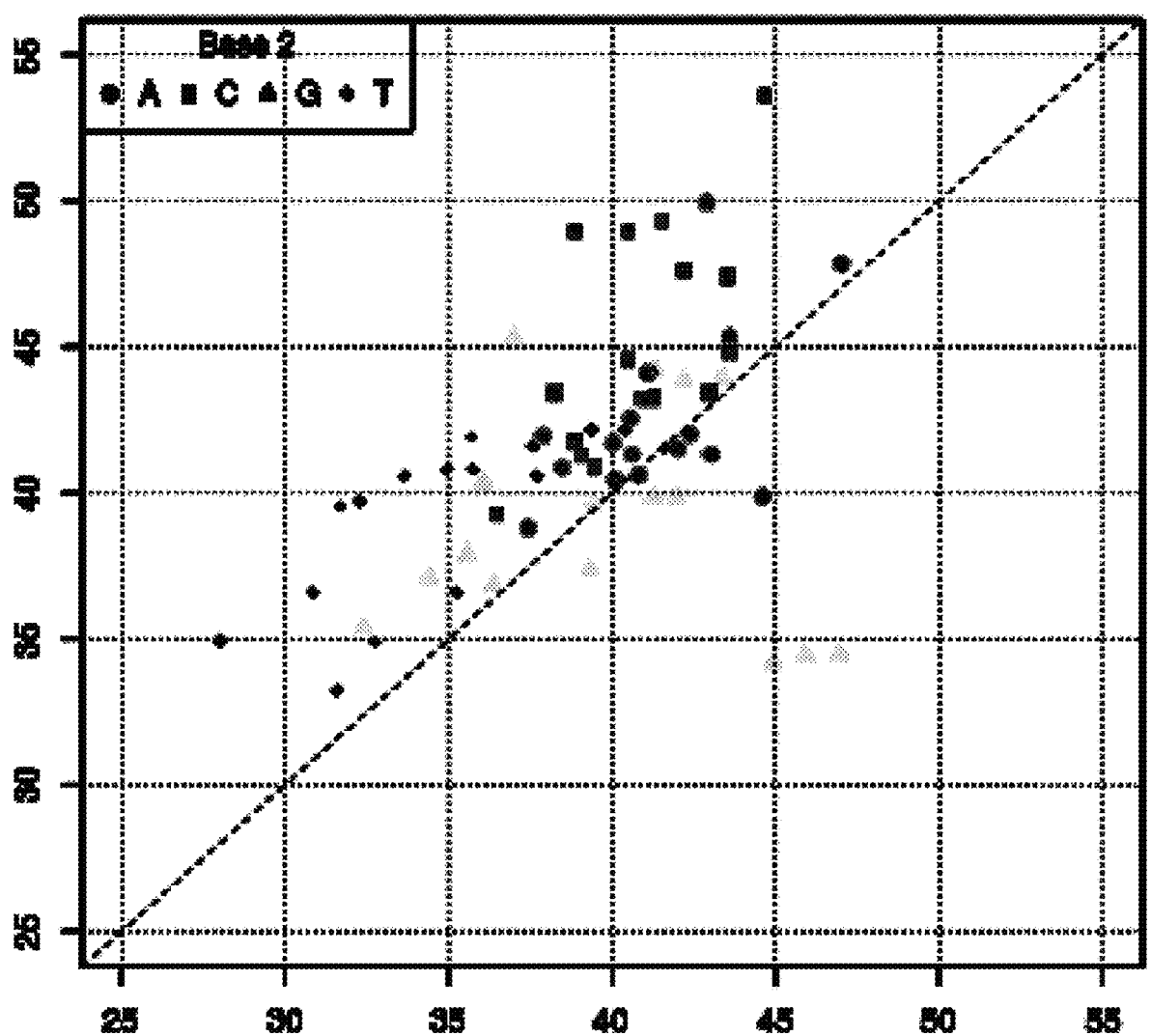
FIG. 8 shows a diagonal dot plot for the modified DNA construct which was made up of G, T, A and 5-formyl-2'deoxycytidine-5'-triphosphate. The diagonal dot plot displays the current level for each base combination in the modified strand plotted against its equivalent in an unmodified strand, such that the large changes in the current-sequence relationship are represented by large displacements from the diagonal.

The diagonal dot plots shown in FIGS. 2 and 4-8 display the current level for each base combination in the modified strand plotted against its equivalent in an unmodified strand, such that large changes in the current-sequence relationship were represented by large displacements from the diagonal. FIG. 3 shows an example of helicase controlled DNA movement for experiment number 1 in table 2.

When data from a modified template was obtained, the strands were mapped to the known sequence and used to train a new base-calling model where each "kmer" or base combination had a characteristic current level. These kmer current levels were plotted on the vertical axis, against their unmodified equivalents on the horizontal axis. The shape of the point denoted the central base of the combination. In this way the relationship between measured current signal and sequence for a particular set of modifications was described. A modified template which showed a very different current-sequence relationship showed points which moved away from the diagonal, whereas one with little change showed points arranged close to the diagonal. Depending on the specific modification(s) used, the changes observed were either due to specific sets of kmers, or a more general spread.

Modifications which demonstrated large or distinct changes from the standard model were of especial interest as they were used in combination with the standard to provide more information about the sequence. It was clear from exemplary FIGS. 2 and 4-8 that the introduction of different nucleotides species into the modified polynucleotide produced distinct changes in the standard model.

The following different nucleotide species were also tested in the same experimental system described above—5-Carboxy-2'-deoxycytidine-5'-Triphosphate, 5-Propynyl-2'-deoxycytidine-5'-Triphosphate, 5-Fluoro-2'-deoxyuridine-5'-Triphosphate, 2-Thiothymidine-5'-Triphosphate, 5-Bromo-2'-deoxycytidine-5'-Triphosphate, 5-Iodo-2'-deoxycytidine-5'-Triphosphate, 5-trifluoromethyl-2'deoxy-Uridine-5'-triphosphate, 5-Iodo-2'-deoxyuridine-5'-Triphosphate, 5-Bromo-2'-deoxyuridine-5'-Triphosphate, 7-deaza-7-bromo-2'-deoxy-adenosine-5'-triphosphate, 7-deaza-7-iodo-2'-deoxy-adenosine-5'-triphosphate, 7-deaza-7-iodo-2'-deoxy-guanosine-5'-triphosphate, 6-Thio-2'-deoxyguanosine-5'-Triphosphate, alpha-Thiophosphate-deoxythymidine-5'-triphosphate, alpha-Thiophosphate-deoxyadenosine-5'-triphosphate, 5-Fluoro-2-deoxycytidine-5'-triphosphate, 2'-fluoro-2'-deoxy-uridine-5'-triphosphate, 2'-fluoro-2-deoxyuridine-5'-triphosphate, 2'-fluoro-2'-deoxy-cytidine-5'-triphosphate.

The following different nucleotide species were also tested in an experiment similar to that described above but using a strand which was 200 bp in length (SEQ ID NO: 39 is attached at its 3' end to four iSpC3 spacers which are attached at the opposite end to the 5' end of SEQ ID NO: 40 where at least one of C, T, A or G was replaced with a different nucleotide triphosphate species in step 1.2 of Example 1; also including tether sequence SEQ ID NO: 42)-inosine (2'deoxyinosine-5'-triphosphate), 7-Deaza-2'-deoxyguanosine-5'-Triphosphate, abasic (replacing either G or T), glycosylated hydroxymethylated deoxycytidine replaced hmC post polymerase incorporation, 2'-Deoxy-P-nucleoside-5'-Triphosphate (dP), zebularine (2'deoxyebularine-5'-triphosphate), 5-Hydroxymethyl-2'-deoxyuridine-5'-Triphosphate, N4-Methyl-2'-deoxycytidine-5'-Triphosphate, 5-Methyl-2'-deoxycytidine-5'-Triphosphate, 7-Deaza-2'-deoxyadenosine-5'-Triphosphate, 2-Amino-2'-deoxyadenosine-5'-Triphosphate, N6-Methyl-2'-deoxyadenosine-5'-Triphosphate, 2-Aminopurine-2'-deoxyriboside-Triphosphate, 2'-Deoxyuridine-5'-Triphosphate, backbone of the strand changed to LNA, N6-benzyl-2'-deoxyadenosine-5'-triphosphate, 5-Amino-propargyl-2'-deoxyuridine 5'-triphosphate coupled to Cy5, 5-Propynyl-2'-deoxyuridine-5'-Triphosphate, 5-Hydroxymethyl-2'-deoxyuridine-5'-Triphosphate, 6-Aza-2'-deoxyuridine-5'-Triphosphate, 6-Thio-2'-deoxyguanosine-5'-Triphosphate, 5-Formyl-2'-deoxycytidine-5'-Triphosphate, 5-Carboxy-2'-deoxycytidine-5'-Triphosphate and 2-Thio-2'-deoxycytidine-5'-Triphosphate.

Example 3

This example describes how a Trwc Cba (SEQ ID NO: 25) enzyme controlled the movement of modified polynucleotides through a single MspA nanopore (MspA-B2C). The nucleotide species (A and G) in the template polynucleotide were replaced with different nucleotide species (7-deaza-7-iodo-2'-deoxy-adenosine-5'-triphosphate and 7-deaza-7-iodo-2'-deoxy-guanosine-5'-triphosphate) in the modified polynucleotide.

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42, final concentration 0.5 nM) was produced using different nucleotide triphosphate species (C, T, 7-deaza-7-iodo-2'-deoxy-adenosine-5'-triphosphate and 7-deaza-7-iodo-2'-deoxy-guanosine-5'-triphosphate).

The electrical measurements were acquired and helicase-controlled DNA movement monitored using the same method as described in Example 2 above except that the experimental buffer used was (600 mM KCl, 25 mM potassium phosphate, 75 mM potassium ferrocyanide, 25 mM potassium ferricyanide, pH 8.0) and a slightly different potential flip process (120 mV with potential flips down of −100 mV for 2 seconds then 0 mV for 2 seconds 10 minutes) was applied.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42). A list of other tested modified polynucleotides which were investigated is provided at the end of this example.

Figure 9:
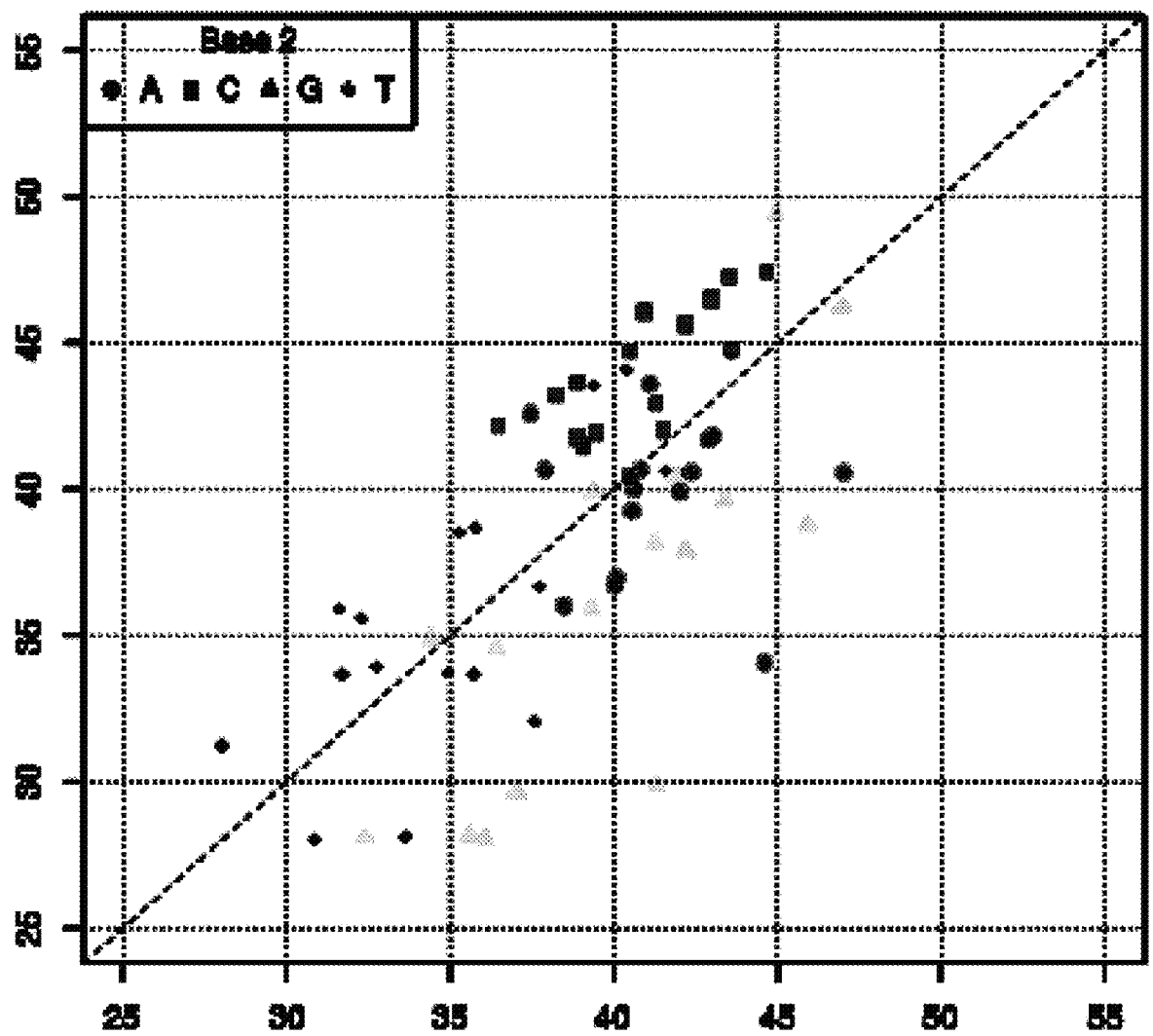
FIG. 9 shows a diagonal dot plot for the modified DNA construct which was made up of C, T, 7-deaza-7-iodo-2'-deoxy-adenosine-5'-triphosphate and 7-deaza-7-iodo-2'-deoxy-guanosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 10:
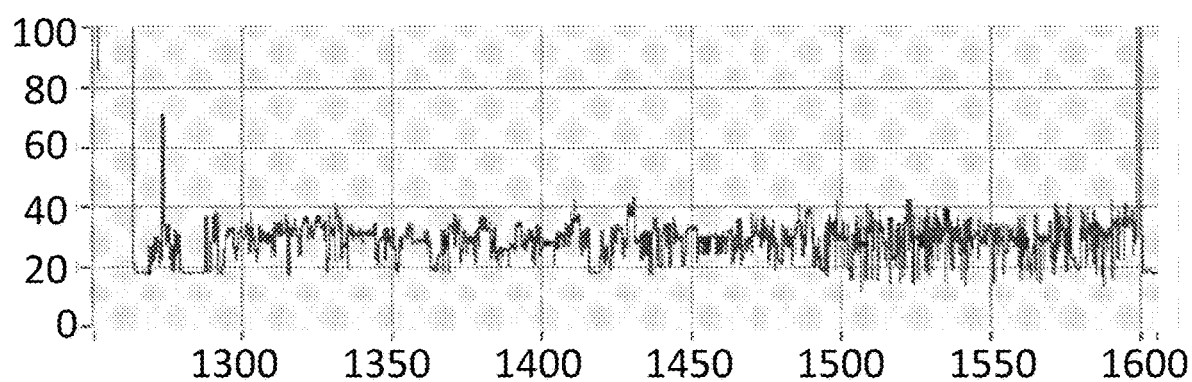
FIG. 10 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42, 0.5 nM) through a nanopore (MspA-B2C). The lower current trace is a zoomed in region of the trace above.
Figure 10:
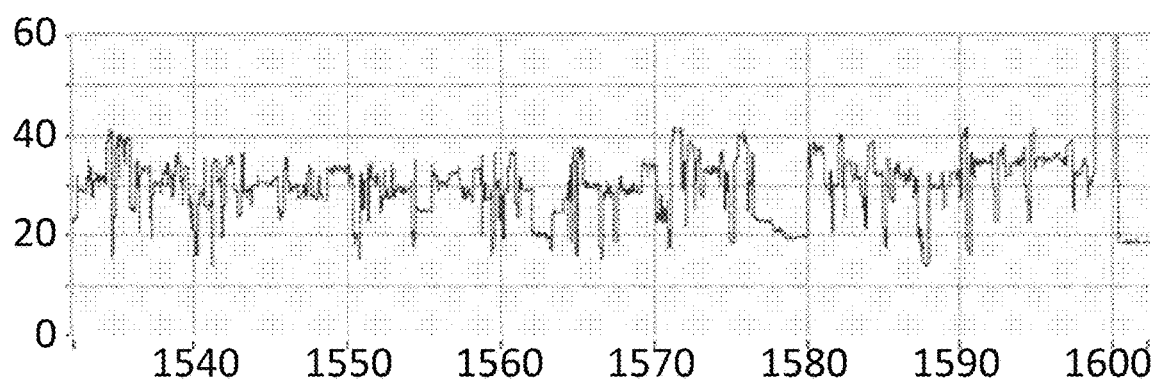

The diagonal dot plot shown in FIG. 9 displays the current level for each base combination in the modified strand plotted against its equivalent in an unmodified strand, such that large changes in the current-sequence relationship were represented by large displacements from the diagonal. FIG. 10 shows an example of helicase controlled DNA movement of the modified strand (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42).

The modifications tested in this example (7-deaza-7-iodo-2'-deoxy-adenosine-5'-triphosphate and 7-deaza-7-iodo-2'-deoxy-guanosine-5'-triphosphate) demonstrated that distinct changes from the standard model (see FIG. 9) were observed when more than one nucleotide species was replaced with a different nucleotide species.

The following different nucleotide species combinations were also tested in the same experimental system described above—(5-Propynyl-2'-deoxycytidine-5'-Triphosphate and 5-Propynyl-2'-deoxyuridine-5'-Triphosphate), (5-Propynyl-2'-deoxyuridine-5'-Triphosphate and 5-Carboxy-2'-deoxycytidine-5'-Triphosphate), (5-Propynyl-2'-deoxyuridine-5'-Triphosphate and 7-Deaza-2'-deoxyguanosine-5'-Triphosphate), (5-Propynyl-2'-deoxyuridine-5'-Triphosphate and 5-Formyl-2'-deoxycytidine-5'-Triphosphate), (5-Propynyl-2'-deoxycytidine-5'-Triphosphate and 2-Amino-2'-deoxyadenosine-5'-Triphosphate), (2'-fluoro-2'-deoxyadenosine-5'-triphosphate and 5-trifluoromethyl-2' deoxy-Uridine-5'-triphosphate), (5-Propynyl-2'-deoxyuridine-5'-Triphosphate and 2'-fluoro-2'-deoxyadenosine-5'-triphosphate), (2'-fluoro-2'-deoxyadenosine-5'-triphosphate and 7-deaza-7-iodo-2-deoxyguanosine-5'-triphosphate), (5-Iodo-2'-deoxycytidine-5'-Triphosphate and 7-deaza-7-iodo-2-deoxyguanosine-5'-triphosphate), (5-Fluoro-2-deoxycytidine-5'-triphosphate and 7-deaza-7-iodo-2-deoxyguanosine-5'-triphosphate), (5-Fluoro-2-deoxycytidine-5'-triphosphate and 5-Iodo-2'-deoxyuridine-5'-Triphosphate), (5-Fluoro-2-deoxycytidine-5'-triphosphate and 5-Propynyl-2'-deoxyuridine-5'-Triphosphate), (2-fluoro-adenosine-5'-triphosphate and 5-Iodo-2'-deoxyuridine-5'-Triphosphate), (2'-fluoro-2'-deoxyadenosine-5'-triphosphate and 5-Iodo-2'-deoxyuridine-5'-Triphosphate), (2-fluoro-adenosine-5'-triphosphate and 5-Propynyl-2'-deoxyuridine-5'-Triphosphate), (5-Propynyl-2'-deoxyuridine-5'-Triphosphate and 7-deaza-7-iodo-2-deoxyguanosine), (5-Iodo-2'-deoxyuridine-5'-Triphosphate and 7-deaza-7-iodo-2-deoxyguanosine-5'-triphosphate), (5-Bromo-2'-deoxyuridine-5'-Triphosphate and 7-deaza-7-iodo-2-deoxyguanosine-5'-triphosphate), (2-fluoro-adenosine-5'-triphosphate and 5-Bromo-2'-deoxyuridine-5'-Triphosphate), (2'-fluoro-2'deoxyguanosine-5'-triphosphate and 5-Bromo-2'-deoxyuridine-5'-Triphosphate), (2'-fluoro-2'deoxyguanosine-5'-triphosphate and 5-Iodo-2'-deoxyuridine-5'-Triphosphate), (2'-fluoro-2'deoxyguanosine-5'-triphosphate and 2-fluoro-adenosine-5'-triphosphate), (2'-fluoro-2'deoxyguanosine-5'-triphosphate and 5-Bromo-2'-deoxyuridine-5'-Triphosphate) and (2'-fluoro-2'deoxyguanosine-5'-triphosphate and 5-Iodo-2'-deoxyuridine-5'-Triphosphate).

Example 4

This example describes how a Trwc Cba (SEQ ID NO: 25) enzyme controlled the movement of modified polynucleotides through a single MspA nanopore (MspA-B2C). The nucleotide species (C, T and A) in the template polynucleotide were replaced with different nucleotide species (5-Propynyl-2'-deoxycytidine-5'-Triphosphate, 5-propynyl-2'-deoxyuridine-5'-triphosphate and 2-aminopurine-2'-deoxyriboside-triphosphate).

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where C, T and A were replaced with 5-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42, final concentration 0.5 nM) was produced using different nucleotide species (7-deaza-7-iodo-2'-deoxy-adenosine-5'-triphosphate and 7-deaza-7-iodo-2'-deoxy-guanosine-5'-triphosphate).

The electrical measurements were acquired and helicase-controlled DNA movement monitored using the same method as described in Example 2 above except that the experimental buffer used was (600 mM KCl, 25 mM potassium phosphate, 75 mM potassium ferrocyanide, 25 mM potassium ferricyanide, pH 8.0) and a slightly different potential flip process (120 mV with potential flips down of −100 mV for 2 seconds then 0 mV for 2 seconds 10 minutes) was applied.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where C, T and A were replaced with 5-Propynyl-2'-deoxy-cytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42). A list of other tested modified polynucleotides which were investigated is provided at the end of this example.

Figure 11:
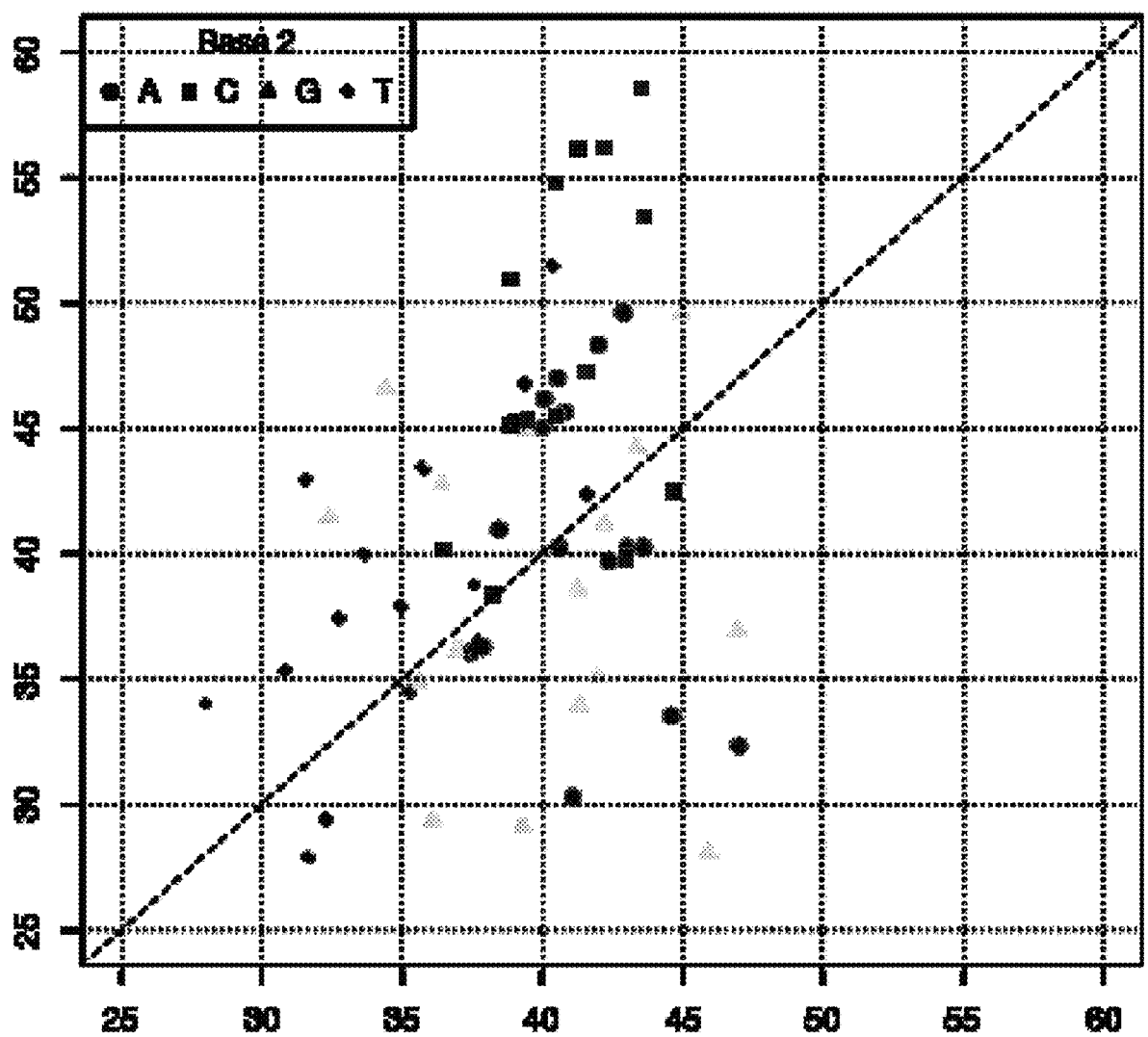
FIG. 11 shows a diagonal dot plot for the modified DNA construct which was made up of G, 5-Propynyl-2'-deoxycytidine-5'-Triphosphate, 5-propynyl-2'-deoxyuridine-5'-triphosphate and 2-aminopurine-2'-deoxyriboside-triphosphate. The diagonal dot plot displays the current level for each base combination in the modified strand plotted against its equivalent in an unmodified strand, such that the large changes in the current-sequence relationship are represented by large displacements from the diagonal.
Figure 12:
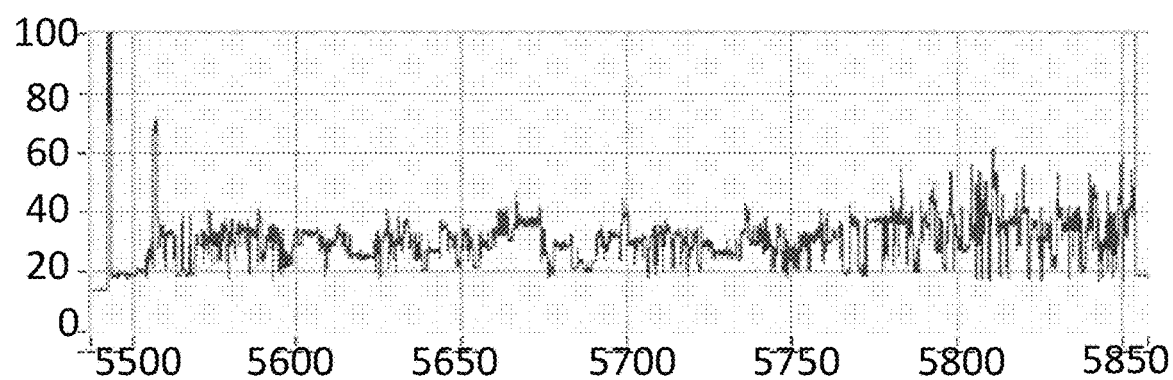
FIG. 12 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where C, T and A were replaced with 5-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42, 0.5 nM) through a nanopore (MspA-B2C). The lower current trace is a zoomed in region of the trace above.
Figure 12:
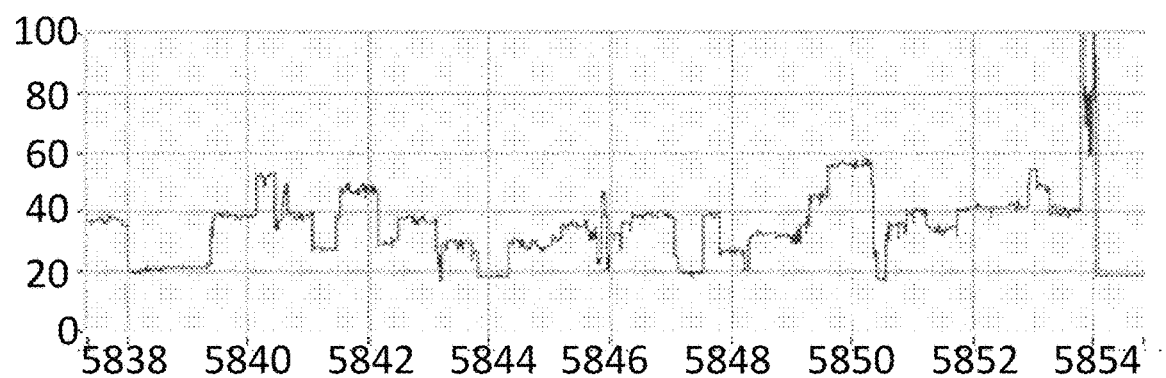

The diagonal dot plot shown in FIG. 11 displays the current level for each base combination in the modified strand plotted against its equivalent in an unmodified strand, such that large changes in the current-sequence relationship were represented by large displacements from the diagonal. FIG. 12 shows an example of helicase controlled DNA movement of the modified strand (SEQ ID NO: 34 which is attached at the 3' end to four iSpC3 spacers which are attached at the opposite end to the 5' end of SEQ ID NO: 38 where A and G were replaced with 75-Propynyl-2'-deoxy-cytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42).

The modifications tested in this example (5-Propynyl-2'-deoxycytidine-5'-Triphosphate, 5-propynyl-2'-deoxyuridine-5'-triphosphate and 2-aminopurine-2'-deoxyriboside-triphosphate) demonstrated that distinct changes from the standard model (as was clear from FIG. 11) were observed when more than one nucleotide species was replaced with a different nucleotide species.

The following different nucleotide species combinations were also tested in the same experimental system described above—(2'-fluoro-2'-deoxyadenosine-5'-triphosphate, 5-Iodo-2'-deoxyuridine-5'-Triphosphate and 7-deaza-7-iodo-2-deoxyguanosine-5'-triphosphate), (2-fluoro-adenosine-5'-triphosphate, 5-Propynyl-2'-deoxyuridine-5'-Triphosphate and 7-deaza-7-iodo-2-deoxyguanosine-5'-triphosphate) and (2'-fluoro-2'-deoxyadenosine-5'-triphosphate, 5-Propynyl-2'-deoxyuridine-5'-Triphosphate and 7-deaza-7-iodo-2-deoxyguanosine-5'-triphosphate).

Example 5

This example describes how a Trwc Cba (SEQ ID NO: 25) enzyme controlled the movement of modified polynucleotides through a single MspA nanopore MspA MS(B1-G75S/G77S/L88N/D90Q/D91Q/Q126R) (MS-QQ) (SEQ ID NO: 2 with mutations G75S/G77S/L88N/D90Q/D91Q/Q126R). The nucleotide species (G) in the template polynucleotide was replaced with a different nucleotide triphosphate species (7-deaza-7-iodo-2'-deoxy-guanosine-5'triphosphate) in the modified polynucleotide.

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where G has been replaced with 7-deaza-7-iodo-2'-deoxy-guanosine-5'triphosphate in step 1.2 of Example 1; also including tether sequence SEQ ID NO: 42) was produced using different nucleotide species (7-deaza-7-iodo-2'-deoxy-guanosine-5'triphosphate) and was used at a lower concentration (0.25 nM final concentration).

The electrical measurements were acquired and helicase-controlled DNA movement monitored using the same method as described in Example 2 above.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where G has been replaced with 7-deaza-7-iodo-2'-deoxy-guanosine-5'triphosphate in step 1.2 of Example 1; also including tether sequence SEQ ID NO: 42).

Figure 13:
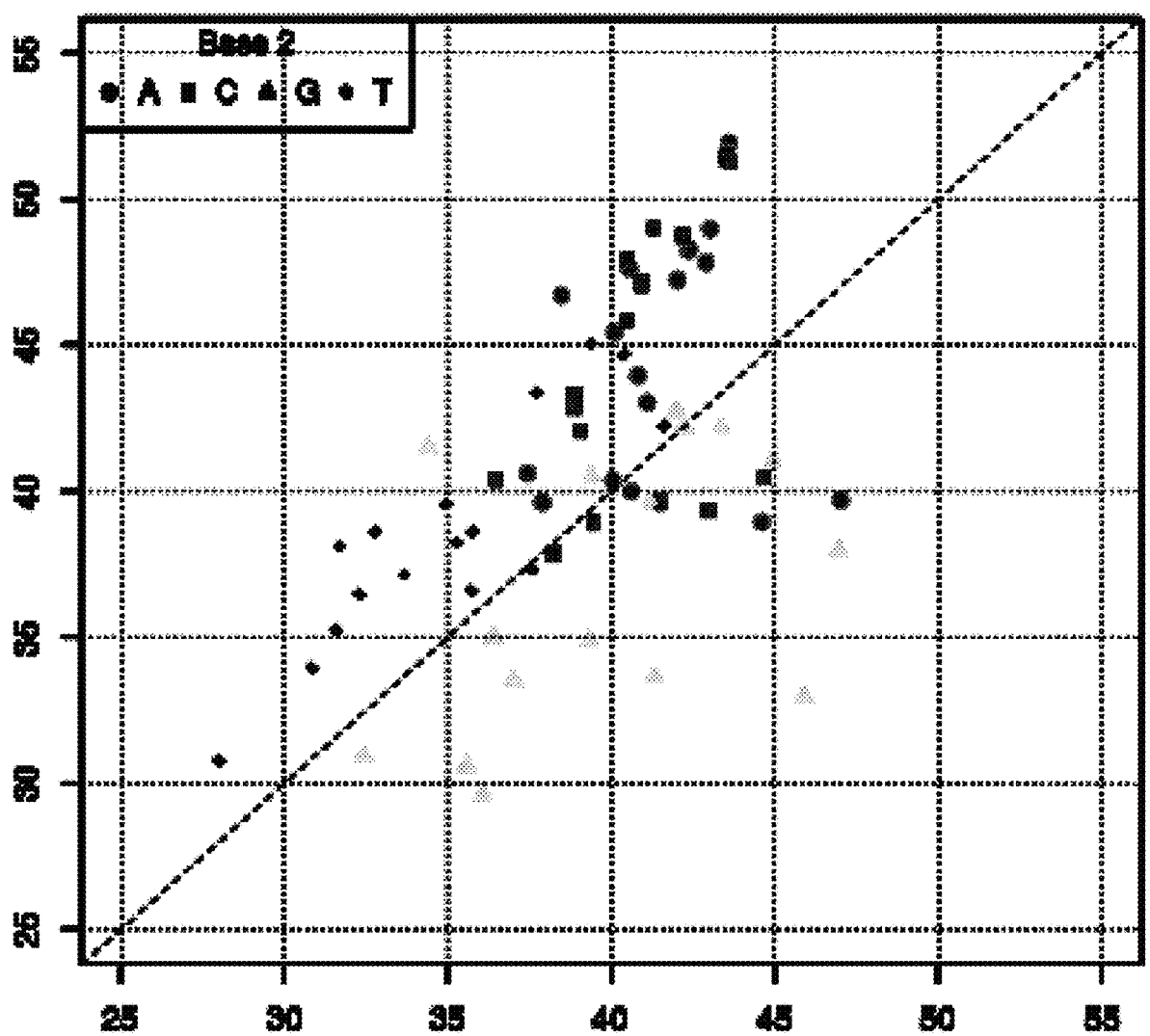
FIG. 13 shows a diagonal dot plot for the modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 14:
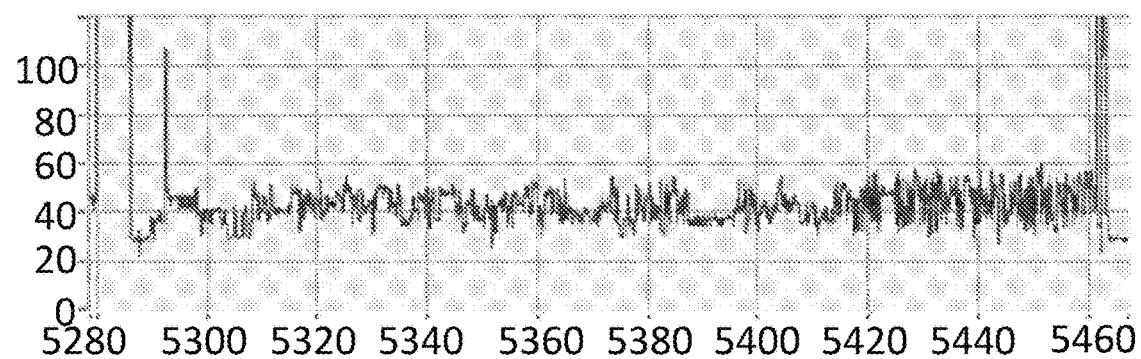
FIG. 14 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where G was replaced with 7-deaza-7-iodo-2'-deoxy-guanosine-5'triphosphate in step 1.2 of Example 1; also including tether sequence SEQ ID NO: 42, 0.5 nM) through a nanopore (MspA MS(B1-G75S/G77S/L88N/D90Q/D91Q/Q126R (MS-QQ) SEQ ID NO: 2 with mutations G75S/G77S/L88N/D90Q/D91Q/Q126R). The lower current trace is a zoomed in region of the trace above.
Figure 14:

The diagonal dot plot shown in FIG. 13 displays the current level for each base combination in the modified strand plotted against its equivalent in an unmodified strand, such that large changes in the current-sequence relationship were represented by large displacements from the diagonal. FIG. 14 shows an example of helicase controlled DNA movement of the modified strand (SEQ ID NO: 34 which is attached at the 3' end to four iSpC3 spacers which are attached at the opposite end to the 5' end of SEQ ID NO: 38 where G was replaced with 7-deaza-7-iodo-2'-deoxy-guanosine-5'triphosphate in step 1.2 of Example 1; also including tether sequence SEQ ID NO: 42). This example illustrated that it was also possible to observe distinct changes when compared to the standard model when a different mutant nanopore was used (MS-QQ) in this instance).

Example 6

This example describes how a T4 Dda-E94C/A360C (SEQ ID NO: 24 with mutations E94C/A360C) enzyme controlled the movement of a 3.6 kB strand of modified polynucleotide through a single MspA nanopore (MspA-B2C). The nucleotide species (G) in the template polynucleotide X (described below) was replaced with a different nucleotide species (7-deaza-7-iodo-2'-deoxy-guanosine-5'triphosphate) in the modified polynucleotide. This experiment was also repeated when the different nucleotide species were either 1) 5-carboxy-2'-deoxycytidine-5'triphosphate used with dATP/dGTP/dTTP or 2) 2-fluoro-adenosine-5'triphosphate used with dCTP/dGTP/dTTP.

Materials and Methods

A modified base copy of the original template and complement ~3,600 bp dsDNA fragment of Lambda DNA sample (template strand=30 iSpC3 spacers attached to the 5' end of SEQ ID NO: 45 which is attached at the 3' end to four iSp18 spacers which are attached at the opposite end to the 5' end of SEQ ID NO: 36 which is attached at the 3' end to four 5-nitroindoles which are attached at the opposite end to the 5' end of SEQ ID NO:37 and the complement strand=30 iSpC3 spacers attached to the 5' end of SEQ ID NO: 45 which is attached at the 3' end to four iSp18 spacers which are attached at the opposite end to the 5' end of SEQ ID NO: 36 which is attached at the 3' end to four 5-nitroindoles which are attached at the opposite end to the 5' end of SEQ ID NO:47) needed for 5 mer model generation was produced using the following method.

A 3447 bp fragment of lambda (SEQ ID NO: 35 shows the sense sequence of dsDNA) was amplified using LongAmp™ Taq DNA polymerase (NEB, catalog No: M0323S) with the following primers (SEQ ID NO: 48 and SEQ ID NO: 49). Reactions were cycled as follows; 94° C. for 30 secs, (94° C. for 15 secs, 57° C. for 30 secs, 65° C. for 3 min)30, 65° C. 10 mins. The 3.6 kb fragment was run on a 0.8% TAE agarose gel and gel purified, eluting in nuclease free water.

A second round of PCR was then carried out using the first round product as the template (polynucleotide X). Each reaction contained the following (final concentrations in the 10 ul reaction are given in brackets); ThermoPol Buffer (1×), 3.6 kb Template (polynucleotide X, 5 ng ul$^{-1}$), primer 1 (200 nM, 30 iSpC3 spacers attached at one end to the 5' end of SEQ ID NO:45 which is attached at its 3' end to four iSp18 spacers which are attached at the opposite end to the 5' end of SEQ ID NO: 36 which is attached at the 3' end to four 5-nitroindoles which are attached at the opposite end to the 5' end of SEQ ID NO: 31) and primer 2 (200 nM, 30 iSpC3 spacers attached at one end to the 5' end of SEQ ID NO: 45 which is attached at its 3' end to four iSp18 spacers which are attached at the opposite end to the 5' end of SEQ ID NO: 36 which is attached at the 3' end to four 5-nitroindoles which are attached at the opposite end to the 5' end of SEQ ID NO: 46), 0.2 mM of modified base triphosphate/s (7-deaza-7-iodo-2'-deoxy-guanosine-5'triphosphate or 5-carboxy-2'-deoxycytidine-5'triphosphate or 2-fluoro-adenosine-5'triphosphate depending on the experiment), 0.2 mM of the remaining dNTP/s and 1 U of Polymerase (usually 9° N unless using dUTP when used Taq). The mixture was then mixed well by pipetting and the tube was transferred to a PCR block and cycled; 95° C. for 2 mins, 56° C. for 20 secs, 72° C. for 30 mins. The sample was then 0.7×SPRI purified, washed twice in 200 ul 70% EtOH and eluted in 5 ul nH$_2$O. 5× binding buffer+EDTA (1.5 ul, 1×=25 mM potassium phosphate buffer pH 7.5, 150 mM KCl and 1 mM EDTA) and a DNA tether (1 ul of 500 nM, SEQ ID NO: 42 which is attached at its 3' end to six iSp18 spacers attached at the opposite end to two T's and 3' cholesterol TEG) were added to the sample and it was incubated at room temp for 15 mins. T4 Dda-E94C/A360C (SEQ ID NO: 24 with mutations E94C/A360C, 0.6 ul) was added and the mixture incubated at room temperature for 10 mins. TMAD (1 μL, 0.8 mM) was then added and the sample incubated at room temperature for a further 10 mins. Finally, 500 mM KCl pH 8.0, 25 mM potassium phosphate buffer (300 ul) with MgCl2 (1 mM) and rATP (2 mM) was added.

Electrical measurements were acquired at 20° C. (by placing the experimental system on a cooler plate) from single MspA nanopores (MspA-B2C) inserted in block co-polymer in buffer (600 mM KCl, 25 mM K Phosphate buffer, 75 mM Potassium Ferrocyanide (II), 25 mM Potassium Ferricyanide (III), pH 8). After achieving a single pore inserted in the block co-polymer, then buffer (3 mL, 960 mM KCl, 3 mM Potassium Ferrocyanide (II), 1 mM Potassium ferricyanide (III), 25 mM potassium phosphate pH 8) was flowed through the system to remove any excess MspA nanopores (MspA-B2C). The pre-mix as described above was then added to the single nanopore experimental system. The experiment where G was replaced with the modified base 7-deaza-7-iodo-2'-deoxy-guanosine-5'triphosphate was carried out for two hours following a potential flip process (120 mV with potential flips down of −100 mV for 2 seconds then 0 mV for 2 seconds every 60 minutes) and helicase-controlled DNA movement was monitored. The experiments where the different nucleotide species were either 1) 5-carboxy-2'-deoxycytidine-5'triphosphate used with dATP/dGTP/dTTP or 2) 2-fluoro-adenosine-5'triphosphate used with dCTP/dGTP/dTTP were run at 140 mV for 6 hours and again helicase-controlled DNA movement was monitored.

Results and Discussion

Helicase controlled DNA movement was observed for the 3.6 kB modified DNA constructs tested.

Figure 15:
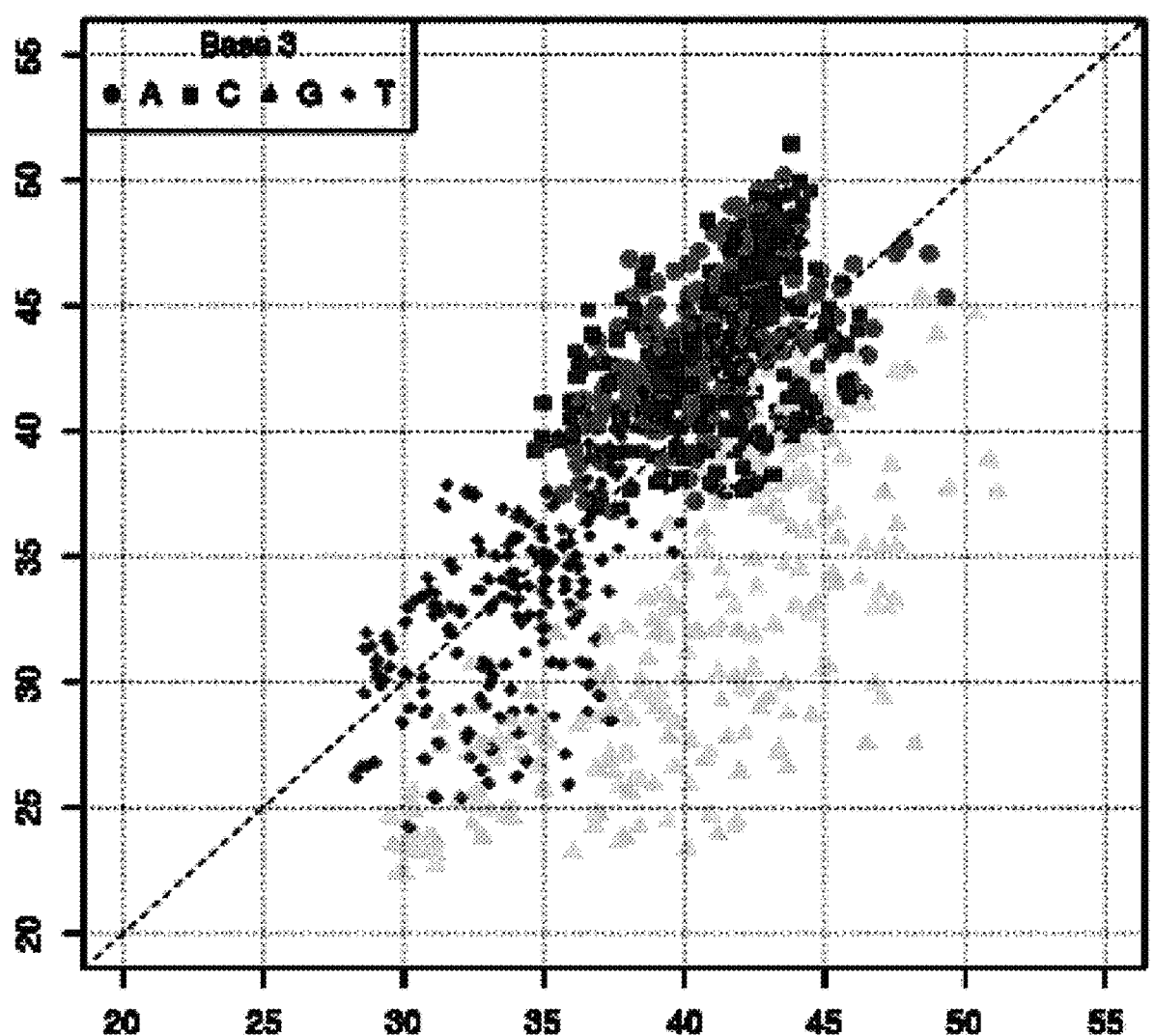
FIG. 15 shows a diagonal dot plot for the 3.6 kB modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.
Figure 16:
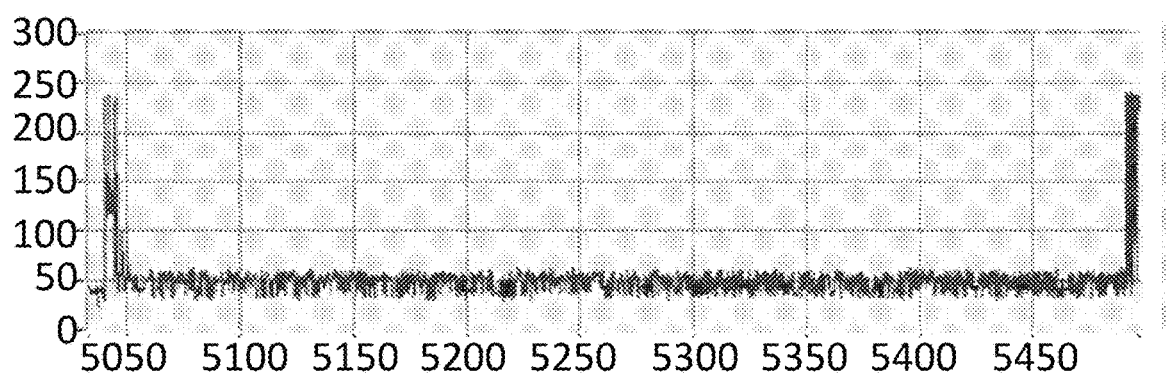
FIG. 16 shows an example current trace (y-axis label=Current (pA), x-axis label=Time (s)) of when a helicase (T4 Dda-E94C/A360C (SEQ ID NO: 24 with mutations E94C and A360C) controlled the translocation of the modified DNA construct (SEQ ID NO: 35 which is attached at its 3' end by four iSpC3 spacers which are attached at the opposite end to the 5' end SEQ NO: 36; the 3' end of SEQ ID NO: 36 is attached to an additional four iSpC3 spacers which are attached at the opposite end to the 5' end of SEQ ID NO: 37 where during synthesis all the G's in these sequences are replaced with 7-deaza-7-iodo-2'-deoxy-guanosine-5'triphosphate; also including tether sequence SEQ ID NO: 42, 0.2 nM) through a nanopore (MspA-B2C). The lower current trace is a zoomed in region of the trace above.
Figure 16:
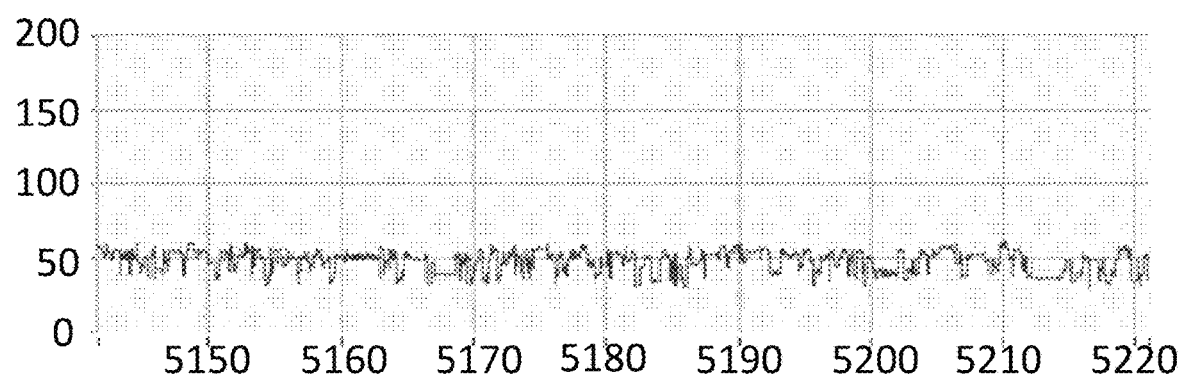

The diagonal dot plot shown in FIG. 15 displays the current level for each base combination in the modified strand plotted against its equivalent in an unmodified strand, such that large changes in the current-sequence relationship were represented by large displacements from the diagonal. FIG. 15 shows a similar plot to that previously described where the kmer positions in the new strand were plotted against their equivalents in the old strand. However, this time k=5 instead of k=3; because there are so many more 5mer combinations possible than 3mer combinations, more points are shown on the graph. A 5mer model gave a more precise fit to the current levels found in each strand event, but can only be built in longer strands where there were sufficient bases such that most combinations were found at least once in the sequence. FIG. 16 shows an example of helicase controlled DNA movement of the modified strand. This example illustrated that it was possible to observe distinct changes when compared to the standard model when a 3.6 kB modified strand was used.

Helicase controlled DNA movement was also observed for the 3.6 kB modified DNA which was produced using the nucleotide combinations of either 1) 5-carboxy-2'-deoxycytidine-5'triphosphate used with dATP/dGTP/dTTP or 2) 2-fluoro-adenosine-5'triphosphate used with dCTP/dGTP/dTTP.

Figure 19:
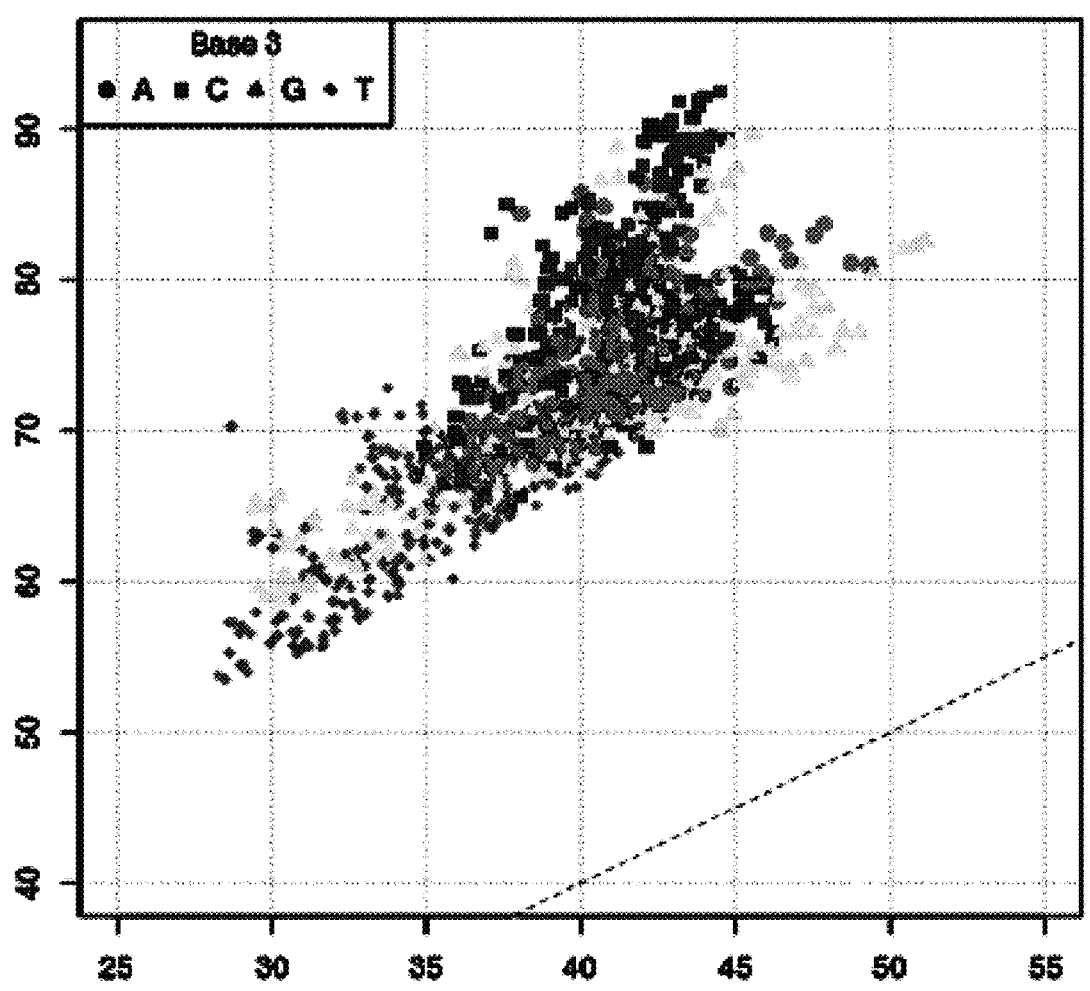
FIG. 19 shows a diagonal dot plot for the 3.6 kB modified DNA construct which was made up of A, T, G and 5-carboxy-2'-deoxycytidine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.
Figure 20:
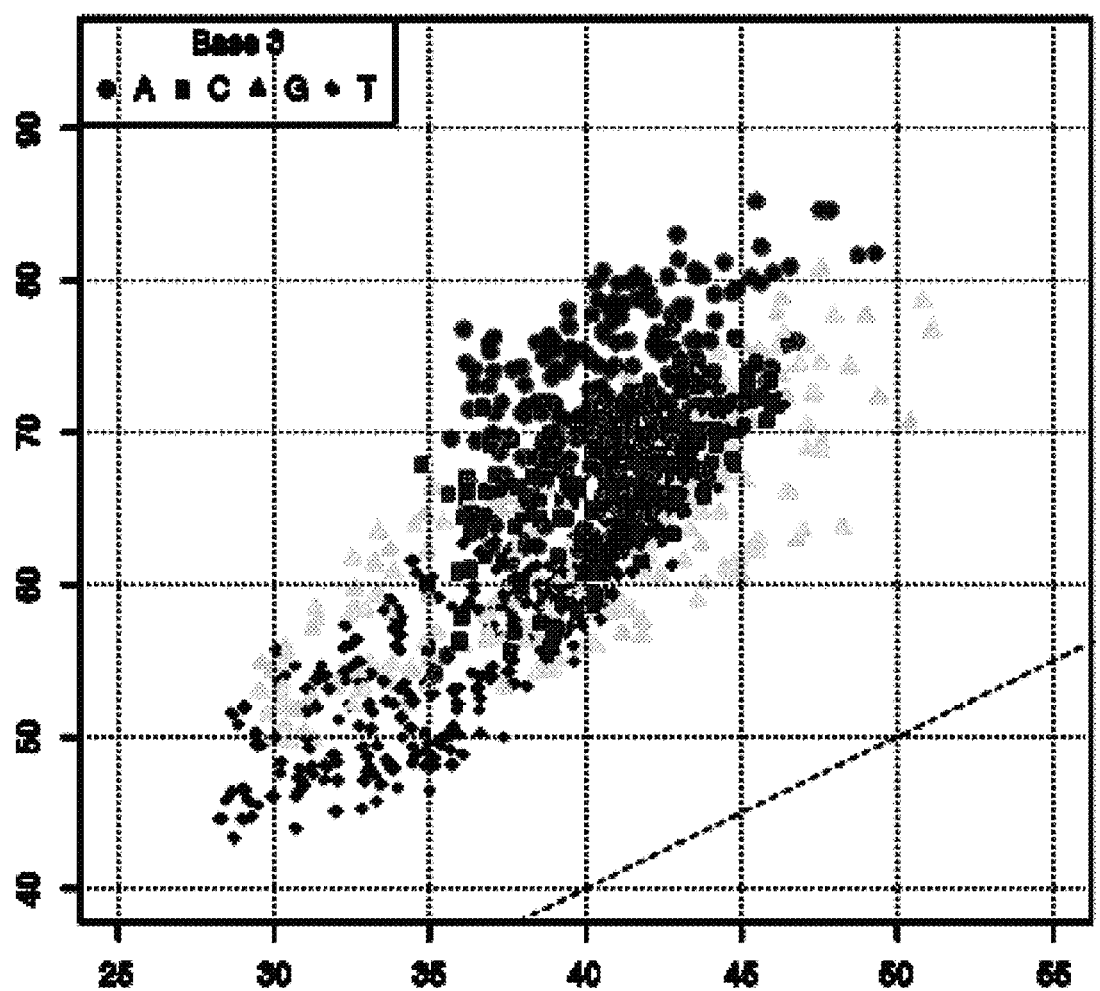
FIG. 20 shows a diagonal dot plot for the 3.6 kB modified DNA construct which was made up of C, T, G and 2-fluoro-adenosine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.

The diagonal dot plots for base combinations 1 and 2 are shown in FIGS. 19 and 20 (again these figures have a k=5 Kmer). These examples illustrate that it was possible to observe distinct changes when compared to the standard model when a 3.6 kB modified strand was used (which was produced using the base combinations 1) 5-carboxy-2'-deoxycytidine-5'triphosphate used with dATP/dGTP/dTTP or 2) 2-fluoro-adenosine-5'triphosphate used with dCTP/dGTP/dTTP).

Example 7

This example describes how a T4 Dda-E94C/A360C (SEQ ID NO: 24 with mutations E94C/A360C) enzyme controlled the movement of modified polynucleotides through a single MspA nanopore. The nucleotide species (A) in the randomly fragmented template polynucleotide lambda genomic DNA was replaced with a different nucleotide species (2'-fluoro-2'-deoxyadenosine-5'-triphosphate) in the modified polynucleotide.

Materials and Methods

Figure 17:
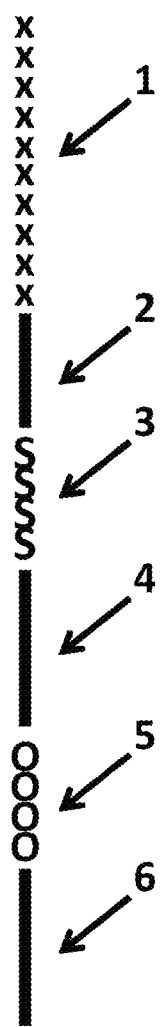
FIG. 17 shows a cartoon representation of the primer used in Example 7. Region 1 corresponds to 30 iSpC3 spacers. Region 2 corresponds to SEQ ID NO: 45. Region 3 corresponds to four iSp18 spacers. Region 4 corresponds to SEQ ID NO: 36. Region 5 corresponds to four 5-nitroindoles. Region 6 corresponds to SEQ ID NO: 46.

Lambda genomic DNA dam⁻ (1 ug, NEB) was randomly fragmented using a Covaris g-tube at 6,000 rpm for 1 minute. The recovered DNA was then end-repaired and dA-tailed, using NEB's NEBNext End-Repair and NEBNext dA-tailing Kits respectively (according to the manufacturer's instructions) each time purified using SPRI beads (Agencourt AMPure). Recovered DNA was then ligated to an adapter (400 nM, SEQ ID NO: 43 and 44) with 1× Blunt/TA Master Mix (NEB), for 15 mins at room temperature and then purified using SPRI beads (Agencourt AMPure). To the adapter ligated DNA (1 ug) ThermoPol Buffer (NEB) was added to make 100 ul of 1×, along with 200 nM of each dNTP (2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate), 200 nM primer (see FIG. 17 for cartoon image of primer structure and appropriate sequences) and 10 units of 9° N DNA Polymerase (NEB). Reactions were then heated to 95° C. for 2.5 mins, 55° C. for 20 secs and 72° C. for 30 mins. Amplified DNA was then purified using SPRI beads (Agencourt AMPure).

A DNA tether (50 nM, SEQ ID NO: 42) was annealed in 25 mM potassium phosphate (pH 8), 151 mM KCl for 15 mins at room temperature. T4 Dda-E94C/A360C (200 nM, SEQ ID NO: 24 with mutations E94C/A360C) was then added and the reaction was left for 5 mins at room temperature. TMAD (100 mM, N,N,N',N'-Tetramethylazodicarboxamide, Sigma Aldrich—D3648) was then added and the experimental pre-mix was left for a further 5 mins at room temperature.

The experimental pre-mix was then used for nanopore experiments. Electrical measurements were acquired at 20-45° C. from single MspA nanopores inserted in block co-polymer in buffer (600 mM KCl, 25 mM K Phosphate buffer, 75 mM Potassium Ferrocyanide (II), 25 mM Potassium Ferricyanide (III), pH 8). After achieving a single pore inserted in the block co-polymer, then buffer (3 mL, 960 mM KCl, 3 mM Potassium Ferrocyanide (II), 1 mM Potassium ferricyanide (III), 25 mM potassium phosphate pH 8) was flowed through the system to remove any excess MspA nanopores. MgCl$_2$ (1 mM final concentration) and ATP (2 mM final concentration, Sigma Aldrich—A6559-25UMO) were mixed together with buffer (500 mM KCl, 25 mM potassium phosphate pH 8) and then added to the modified DNA construct experimental pre-mix. 150 ul of the pre-mix was then added to the nanopore experimental system. Experiments were carried out for six hours, at 140 mV, and helicase-controlled DNA movement was monitored.

Helicase controlled DNA movements were individually base-called and then all movement reads were used to create a consensus. A consensus was created by first aligning the movement reads to a reference sequence using standard genome scale alignment software. At each alignment position a naïve maximum frequency consensus was formed. Where the data indicated a deletion or insertion with respect to the reference sequence, these were retained in the consensus. The consensus sequence was then itself aligned to the reference sequence. The allele frequencies of the movement reads across alignment positions, and the consensus sequence were inspected with the visualisation software IGV.

Results and Discussion

Helicase controlled DNA movement was observed for the modified random lambda DNA construct tested, where during synthesis all the A's in the sequences were replaced with 2'-Fluoro-2'-deoxyadenosine-5'-triphosphate.

Figure 18:
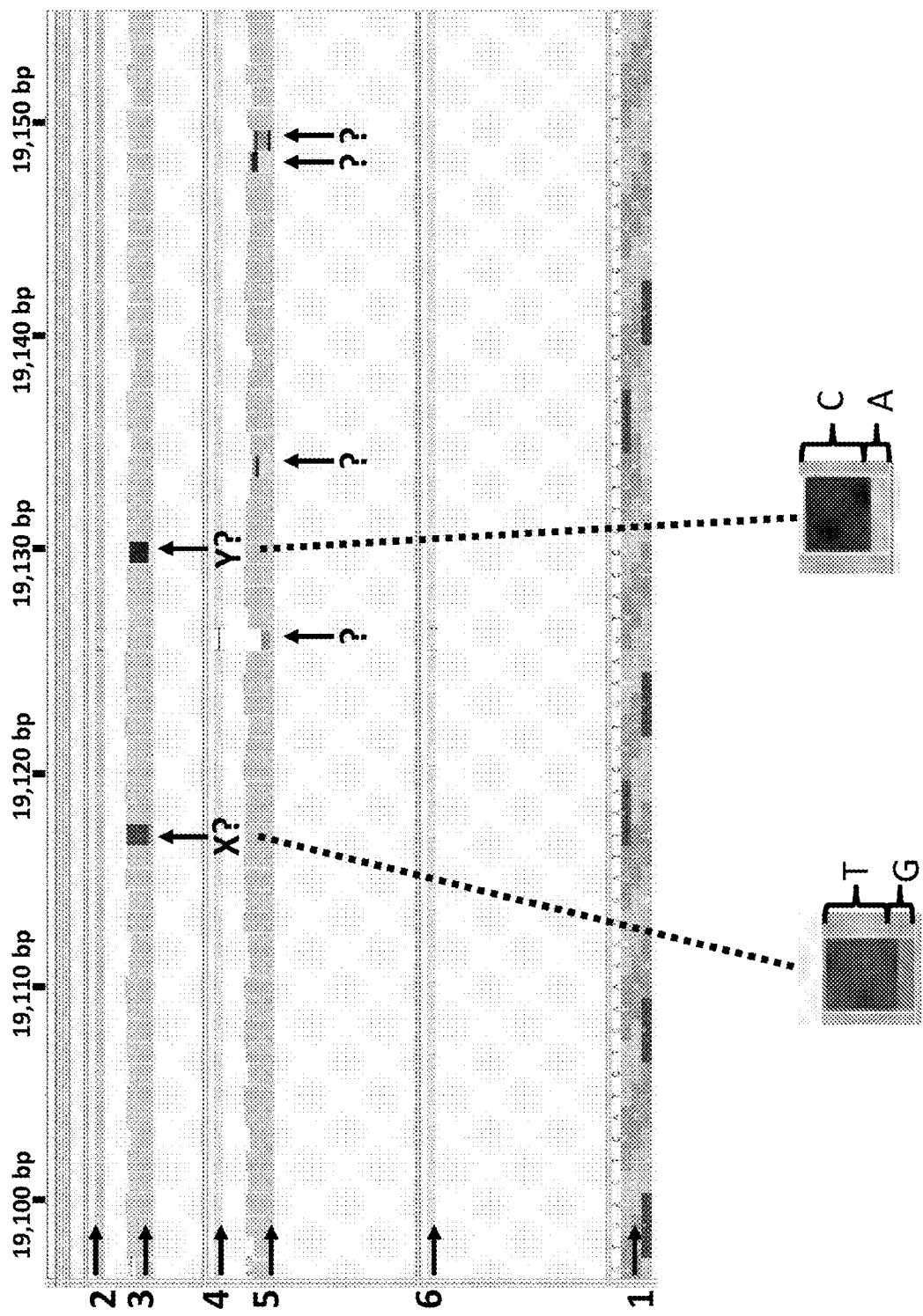
FIG. 18 shows a pictorial representation of a region of the lambda genomic DNA sequence (19,100 bp-19,150 bp) alignment. The reference sequence is shown in line 1. The consensus sequence when the DNA template was copied using A) 2'-deoxyadenosine-5'-triphosphate, 2'-deoxyguanosine-5'-triphosphate, 2'-deoxythymine-5'-triphosphate, 2'-deoxycytosine-5'-triphosphate is shown at line 4 and the corresponding allele frequencies at line 5. The consensus sequence when the DNA template was copied using B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate is shown at line 2 and the corresponding allele frequencies at line 3. Line 6 corresponds to when the data for both strands (made by polymerisation of the template using A or B bases) have been combined. The arrows with the '?' show positions for which the consensus sequence is ambiguous; it was not possible to form a consensus with a confidence greater than 80%. When line 3 and 5 were compared the positions for which it was not possible to form a consensus with a confidence of 80% or greater occurred at different positions in the sequence. When the data were combined (line 6) a correct consensus sequence could be formed. In order to aid in the understanding of the figure, two of the regions marked with an arrow with 'X?' or 'Y?' have been expanded and are shown below the main figure. For 'X?' the position was called as a T in around 65% of the helicase controlled DNA movements analysed (of the strand made of B bases) but as a G in around 35% of the helicase controlled DNA movements analysed (of the strand made of B bases). For 'Y?' the position was called as a C in around 65% of the helicase controlled DNA movements analysed (of the strand made of B bases) but as an A in around 35% of the helicase controlled DNA movements analysed (of the strand made of B bases). For each arrow '?' position the allele frequencies are shaded different shades of grey corresponding to which base is called at that position.
Figure 21:
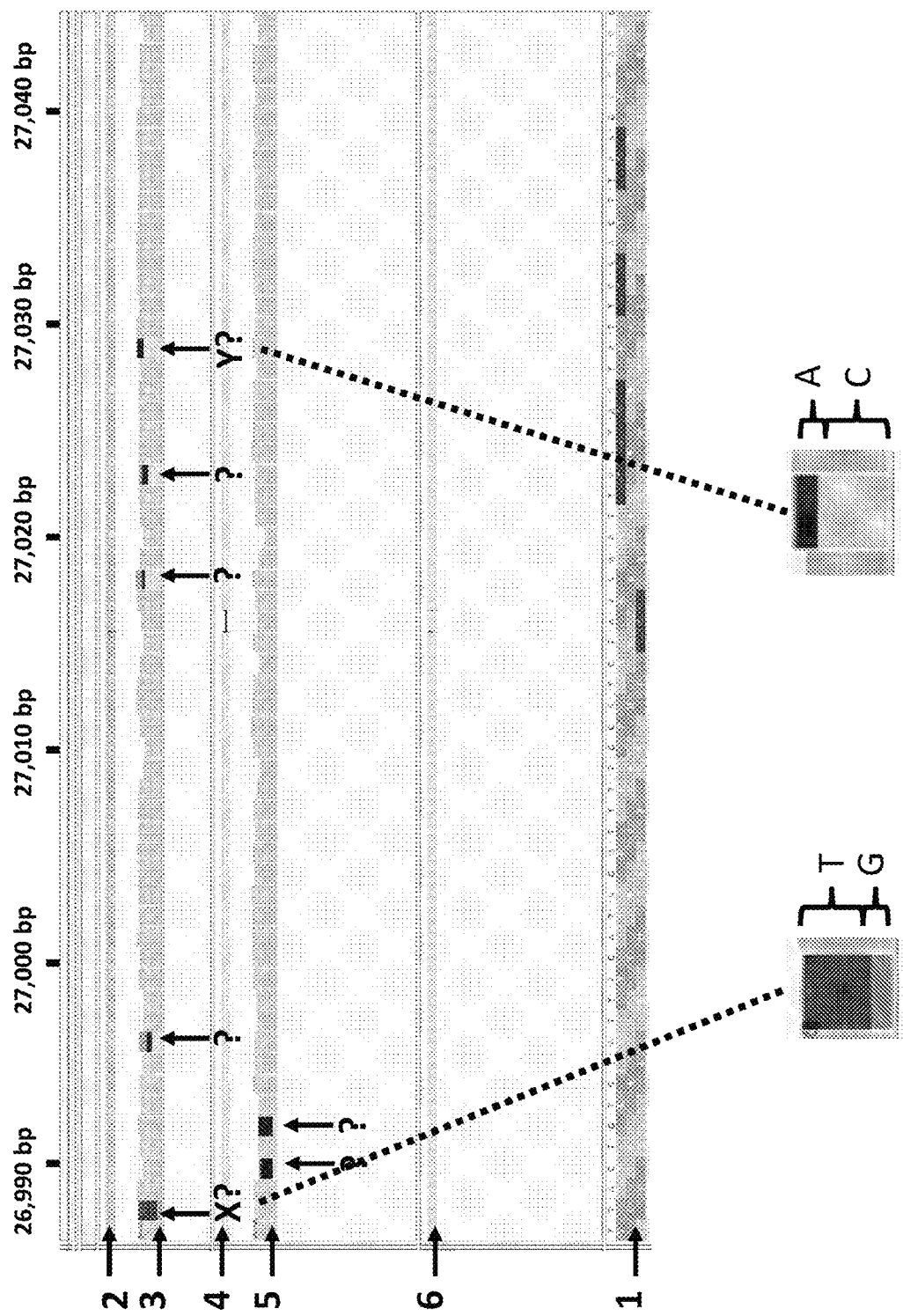
FIG. 21 shows a pictorial representation of a region of the lambda genomic DNA sequence (26,990-27,040 bp) alignment. The reference sequence is shown in line 1. The consensus sequence when the DNA template was copied using A) 2'-deoxyadenosine-5'-triphosphate, 2'-deoxyguanosine-5'-triphosphate, 2'-deoxythymine-5'-triphosphate, 2'-deoxycytosine-5'-triphosphate is shown at line 4 and the corresponding allele frequencies at line 5. The consensus sequence when the DNA template was copied using B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate is shown at line 2 and the corresponding allele frequencies at line 3. Line 6 corresponds to when the data for both strands (made by polymerisation of the template using A or B bases) has been combined. The arrows with the '?' show positions for which the consensus sequence is ambiguous; it was not possible to form a consensus with a confidence greater than 80%. When line 3 and 5 were compared the positions for which it was not possible to form a consensus with a confidence of 80% or greater occurred at different positions in the sequence. When the data were combined (line 6) a correct consensus sequence could be formed. In order to aid in the understanding of the figure, two of the regions which are marked with an arrow with 'X?' or 'Y?' have been expanded and are shown below the main figure. For 'X?' the position was called as a T in around 65% of the helicase controlled DNA movements analysed (of the strand made of B bases) but as a G in around 35% of the helicase controlled DNA movements analysed (of the strand made of B bases). For 'Y?' the position was called as an A in around 65% of the helicase controlled DNA movements analysed (of the strand made of B bases) but as a C in around 35% of the helicase controlled DNA movements analysed (of the strand made of B bases). For each arrow '?' position the allele frequencies are shaded different shades of grey corresponding to which base is called at that position.

The alignments shown in FIGS. 18 and 21 display zoomed in regions of the lambda genomic DNA sequence alignment. Each figure shows the alignment along with the consensus, using the lambda genomic sequence as a reference (line 1 for all figures), for the DNA made with either A) 2'-deoxyadenosine-5'-triphosphate, 2'-deoxyguanosine-5'-triphosphate, 2'-deoxythymine-5'-triphosphate, 2'-deoxycytosine-5'-triphosphate (consensus=line 4 and allele frequencies=line 5 for all figures) or B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate (consensus=line 2 and allele frequencies=line 3 for all figures). Any ambiguities in the consensus sequence for a specific base at a specific site or position can be seen for each of the templates (marked with arrows with '?' in all figures). This example illustrates that for both alignments the ambiguities in the consensus sequence for a specific base site or position when compared to the reference occur at different points in the sequence for DNA templates made from either (A) or (B) bases. It was possible to increase the probability of resolving the ambiguity in the consensus sequence, when both sets of data were combined (line 6 shows no arrows '?'). The specific sites or positions in the sequence where it was not possible to form a consensus with a confidence of greater than 80% would have remained unresolved for either A or B combination of bases had the data from both experiments not been combined. It was also possible to increase the probability of resolving ambiguities in deletions and insertions in the consensus sequence, when both sets of data were combined.

The invention claimed is:

1. A method of characterising a template polynucleotide composed of different polymer units defining a sequence of template nucleotides, the method comprising:
   a) contacting the template polynucleotide with a polymerase and a pool of free nucleotides under conditions in which the polymerase forms a modified polynucleotide using the template polynucleotide as a template for synthesizing the modified polynucleotide, wherein the pool of free nucleotides consists of:
      i) at least two modified nucleotides that each base pair with at least one template nucleotide of the sequence of template nucleotides; and
      ii) nucleotides that specifically base pair with each of the remaining template nucleotides of the sequence of nucleotides, but that do not specifically base pair with the at least one template nucleotide of i) wherein at least two of the two or more modified nucleotides in the pool base pair with one another;
   b) contacting the modified polynucleotide with a transmembrane pore in the presence of an electrical potential across the transmembrane pore, such that the modified polynucleotide moves through the pore; and
   c) taking one or more electrical measurements as the modified polynucleotide moves through the pore, wherein incorporation of the at least two modified nucleotides into the modified polynucleotide results in the one or more electrical measurements having an improved signal to noise ratio compared with electrical measurements taken as the template polynucleotide moves through the pore.

2. The method according to claim 1, wherein the polymerase does not form a complementary polynucleotide if the template polynucleotide is RNA.

3. The method according to claim 1, wherein the pool of free nucleotides includes, in i), two modified nucleotides, wherein each of the two modified nucleotides base pairs with a different template nucleotide.

4. The method according to claim 1, wherein:
   (a) the template polynucleotide is DNA and the template nucleotides of the polymer units include deoxyadenosine monophosphate (dAMP), deoxyguanosine monophosphate (dGMP), deoxythymidine monophosphate (dTMP), deoxycytidine monophosphate (dCMP) and/or deoxymethylcytidine monophosphate; or
   (b) the template polynucleotide is RNA and the template nucleotides of the polymer units include adenosine monophosphate (AMP), guanosine monophosphate (GMP), uridine monophosphate (UMP), cytidine monophosphate (CMP) and/or 5-methylcytidine monophosphate.

5. The method according to claim 1, wherein:
   (a) the template polynucleotide is DNA and the modified polynucleotide comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine; or
   (b) the template polynucleotide is RNA and the modified polynucleotide comprises a nucleobase which differs from adenine, guanine, uracil, cytosine or methylcytosine and/or comprises a nucleoside which differs from adenosine, guanosine, uridine, cytidine or methylcytidine.

6. The method according to claim 1, wherein each of the at least two modified nucleotides in i) is selected from the group consisting of hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole, phenyl (C6-aromatic ring), 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine.

7. The method according to claim 1, wherein the polymerase synthesizes a modified polynucleotide which comprises a chemical group or atom absent from the template polynucleotide.

8. The method according to claim 7, wherein the chemical group is selected from the group consisting of a propynyl group, a thio group, an oxo group, a methyl group, a hydroxymethyl group, a formyl group, a carboxy group, a carbonyl group, a benzyl group, a propargyl group or a propargylamine group.

9. The method according to claim 1, wherein the polymerase synthesizes a modified polynucleotide which lacks a chemical group or atom present in the template polynucleotide.

10. The method according to claim 1, wherein the polymerase synthesizes a modified polynucleotide having an altered electronegativity relative to the template polynucleotide.

11. The method according to claim 10, wherein the modified polynucleotide comprises a halogen atom.

12. The method according to claim 1, wherein step (a) further comprises selectively removing the nucleobases from one or more nucleotide species in the modified polynucleotide.

13. The method according to claim 1, wherein the template polynucleotide is single stranded.

14. The method according to claim 13, wherein the method further comprises before step (a) ligating a hairpin adaptor to one end of the template polynucleotide such that in step (a) the ligated hairpin adaptor acts as a primer for formation of the modified polynucleotide by the polymerase such that the modified and template polynucleotides are ligated by the hairpin adaptor.

15. The method according to claim 14, wherein the method comprises:
   b) contacting the ligated modified and template polynucleotides with a transmembrane pore such that the polynucleotides move through the pore; and
   c) taking one or more electrical measurements as the polynucleotides moves through the pore wherein the electrical measurements are indicative of one or more characteristics of the polynucleotides and thereby characterising the template polynucleotide.

16. The method according to claim 1, wherein the template polynucleotide is double stranded.

* * * * *

SEQUENCE LISTING

```
<160> NUMBER OF SEQ ID NOS: 49

<210> SEQ ID NO 1
<211> LENGTH: 558
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E193K)

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gaccegtgaa     120 tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
```

```
ggcaatggtc cgggcattca agaagtggca acctttagtg tgcgcgtttc cggcgctaaa    420
ggcggtgtcg cggtgtctaa cgcccacggt accgttacgg gcgcggccgg cggtgtcctg    480
ctgcgtccgt tcgcgcgcct gattgcctct accggcgaca gcgttacgac ctatggcgaa    540
ccgtggaata tgaactaa                                                  558

<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 885
<212> TYPE: DNA
<213> ORGANISM: Artificial Sequence
<220> FEATURE:
<223> OTHER INFORMATION: alpha-hemolysin mutant (E111N/K147N)

<400> SEQUENCE: 3
atggcagatt ctgatattaa tattaaaacc ggtactacag atattggaag caatactaca    60
gtaaaaacag gtgatttagt cacttatgat aaagaaaatg gcatgcacaa aaaagtattt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240 tggcccttcag cctttaaggt acagttgcaa ctacctgata tgaagtagc tcaaatatct    300 gattactatc caagaaattc gattgataca aaaaactata tgagtacttt aacttatgga    360
ttcaacggta atgttactgg tgatgataca ggaaaaattg gcggcctta tggtgcaaat    420
```

```
gtttcgattg gtcatacact gaactatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                   885
```

<210> SEQ ID NO 4
<211> LENGTH: 293
<212> TYPE: PRT
<213> ORGANISM: Artificial Sequence
<220> FEATURE:
<223> OTHER INFORMATION: alpha-hemolysin mutant (E111N/K147N)

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
```

```
                    275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
```

```
                115                 120                 125
Ala Thr Phe Ser Val Asp Val Ser Gly Pro Ala Gly Gly Val Ala Val
            130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Bacillus subtilis phage phi29

<400> SEQUENCE: 8
atgaaacaca tgccgcgtaa aatgtatagc tgcgcgtttg aaaccacgac caaagtggaa      60
gattgtcgcg tttgggccta tggctacatg aacatcgaag tcattctgaa atacaaaatc     120
ggtaacagtc tggatgaatt tatggcatgg gtgctgaaag ttcaggcgga tctgtacttc     180
cacaacctga atttgatgg cgcattcatt atcaactggc tggaacgtaa tggctttaaa      240
tggagcgcgg atggtctgcc gaacacgtat aataccatta tctctcgtat gggccagtgg     300
tatatgattg atatctgcct gggctacaaa ggtaaacgca aaattcatac cgtgatctat     360
gatagcctga aaaaactgcc gtttccggtg aagaaaattg cgaaagattt caaactgacg     420
```

```
gttctgaaag gcgatattga ttatcacaaa gaacgtccgg ttggttacaa aatcaccccg    480
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaaagtg ttcccgacgc tgagcctggg tctggataaa    660
gaagttcgtt atgcctaccg cggcggtttt acctggctga cgatcgtttt caagaaaaaa    720
gaaattggcg agggtatggt gtttgatgtt aatagtctgt atccggcaca gatgtacagc    780
cgcctgctgc cgtatggcga accgatcgtg ttcgagggta aatatgtttg ggatgaagat    840
tacccgctgc atattcagca catccgttgt gaatttgaac tgaaagaagg ctatattccg    900
accattcaga tcaaacgtag tcgcttctat aagggtaacg aatacctgaa agctctggc    960
ggtgaaatcg cggatctgtg gctgagtaac gtggatctgg aactgatgaa agaacactac   1020
gatctgtaca cgttgaata catcagcggc ctgaaattta agccacgac cggtctgttc   1080
aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg tgtgtggttct ggtggatgat acgtttacca ttaaatctgg cggtagtgcg   1740
tggagccatc cgcagttcga aaaaggcggt ggctctggtg gcggttctgg cggtagtgcc   1800
tggagccacc cgcagtttga aaataataa                                    1830
```

<210> SEQ ID NO 9
<211> LENGTH: 608
<212> TYPE: PRT
<213> ORGANISM: Bacillus subtilis phage phi29

<400> SEQUENCE: 9

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe

```
            115                 120                 125
Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
            210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                    245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                    325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540
```

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 10
<211> LENGTH: 1390
<212> TYPE: DNA
<213> ORGANISM: Escherichia coli

<400> SEQUENCE: 10

| | |
|---|---|
| atgatgaacg atggcaaaca gcagagcacc ttcctgtttc atgattatga aaccttcggt | 60 |
| acccatccgg ccctggatcg tccggcgcag tttgcggcca ttcgcaccga tagcgaattc | 120 |
| aatgtgattg gcgaaccgga agtgttttat tgcaaaccgg ccgatgatta tctgccgcag | 180 |
| ccgggtgcgg tgctgattac cggtattacc ccgcaggaag cgcgcgcgaa aggtgaaaac | 240 |
| gaagcggcgt tgccgcgcg cattcatagc ctgtttaccg tgccgaaaac ctgcattctg | 300 |
| ggctataaca atgtgcgctt cgatgatgaa gttacccgta atatcttta tcgtaacttt | 360 |
| tatgatccgt atgcgtggag ctggcagcat gataacagcc gttgggatct gctggatgtg | 420 |
| atgcgcgcgt gctatgcgct cgcccggaa ggcattaatt ggccggaaaa cgatgatggc | 480 |
| ctgccgagct ttcgtctgga acatctgacc aaagccaacg gcattgaaca tagcaatgcc | 540 |
| catgatgcga tggccgatgt ttatgcgacc attgcgatgg cgaaactggt taaaacccgt | 600 |
| cagccgcgcc tgtttgatta tctgtttacc accgtaaca aacacaaact gatggcgctg | 660 |
| attgatgttc cgcagatgaa accgctggtg catgtgagcg gcatgtttgg cgcctggcgc | 720 |
| ggcaacacca gctgggtggc cccgctggcc tggcacccgg aaaatcgtaa cgccgtgatt | 780 |
| atggttgatc tggccggtga tattagcccg ctgctggaac tggatagcga taccctgcgt | 840 |
| gaacgcctgt ataccgccaa aaccgatctg gcgataatg ccgccgtgcc ggtgaaactg | 900 |
| gttcacatta caaatgccc ggtgctggcc caggcgaaca ccctgcgccc ggaagatgcg | 960 |
| gatcgtctgg gtattaatcg ccagcattgt ctggataatc tgaaaatcct gcgtgaaaac | 1020 |
| ccgcaggtgc gtgaaaagt ggtggcgatc ttcgcggaag cggaaccgtt caccccgagc | 1080 |
| gataacgtgg atgcgcagct gtataacggc ttctttagcg atgccgatcg cgcggcgatg | 1140 |
| aaaatcgttc tggaaaccga accgcgcaat ctgccggcgc tggatattac ctttgttgat | 1200 |
| aaacgtattg aaaaactgct gtttaattat cgtgcgcgca attttccggg taccctggat | 1260 |
| tatgccgaac agcagcgttg gctggaacat cgtcgtcagg ttttcacccc ggaatttctg | 1320 |
| cagggttatg cggatgaact gcagatgctg gttcagcagt atgccgatga taaagaaaaa | 1380 |
| gtggcgctgc | 1390 |

<210> SEQ ID NO 11
<211> LENGTH: 485
<212> TYPE: PRT
<213> ORGANISM: Escherichia coli

<400> SEQUENCE: 11

Met Met Asn Asp Gly Lys Gln Gln Ser Thr Phe Leu Phe His Asp Tyr
1               5                   10                  15

```
Glu Thr Phe Gly Thr His Pro Ala Leu Asp Arg Pro Ala Gln Phe Ala
         20                  25                  30

Ala Ile Arg Thr Asp Ser Glu Phe Asn Val Ile Gly Glu Pro Glu Val
         35                  40                  45

Phe Tyr Cys Lys Pro Ala Asp Asp Tyr Leu Pro Gln Pro Gly Ala Val
         50                  55                  60

Leu Ile Thr Gly Ile Thr Pro Gln Glu Ala Arg Ala Lys Gly Glu Asn
65                   70                  75                  80

Glu Ala Ala Phe Ala Ala Arg Ile His Ser Leu Phe Thr Val Pro Lys
                 85                  90                  95

Thr Cys Ile Leu Gly Tyr Asn Asn Val Arg Phe Asp Asp Glu Val Thr
             100                 105                 110

Arg Asn Ile Phe Tyr Arg Asn Phe Tyr Asp Pro Tyr Ala Trp Ser Trp
             115                 120                 125

Gln His Asp Asn Ser Arg Trp Asp Leu Leu Asp Val Met Arg Ala Cys
         130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                 165                 170                 175

His Ser Asn Ala His Asp Ala Met Ala Asp Val Tyr Ala Thr Ile Ala
             180                 185                 190

Met Ala Lys Leu Val Lys Thr Arg Gln Pro Arg Leu Phe Asp Tyr Leu
             195                 200                 205

Phe Thr His Arg Asn Lys His Lys Leu Met Ala Leu Ile Asp Val Pro
         210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                 245                 250                 255

Asn Ala Val Ile Met Val Asp Leu Ala Gly Asp Ile Ser Pro Leu Leu
             260                 265                 270

Glu Leu Asp Ser Asp Thr Leu Arg Glu Arg Leu Tyr Thr Ala Lys Thr
         275                 280                 285

Asp Leu Gly Asp Asn Ala Ala Val Pro Val Lys Leu Val His Ile Asn
         290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                 325                 330                 335

Leu Arg Glu Asn Pro Gln Val Arg Glu Lys Val Val Ala Ile Phe Ala
             340                 345                 350

Glu Ala Glu Pro Phe Thr Pro Ser Asp Asn Val Asp Ala Gln Leu Tyr
         355                 360                 365

Asn Gly Phe Phe Ser Asp Ala Asp Arg Ala Ala Met Lys Ile Val Leu
         370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                 405                 410                 415

Gly Thr Leu Asp Tyr Ala Glu Gln Gln Arg Trp Leu Glu His Arg Arg
             420                 425                 430
```

```
Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
        450                 455                 460

Lys Ala Leu Trp Gln Tyr Ala Glu Glu Ile Val Ser Gly Ser Gly His
465                 470                 475                 480

His His His His His
                485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc     60
atcgtcgaaa agcaccaacc ggatgtgatt ggcctgcagg agacaaaagt tcatgacgat    120
atgtttccgc tcgaagaggt ggcgaagctc ggctacaact gtttttatca cgggcagaaa    180
ggccattatg gcgtggcgct gctgaccaaa gagacgccga ttgccgtgcg tcgcggcttt    240
cccggtgacg acgaagaggc gcagcggcgg attattatgg cggaaatccc ctcactgctg    300
ggtaatgtca ccgtgatcaa cggttacttc cgcagggtg aaagccgcga ccatccgata    360 aaattccccgg caaaagcgca gttttatcag aatctgcaaa actacctgga accgaactc    420 aaacgtgata atccggtact gattatgggc gatatgaata tcagccctac agatctggat    480
atcggcattg gcaagaaaaa ccgtaagcgc tggctgcgta ccgtaaatg ctctttcctg    540 ccggaagagc gcgaatggat ggacaggctg atgagctggg ggttggtcga taccttccgc    600
catgcgaatc cgcaaacagc agatcgtttc tcatggtttg attaccgctc aaaaggtttt    660
gacgataacc gtggtctgcg catcgacctg ctgctcgcca gccaaccgct ggcagaatgt    720
tgcgtagaaa ccggcatcga ctatgaaatc gcagcatgg aaaaaccgtc cgatcacgcc    780
cccgtctggg cgaccttccg ccgc                                          804

<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125
```

```
Tyr Gln Asn Leu Gln Asn Tyr Leu Glu Thr Glu Leu Lys Arg Asp Asn
        130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
210                 215                 220

Gly Leu Arg Ile Asp Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
        260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120
ggcgactatg atgcggatgg cctgaccggc accgcgatcc tggttcgtgg tctggccgcc    180
ctgggtgcgg atgttcatcc gtttatcccg caccgcctgg aagaaggcta tggtgtcctg    240
atggaacgct cccggaaca tctggaagcc tcggacctgt ttctgaccgt tgactgcggc    300
attaccaacc atgcggaact cgcgcgaactg ctggaaaatg gcgtggaagt cattgttacc    360
gatcatcata cgccgggcaa aacgccgccg cgggtctgg tcgtgcatcc ggcgctgacg     420
ccggatctga agaaaaaacc gaccggcgca ggcgtggcgt ttctgctgct gtgggcactg    480
catgaacgcc tggcctgcc ccgccgctg gaatacgcgg acctggcagc cgttggcacc     540
attgccgacg ttgccccgct gtggggttgg aatcgtgcac tggtgaaaga aggtctggca    600
cgcatcccgg cttcatcttg ggtgggcctg cgtctgctgg ctgaagccgt gggctatacc    660
ggcaaagcgg tcgaagtcgc tttccgcatc gcgccgcgca tcaatgcggc ttcccgcctg    720
ggcgaagcgg aaaaagcct gcgcctgctg ctgacggatg atgcggcaga agctcaggcg    780
ctggtcggcg aactgcaccg tctgaacgcc gtcgtcaga ccctggaaga agcgatgctg     840
cgcaaactgc tgccgcaggc cgaccgggaa gcgaaagcca tcgttctgct ggacccggaa    900
ggccatccgg tgttatggg tattgtggcc tctcgcatcc tggaagcgac cctgcgcccg    960
gtctttctgg tggcccaggg caaaggcacc gtgcgttcgc tggctccgat tccgccgtc    1020
gaagcactgc gcagcgcgga agatctgctg ctgcgttatg tggtcataa agaagcggcg   1080
ggtttcgcaa tggatgaagc gctgtttccg gcgttcaaag cacgcgttga agcgtatgcc    1140
gcacgttttcc cggatccggt tcgtgaagtg gcactgctgg atctgctgcc ggaaccgggc    1200
ctgctgccga ggtgttccg tgaactggca ctgctggaac cgtatggtga aggtaaccccg    1260
gaaccgctgt tcctg                                                    1275
```

<210> SEQ ID NO 15
<211> LENGTH: 425
<212> TYPE: PRT
<213> ORGANISM: Thermus thermophilus

<400> SEQUENCE: 15

| | | | | | | | | | | | | | | |
|---|---|---|---|---|---|---|---|---|---|---|---|---|---|---|
| Met | Phe | Arg | Arg | Lys | Glu | Asp | Leu | Asp | Pro | Pro | Leu | Ala | Leu | Leu | Pro |
| 1 | | | | 5 | | | | | 10 | | | | | 15 | |
| Leu | Lys | Gly | Leu | Arg | Glu | Ala | Ala | Leu | Leu | Glu | Glu | Ala | Leu | Arg | |
| | | | 20 | | | | | 25 | | | | | 30 | | |
| Gln | Gly | Lys | Arg | Ile | Arg | Val | His | Gly | Asp | Tyr | Asp | Ala | Asp | Gly | Leu |
| | | | 35 | | | | | 40 | | | | | 45 | | |
| Thr | Gly | Thr | Ala | Ile | Leu | Val | Arg | Gly | Leu | Ala | Ala | Leu | Gly | Ala | Asp |
| | 50 | | | | | 55 | | | | | 60 | | | | |
| Val | His | Pro | Phe | Ile | Pro | His | Arg | Leu | Glu | Glu | Gly | Tyr | Gly | Val | Leu |
| 65 | | | | | 70 | | | | | 75 | | | | | 80 |
| Met | Glu | Arg | Val | Pro | Glu | His | Leu | Glu | Ala | Ser | Asp | Leu | Phe | Leu | Thr |
| | | | | 85 | | | | | 90 | | | | | 95 | |
| Val | Asp | Cys | Gly | Ile | Thr | Asn | His | Ala | Glu | Leu | Arg | Glu | Leu | Leu | Glu |
| | | | 100 | | | | | 105 | | | | | 110 | | |
| Asn | Gly | Val | Glu | Val | Ile | Val | Thr | Asp | His | His | Thr | Pro | Gly | Lys | Thr |
| | | | 115 | | | | | 120 | | | | | 125 | | |
| Pro | Pro | Pro | Gly | Leu | Val | Val | His | Pro | Ala | Leu | Thr | Pro | Asp | Leu | Lys |
| | 130 | | | | | 135 | | | | | 140 | | | | |
| Glu | Lys | Pro | Thr | Gly | Ala | Gly | Val | Ala | Phe | Leu | Leu | Leu | Trp | Ala | Leu |
| 145 | | | | | 150 | | | | | 155 | | | | | 160 |
| His | Glu | Arg | Leu | Gly | Leu | Pro | Pro | Pro | Leu | Glu | Tyr | Ala | Asp | Leu | Ala |
| | | | | 165 | | | | | 170 | | | | | 175 | |
| Ala | Val | Gly | Thr | Ile | Ala | Asp | Val | Ala | Pro | Leu | Trp | Gly | Trp | Asn | Arg |
| | | | 180 | | | | | 185 | | | | | 190 | | |
| Ala | Leu | Val | Lys | Glu | Gly | Leu | Ala | Arg | Ile | Pro | Ala | Ser | Ser | Trp | Val |
| | | | 195 | | | | | 200 | | | | | 205 | | |
| Gly | Leu | Arg | Leu | Leu | Ala | Glu | Ala | Val | Gly | Tyr | Thr | Gly | Lys | Ala | Val |
| | 210 | | | | | 215 | | | | | 220 | | | | |
| Glu | Val | Ala | Phe | Arg | Ile | Ala | Pro | Arg | Ile | Asn | Ala | Ala | Ser | Arg | Leu |
| 225 | | | | | 230 | | | | | 235 | | | | | 240 |
| Gly | Glu | Ala | Glu | Lys | Ala | Leu | Arg | Leu | Leu | Leu | Thr | Asp | Asp | Ala | Ala |
| | | | | 245 | | | | | 250 | | | | | 255 | |
| Glu | Ala | Gln | Ala | Leu | Val | Gly | Glu | Leu | His | Arg | Leu | Asn | Ala | Arg | Arg |
| | | | 260 | | | | | 265 | | | | | 270 | | |
| Gln | Thr | Leu | Glu | Glu | Ala | Met | Leu | Arg | Lys | Leu | Leu | Pro | Gln | Ala | Asp |
| | | | 275 | | | | | 280 | | | | | 285 | | |
| Pro | Glu | Ala | Lys | Ala | Ile | Val | Leu | Leu | Asp | Pro | Glu | Gly | His | Pro | Gly |
| | 290 | | | | | 295 | | | | | 300 | | | | |
| Val | Met | Gly | Ile | Val | Ala | Ser | Arg | Ile | Leu | Glu | Ala | Thr | Leu | Arg | Pro |
| 305 | | | | | 310 | | | | | 315 | | | | | 320 |
| Val | Phe | Leu | Val | Ala | Gln | Gly | Lys | Gly | Thr | Val | Arg | Ser | Leu | Ala | Pro |
| | | | | 325 | | | | | 330 | | | | | 335 | |
| Ile | Ser | Ala | Val | Glu | Ala | Leu | Arg | Ser | Ala | Glu | Asp | Leu | Leu | Leu | Arg |
| | | | 340 | | | | | 345 | | | | | 350 | | |
| Tyr | Gly | Gly | His | Lys | Glu | Ala | Ala | Gly | Phe | Ala | Met | Asp | Glu | Ala | Leu |
| | | | 355 | | | | | 360 | | | | | 365 | | |
| Phe | Pro | Ala | Phe | Lys | Ala | Arg | Val | Glu | Ala | Tyr | Ala | Ala | Arg | Phe | Pro |

```
                    370                375                380
Asp Pro Val Arg Glu Val Ala Leu Leu Asp Leu Leu Pro Glu Pro Gly
385                     390                395                400

Leu Leu Pro Gln Val Phe Arg Glu Leu Ala Leu Leu Glu Pro Tyr Gly
                405                410                415

Glu Gly Asn Pro Glu Pro Leu Phe Leu
                420                425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg ggaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420
aaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
tactttgcca actatgaccc gcgtatgaag cgtgaaggcc tgcattatgt cgtgattgag     600
cgggatgaaa agtacatggc gagttttgac gagatcgtgc cggagttcat cgaaaaaatg     660
gacgaggcac tggctgaaat tggttttgta tttggggagc aatggcgatc tggctctggt     720
tccggcagcg gttccgga                                                   738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
                100                 105                 110

Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
        130                 135                 140
```

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser

```
            275                 280                 285
Thr Gly Glu Thr Asp Thr Ala Ile Val Leu Ala Asn Cys Ile Arg Lys
290                 295                 300
Gly Val Ala Phe His His Ala Gly Leu Asn Ser Asn His Arg Lys Leu
305                 310                 315                 320
Val Glu Asn Gly Phe Arg Gln Asn Leu Ile Lys Val Ile Ser Ser Thr
                    325                 330                 335
Pro Thr Leu Ala Ala Gly Leu Asn Leu Pro Ala Arg Arg Val Ile Ile
                340                 345                 350
Arg Ser Tyr Arg Arg Phe Asp Ser Asn Phe Gly Met Gln Pro Ile Pro
            355                 360                 365
Val Leu Glu Tyr Lys Gln Met Ala Gly Arg Ala Gly Arg Pro His Leu
        370                 375                 380
Asp Pro Tyr Gly Glu Ser Val Leu Leu Ala Lys Thr Tyr Asp Glu Phe
385                 390                 395                 400
Ala Gln Leu Met Glu Asn Tyr Val Glu Ala Asp Ala Glu Asp Ile Trp
                    405                 410                 415
Ser Lys Leu Gly Thr Glu Asn Ala Leu Arg Thr His Val Leu Ser Thr
                420                 425                 430
Ile Val Asn Gly Phe Ala Ser Thr Arg Gln Glu Leu Phe Asp Phe Phe
            435                 440                 445
Gly Ala Thr Phe Phe Ala Tyr Gln Gln Asp Lys Trp Met Leu Glu Glu
450                 455                 460
Val Ile Asn Asp Cys Leu Glu Phe Leu Ile Asp Lys Ala Met Val Ser
465                 470                 475                 480
Glu Thr Glu Asp Ile Glu Asp Ala Ser Lys Leu Phe Leu Arg Gly Thr
                    485                 490                 495
Arg Leu Gly Ser Leu Val Ser Met Leu Tyr Ile Asp Pro Leu Ser Gly
                500                 505                 510
Ser Lys Ile Val Asp Gly Phe Lys Asp Ile Gly Lys Ser Thr Gly Gly
            515                 520                 525
Asn Met Gly Ser Leu Glu Asp Asp Lys Gly Asp Asp Ile Thr Val Thr
        530                 535                 540
Asp Met Thr Leu Leu His Leu Val Cys Ser Thr Pro Asp Met Arg Gln
545                 550                 555                 560
Leu Tyr Leu Arg Asn Thr Asp Tyr Thr Ile Val Asn Glu Tyr Ile Val
                    565                 570                 575
Ala His Ser Asp Glu Phe His Glu Ile Pro Asp Lys Leu Lys Glu Thr
                580                 585                 590
Asp Tyr Glu Trp Phe Met Gly Glu Val Lys Thr Ala Met Leu Leu Glu
            595                 600                 605
Glu Trp Val Thr Glu Val Ser Ala Glu Asp Ile Thr Arg His Phe Asn
        610                 615                 620
Val Gly Glu Gly Asp Ile His Ala Leu Ala Asp Thr Ser Glu Trp Leu
625                 630                 635                 640
Met His Ala Ala Ala Lys Leu Ala Glu Leu Leu Gly Val Glu Tyr Ser
                    645                 650                 655
Ser His Ala Tyr Ser Leu Glu Lys Arg Ile Arg Tyr Gly Ser Gly Leu
                660                 665                 670
Asp Leu Met Glu Leu Val Gly Ile Arg Gly Val Gly Arg Val Arg Ala
            675                 680                 685
Arg Lys Leu Tyr Asn Ala Gly Phe Val Ser Val Ala Lys Leu Lys Gly
        690                 695                 700
```

```
Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
            725                 730                 735

Ser Ala Pro Ile Ser Ser Asn Thr Leu Asp Thr Leu Leu Asp Lys Asn
        740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
```

```
            305                 310                 315                 320
        Gln Asp Cys Arg Ser Val Val Glu Glu Phe Arg Ser Gly Arg Ile
                        325                 330                 335

Arg Leu Leu Ala Ser Thr Pro Thr Leu Ala Ala Gly Val Asn Leu Pro
                        340                 345                 350

Ala Arg Arg Val Val Ile Ser Val Met Arg Tyr Asn Ser Ser Ser
                        355                 360                 365

Gly Met Ser Glu Pro Ile Ser Ile Leu Glu Tyr Lys Gln Leu Cys Gly
                        370                 375                 380

Arg Ala Gly Arg Pro Gln Tyr Asp Lys Ser Gly Glu Ala Ile Val Val
        385                 390                 395                 400

Gly Gly Val Asn Ala Asp Glu Ile Phe Asp Arg Tyr Ile Gly Glu
                                405                 410                 415

Pro Glu Pro Ile Arg Ser Ala Met Val Asp Asp Arg Ala Leu Arg Ile
                        420                 425                 430

His Val Leu Ser Leu Val Thr Thr Ser Pro Gly Ile Lys Glu Asp Asp
                        435                 440                 445

Val Thr Glu Phe Phe Leu Gly Thr Leu Gly Gly Gln Gln Ser Gly Glu
                450                 455                 460

Ser Thr Val Lys Phe Ser Val Ala Val Ala Leu Arg Phe Leu Gln Glu
        465                 470                 475                 480

Glu Gly Met Leu Gly Arg Arg Gly Gly Arg Leu Ala Ala Thr Lys Met
                                485                 490                 495

Gly Arg Leu Val Ser Arg Leu Tyr Met Asp Pro Met Thr Ala Val Thr
                        500                 505                 510

Leu Arg Asp Ala Val Gly Glu Ala Ser Pro Gly Arg Met His Thr Leu
                        515                 520                 525

Gly Phe Leu His Leu Val Ser Glu Cys Ser Glu Phe Met Pro Arg Phe
                        530                 535                 540

Ala Leu Arg Gln Lys Asp His Glu Val Ala Glu Met Met Leu Glu Ala
        545                 550                 555                 560

Gly Arg Gly Glu Leu Leu Arg Pro Val Tyr Ser Tyr Glu Cys Gly Arg
                                565                 570                 575

Gly Leu Leu Ala Leu His Arg Trp Ile Gly Glu Ser Pro Glu Ala Lys
                        580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
                610                 615                 620

Gln Glu Arg Pro Asp Leu Leu Gly Glu Leu Asp Val Leu Arg Ser Arg
        625                 630                 635                 640

Val Ala Tyr Gly Ile Lys Ala Glu Leu Val Pro Leu Val Ser Ile Lys
                        645                 650                 655

Gly Ile Gly Arg Val Arg Ser Arg Arg Leu Phe Arg Gly Gly Ile Lys
                        660                 665                 670

Gly Pro Gly Asp Leu Ala Ala Val Pro Val Glu Arg Leu Ser Arg Val
                        675                 680                 685

Glu Gly Ile Gly Ala Thr Leu Ala Asn Asn Ile Lys Ser Gln Leu Arg
                690                 695                 700

Lys Gly Gly
        705

<210> SEQ ID NO 20
```

<211> LENGTH: 720
<212> TYPE: PRT
<213> ORGANISM: Thermococcus gammatolerans

<400> SEQUENCE: 20

```
Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
```

```
            385                 390                 395                 400
Lys Pro Glu Lys Leu Phe Ser Met Leu Ala Asn Glu Gln Ala Phe Arg
                    405                 410                 415

Ser Gln Val Leu Ala Leu Ile Thr Asn Phe Gly Ile Arg Ser Phe Pro
                420                 425                 430

Glu Leu Val Arg Phe Leu Glu Arg Thr Phe Tyr Ala His Gln Arg Lys
            435                 440                 445

Asp Leu Ser Ser Leu Glu Tyr Lys Ala Lys Glu Val Val Tyr Phe Leu
        450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
                500                 505                 510

Pro Phe Gly Ile Phe Gln Leu Ile Ala Ser Thr Pro Asp Met Ala Thr
            515                 520                 525

Leu Thr Ala Arg Arg Arg Glu Met Glu Asp Tyr Leu Asp Leu Ala Tyr
        530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Leu Glu Leu Ala Asp Trp Leu
            595                 600                 605

Met Tyr Ser Leu Ile Glu Leu Tyr Lys Leu Phe Glu Pro Lys Glu Glu
        610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
            675                 680                 685

Lys Ile Leu Asp Gly Ile Tyr Arg His Leu Gly Ile Glu Lys Arg Val
        690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
                20                  25                  30

Glu Lys Gly Leu Leu Glu Gly Lys Asn Leu Leu Ile Ser Ile Pro Thr
            35                  40                  45
```

```
Ala Ser Gly Lys Thr Leu Leu Ala Glu Met Ala Met Trp Ser Arg Ile
 50                  55                  60
Ala Ala Gly Gly Lys Cys Leu Tyr Ile Val Pro Leu Arg Ala Leu Ala
 65                  70                  75                  80
Ser Glu Lys Tyr Asp Glu Phe Ser Lys Lys Gly Val Ile Arg Val Gly
                 85                  90                  95
Ile Ala Thr Gly Asp Leu Asp Arg Thr Asp Ala Tyr Leu Gly Glu Asn
                100                 105                 110
Asp Ile Ile Val Ala Thr Ser Glu Lys Thr Asp Ser Leu Leu Arg Asn
            115                 120                 125
Arg Thr Pro Trp Leu Ser Gln Ile Thr Cys Ile Val Leu Asp Glu Val
130                 135                 140
His Leu Ile Gly Ser Glu Asn Arg Gly Ala Thr Leu Glu Met Val Ile
145                 150                 155                 160
Thr Lys Leu Arg Tyr Thr Asn Pro Val Met Gln Ile Ile Gly Leu Ser
                165                 170                 175
Ala Thr Ile Gly Asn Pro Ala Gln Leu Ala Glu Trp Leu Asp Ala Thr
                180                 185                 190
Leu Ile Thr Ser Thr Trp Arg Pro Val Asp Leu Arg Gln Gly Val Tyr
            195                 200                 205
Tyr Asn Gly Lys Ile Arg Phe Ser Asp Ser Glu Arg Pro Ile Gln Gly
210                 215                 220
Lys Thr Lys His Asp Asp Leu Asn Leu Cys Leu Asp Thr Ile Glu Glu
225                 230                 235                 240
Gly Gly Gln Cys Leu Val Phe Val Ser Ser Arg Arg Asn Ala Glu Gly
                245                 250                 255
Phe Ala Lys Lys Ala Ala Gly Ala Leu Lys Ala Gly Ser Pro Asp Ser
                260                 265                 270
Lys Ala Leu Ala Gln Glu Leu Arg Arg Leu Arg Asp Arg Asp Glu Gly
            275                 280                 285
Asn Val Leu Ala Asp Cys Val Glu Arg Gly Ala Ala Phe His His Ala
290                 295                 300
Gly Leu Ile Arg Gln Glu Arg Thr Ile Ile Glu Glu Gly Phe Arg Asn
305                 310                 315                 320
Gly Tyr Ile Glu Val Ile Ala Ala Thr Pro Thr Leu Ala Ala Gly Leu
                325                 330                 335
Asn Leu Pro Ala Arg Arg Val Ile Ile Arg Asp Tyr Asn Arg Phe Ala
                340                 345                 350
Ser Gly Leu Gly Met Val Pro Ile Pro Val Gly Glu Tyr His Gln Met
            355                 360                 365
Ala Gly Arg Ala Gly Arg Pro His Leu Asp Pro Tyr Gly Glu Ala Val
370                 375                 380
Leu Leu Ala Lys Asp Ala Pro Ser Val Glu Arg Leu Phe Glu Thr Phe
385                 390                 395                 400
Ile Asp Ala Glu Ala Glu Arg Val Asp Ser Gln Cys Val Asp Asp Ala
                405                 410                 415
Ser Leu Cys Ala His Ile Leu Ser Leu Ile Ala Thr Gly Phe Ala His
                420                 425                 430
Asp Gln Glu Ala Leu Ser Ser Phe Met Glu Arg Thr Phe Tyr Phe Phe
            435                 440                 445
Gln His Pro Lys Thr Arg Ser Leu Pro Arg Leu Val Ala Asp Ala Ile
450                 455                 460
Arg Phe Leu Thr Thr Ala Gly Met Val Glu Glu Arg Glu Asn Thr Leu
```

```
                465                 470                 475                 480
Ser Ala Thr Arg Leu Gly Ser Leu Val Ser Arg Leu Tyr Leu Asn Pro
                        485                 490                 495
Cys Thr Ala Arg Leu Ile Leu Asp Ser Leu Lys Ser Cys Lys Thr Pro
                        500                 505                 510
Thr Leu Ile Gly Leu Leu His Val Ile Cys Val Ser Pro Asp Met Gln
                        515                 520                 525
Arg Leu Tyr Leu Lys Ala Ala Asp Thr Gln Leu Leu Arg Thr Phe Leu
                        530                 535                 540
Phe Lys His Lys Asp Asp Leu Ile Leu Pro Leu Pro Phe Glu Gln Glu
545                         550                 555                 560
Glu Glu Glu Leu Trp Leu Ser Gly Leu Lys Thr Ala Leu Val Leu Thr
                        565                 570                 575
Asp Trp Ala Asp Glu Phe Ser Glu Gly Met Ile Glu Glu Arg Tyr Gly
                        580                 585                 590
Ile Gly Ala Gly Asp Leu Tyr Asn Ile Val Asp Ser Gly Lys Trp Leu
                        595                 600                 605
Leu His Gly Thr Glu Arg Leu Val Ser Val Glu Met Pro Glu Met Ser
        610                 615                 620
Gln Val Val Lys Thr Leu Ser Val Arg Val His His Gly Val Lys Ser
625                         630                 635                 640
Glu Leu Leu Pro Leu Val Ala Leu Arg Asn Ile Gly Arg Val Arg Ala
                        645                 650                 655
Arg Thr Leu Tyr Asn Ala Gly Tyr Pro Asp Pro Glu Ala Val Ala Arg
                        660                 665                 670
Ala Gly Leu Ser Thr Ile Ala Arg Ile Ile Gly Glu Gly Ile Ala Arg
                        675                 680                 685
Gln Val Ile Asp Glu Ile Thr Gly Val Lys Arg Ser Gly Ile His Ser
        690                 695                 700
Ser Asp Asp Asp Tyr Gln Gln Lys Thr Pro Glu Leu Leu Thr Asp Ile
705                         710                 715                 720
Pro Gly Ile Gly Lys Lys Met Ala Glu Lys Leu Gln Asn Ala Gly Ile
                        725                 730                 735
Ile Thr Val Ser Asp Leu Leu Thr Ala Asp Glu Val Leu Leu Ser Asp
                        740                 745                 750
Val Leu Gly Ala Ala Arg Ala Arg Lys Val Leu Ala Phe Leu Ser Asn
                        755                 760                 765
Ser Glu Lys Glu Asn Ser Ser Ser Asp Lys Thr Glu Glu Ile Pro Asp
        770                 775                 780
Thr Gln Lys Ile Arg Gly Gln Ser Ser Trp Glu Asp Phe Gly Cys
785                         790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15
Tyr Thr Asp Lys Asp Asn Tyr Tyr Val Leu Gly Ser Met Gly Glu Arg
                20                  25                  30
Trp Ala Gly Lys Gly Ala Glu Gln Leu Gly Leu Gln Gly Ser Val Asp
            35                  40                  45
```

```
Lys Asp Val Phe Thr Arg Leu Leu Glu Gly Arg Leu Pro Asp Gly Ala
 50                  55                  60

Asp Leu Ser Arg Met Gln Asp Gly Ser Asn Lys His Arg Pro Gly Tyr
 65                  70                  75                  80

Asp Leu Thr Phe Ser Ala Pro Lys Ser Val Ser Met Met Ala Met Leu
                 85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
            115                 120                 125

Gly Gln Ser Glu Thr Val Leu Thr Gly Asn Leu Val Met Ala Leu Phe
130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
            195                 200                 205

Glu Ala Leu Gly Tyr Glu Thr Glu Val Val Gly Lys His Gly Met Trp
210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
            275                 280                 285

Arg Ala Tyr Arg Asp Ala Ala Asp Gln Arg Thr Glu Ile Arg Thr Gln
290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Gly Gln Arg Glu Arg
            435                 440                 445

Val Ala Glu Leu Val Met Met Ala Arg Glu Gly Arg Glu Val Gln
450                 455                 460

Ile Ile Ala Ala Asp Arg Arg Ser Gln Met Asn Leu Lys Gln Asp Glu
```

```
            465                 470                 475                 480
        Arg Leu Ser Gly Glu Leu Ile Thr Gly Arg Arg Gln Leu Leu Glu Gly
                        485                 490                 495

Met Ala Phe Thr Pro Gly Ser Thr Val Ile Val Asp Gln Gly Glu Lys
                        500                 505                 510

Leu Ser Leu Lys Glu Thr Leu Thr Leu Leu Asp Gly Ala Ala Arg His
                        515                 520                 525

Asn Val Gln Val Leu Ile Thr Asp Ser Gly Gln Arg Thr Gly Thr Gly
                        530                 535                 540

Ser Ala Leu Met Ala Met Lys Asp Ala Gly Val Asn Thr Tyr Arg Trp
        545                 550                 555                 560

Gln Gly Gly Glu Gln Arg Pro Ala Thr Ile Ile Ser Glu Pro Asp Arg
                        565                 570                 575

Asn Val Arg Tyr Ala Arg Leu Ala Gly Asp Phe Ala Ala Ser Val Lys
                        580                 585                 590

Ala Gly Glu Glu Ser Val Ala Gln Val Ser Gly Val Arg Glu Gln Ala
                        595                 600                 605

Ile Leu Thr Gln Ala Ile Arg Ser Glu Leu Lys Thr Gln Gly Val Leu
                        610                 615                 620

Gly His Pro Glu Val Thr Met Thr Ala Leu Ser Pro Val Trp Leu Asp
        625                 630                 635                 640

Ser Arg Ser Arg Tyr Leu Arg Asp Met Tyr Arg Pro Gly Met Val Met
                        645                 650                 655

Glu Gln Trp Asn Pro Glu Thr Arg Ser His Asp Arg Tyr Val Ile Asp
                        660                 665                 670

Arg Val Thr Ala Gln Ser His Ser Leu Thr Leu Arg Asp Ala Gln Gly
                        675                 680                 685

Glu Thr Gln Val Val Arg Ile Ser Ser Leu Asp Ser Ser Trp Ser Leu
                        690                 695                 700

Phe Arg Pro Glu Lys Met Pro Val Ala Asp Gly Glu Arg Leu Arg Val
        705                 710                 715                 720

Thr Gly Lys Ile Pro Gly Leu Arg Val Ser Gly Gly Asp Arg Leu Gln
                        725                 730                 735

Val Ala Ser Val Ser Glu Asp Ala Met Thr Val Val Pro Gly Arg
                        740                 745                 750

Ala Glu Pro Ala Ser Leu Pro Val Ser Asp Ser Pro Phe Thr Ala Leu
                        755                 760                 765

Lys Leu Glu Asn Gly Trp Val Glu Thr Pro Gly His Ser Val Ser Asp
        770                 775                 780

Ser Ala Thr Val Phe Ala Ser Val Thr Gln Met Ala Met Asp Asn Ala
        785                 790                 795                 800

Thr Leu Asn Gly Leu Ala Arg Ser Gly Arg Asp Val Arg Leu Tyr Ser
                        805                 810                 815

Ser Leu Asp Glu Thr Arg Thr Ala Glu Lys Leu Ala Arg His Pro Ser
                        820                 825                 830

Phe Thr Val Val Ser Glu Gln Ile Lys Ala Arg Ala Gly Glu Thr Leu
                        835                 840                 845

Leu Glu Thr Ala Ile Ser Leu Gln Lys Ala Gly Leu His Thr Pro Ala
                        850                 855                 860

Gln Gln Ala Ile His Leu Ala Leu Pro Val Leu Glu Ser Lys Asn Leu
        865                 870                 875                 880

Ala Phe Ser Met Val Asp Leu Leu Thr Glu Ala Lys Ser Phe Ala Ala
                        885                 890                 895
```

```
Glu Gly Thr Gly Phe Thr Glu Leu Gly Gly Glu Ile Asn Ala Gln Ile
                900                 905                 910

Lys Arg Gly Asp Leu Leu Tyr Val Asp Val Ala Lys Gly Tyr Gly Thr
            915                 920                 925

Gly Leu Leu Val Ser Arg Ala Ser Tyr Glu Ala Glu Lys Ser Ile Leu
        930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Gln Gly
            980                 985                 990

Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
    1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260

Leu Asn Thr Ala Asn Ile Arg Asp Gly Glu Leu Arg Arg Leu Ser
    1265                1270                1275

Thr Trp Glu Lys Asn Pro Asp Ala Leu Ala Leu Val Asp Asn Val
    1280                1285                1290
```

```
Tyr His Arg Ile Ala Gly Ile Ser Lys Asp Asp Gly Leu Ile Thr
1295                1300                1305

Leu Gln Asp Ala Glu Gly Asn Thr Arg Leu Ile Ser Pro Arg Glu
1310                1315                1320

Ala Val Ala Glu Gly Val Thr Leu Tyr Thr Pro Asp Lys Ile Arg
1325                1330                1335

Val Gly Thr Gly Asp Arg Met Arg Phe Thr Lys Ser Asp Arg Glu
1340                1345                1350

Arg Gly Tyr Val Ala Asn Ser Val Trp Thr Val Thr Ala Val Ser
1355                1360                1365

Gly Asp Ser Val Thr Leu Ser Asp Gly Gln Gln Thr Arg Val Ile
1370                1375                1380

Arg Pro Gly Gln Glu Arg Ala Glu Gln His Ile Asp Leu Ala Tyr
1385                1390                1395

Ala Ile Thr Ala His Gly Ala Gln Gly Ala Ser Glu Thr Phe Ala
1400                1405                1410

Ile Ala Leu Glu Gly Thr Glu Gly Asn Arg Lys Leu Met Ala Gly
1415                1420                1425

Phe Glu Ser Ala Tyr Val Ala Leu Ser Arg Met Lys Gln His Val
1430                1435                1440

Gln Val Tyr Thr Asp Asn Arg Gln Gly Trp Thr Asp Ala Ile Asn
1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530

Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile
1655                1660                1665

Val Arg Lys Met Ala Glu Asn Lys Pro Asp Leu Pro Asp Gly Lys
1670                1675                1680

Thr Glu Leu Ala Val Arg Asp Ile Ala Gly Gln Glu Arg Asp Arg
```

```
                    1685                1690                1695

Ser  Ala  Ile  Ser  Glu  Arg  Glu  Thr  Ala  Leu  Pro  Glu  Ser  Val  Leu
           1700                1705                1710

Arg  Glu  Ser  Gln  Arg  Glu  Arg  Glu  Ala  Val  Arg  Glu  Val  Ala  Arg
      1715                1720                1725

Glu  Asn  Leu  Leu  Gln  Glu  Arg  Leu  Gln  Gln  Met  Glu  Arg  Asp  Met
 1730                1735                1740

Val  Arg  Asp  Leu  Gln  Lys  Glu  Lys  Thr  Leu  Gly  Gly  Asp
 1745                1750                1755

<210> SEQ ID NO 23
<211> LENGTH: 726
<212> TYPE: PRT
<213> ORGANISM: Methanococcoides burtonii

<400> SEQUENCE: 23

Met  Ser  Asp  Lys  Pro  Ala  Phe  Met  Lys  Tyr  Phe  Thr  Gln  Ser  Cys
 1                 5                  10                  15

Tyr  Pro  Asn  Gln  Gln  Glu  Ala  Met  Asp  Arg  Ile  His  Ser  Ala  Leu  Met
            20                  25                  30

Gln  Gln  Gln  Leu  Val  Leu  Phe  Glu  Gly  Ala  Cys  Gly  Thr  Gly  Lys  Thr
       35                  40                  45

Leu  Ser  Ala  Leu  Val  Pro  Ala  Leu  His  Val  Gly  Lys  Met  Leu  Gly  Lys
 50                  55                  60

Thr  Val  Ile  Ile  Ala  Thr  Asn  Val  His  Gln  Gln  Met  Val  Gln  Phe  Ile
 65                  70                  75                  80

Asn  Glu  Ala  Arg  Asp  Ile  Lys  Lys  Val  Gln  Asp  Val  Lys  Val  Ala  Val
                 85                  90                  95

Ile  Lys  Gly  Lys  Thr  Ala  Met  Cys  Pro  Gln  Glu  Ala  Asp  Tyr  Glu  Glu
            100                 105                 110

Cys  Ser  Val  Lys  Arg  Glu  Asn  Thr  Phe  Glu  Leu  Met  Glu  Thr  Glu  Arg
       115                 120                 125

Glu  Ile  Tyr  Leu  Lys  Arg  Gln  Glu  Leu  Asn  Ser  Ala  Arg  Asp  Ser  Tyr
 130                 135                 140

Lys  Lys  Ser  His  Asp  Pro  Ala  Phe  Val  Thr  Leu  Arg  Asp  Glu  Leu  Ser
 145                 150                 155                 160

Lys  Glu  Ile  Asp  Ala  Val  Glu  Glu  Lys  Ala  Arg  Gly  Leu  Arg  Asp  Arg
                 165                 170                 175

Ala  Cys  Asn  Asp  Leu  Tyr  Glu  Val  Leu  Arg  Ser  Asp  Ser  Glu  Lys  Phe
            180                 185                 190

Arg  Glu  Trp  Leu  Tyr  Lys  Glu  Val  Arg  Ser  Pro  Glu  Glu  Ile  Asn  Asp
       195                 200                 205

His  Ala  Ile  Lys  Asp  Gly  Met  Cys  Gly  Tyr  Glu  Leu  Val  Lys  Arg  Glu
 210                 215                 220

Leu  Lys  His  Ala  Asp  Leu  Leu  Ile  Cys  Asn  Tyr  His  His  Val  Leu  Asn
 225                 230                 235                 240

Pro  Asp  Ile  Phe  Ser  Thr  Val  Leu  Gly  Trp  Ile  Glu  Lys  Glu  Pro  Gln
                 245                 250                 255

Glu  Thr  Ile  Val  Ile  Phe  Asp  Glu  Ala  His  Asn  Leu  Glu  Ser  Ala  Ala
            260                 265                 270

Arg  Ser  His  Ser  Ser  Leu  Ser  Leu  Thr  Glu  His  Ser  Ile  Glu  Lys  Ala
       275                 280                 285

Ile  Thr  Glu  Leu  Glu  Ala  Asn  Leu  Asp  Leu  Leu  Ala  Asp  Asp  Asn  Ile
 290                 295                 300
```

```
His Asn Leu Phe Asn Ile Phe Leu Glu Val Ile Ser Asp Thr Tyr Asn
305                 310                 315                 320

Ser Arg Phe Lys Phe Gly Glu Arg Glu Val Arg Lys Asn Trp Tyr
            325                 330                 335

Asp Ile Arg Ile Ser Asp Pro Tyr Glu Arg Asn Asp Ile Val Arg Gly
                340                 345                 350

Lys Phe Leu Arg Gln Ala Lys Gly Asp Phe Gly Lys Asp Asp Ile
            355                 360                 365

Gln Ile Leu Leu Ser Glu Ala Ser Glu Leu Gly Ala Lys Leu Asp Glu
                370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
                420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
            515                 520                 525

Ser Ile Glu Asn Ser Lys Gly Asn Val Ile Leu Phe Phe Gln Ser Ala
530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
                580                 585                 590

Tyr Leu Trp Gly Thr Leu Ser Glu Gly Ile Asp Tyr Arg Asp Gly Arg
            595                 600                 605

Gly Arg Thr Val Ile Ile Gly Val Gly Tyr Pro Ala Leu Asn Asp
610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
                675                 680                 685

Lys Phe Ser Val Phe Glu Val Phe Pro Pro Ala Glu Arg Ser Glu Phe
            690                 695                 700

Val Asp Val Asp Pro Glu Lys Val Lys Tyr Ser Leu Met Asn Phe Phe
705                 710                 715                 720

Met Asp Asn Asp Glu Gln
```

<210> SEQ ID NO 24
<211> LENGTH: 439
<212> TYPE: PRT
<213> ORGANISM: Enterobacteria phage T4

<400> SEQUENCE: 24

```
Met Thr Phe Asp Asp Leu Thr Glu Gly Gln Lys Asn Ala Phe Asn Ile
  1               5                  10                  15

Val Met Lys Ala Ile Lys Glu Lys Lys His Val Thr Ile Asn Gly
                 20                  25                  30

Pro Ala Gly Thr Gly Lys Thr Leu Thr Lys Phe Ile Ile Glu Ala
             35                  40                  45

Leu Ile Ser Thr Gly Glu Thr Gly Ile Ile Leu Ala Ala Pro Thr His
         50                  55                  60

Ala Ala Lys Lys Ile Leu Ser Lys Leu Ser Gly Lys Glu Ala Ser Thr
 65                  70                  75                  80

Ile His Ser Ile Leu Lys Ile Asn Pro Val Thr Tyr Glu Glu Asn Val
                 85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365
```

-continued

```
Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
                420                 425                 430

Arg Tyr Asp Val Phe Tyr Val
            435

<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
                260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
    290                 295                 300
```

```
Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Gln Ala Val Ala Ser Ala Val
            340                 345                 350

Arg His Leu Ser Gln Arg Glu Ala Ala Phe Glu Arg Thr Ala Leu Tyr
                355                 360                 365

Lys Ala Ala Leu Asp Phe Gly Leu Pro Thr Thr Ile Ala Asp Val Glu
370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
                420                 425                 430

Ala Ile Thr Pro Gln Lys Ala Ala Ser Val Gln Ala Ala Ala Leu
            435                 440                 445

Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
                500                 505                 510

Gln Met Leu Glu Arg Asp Thr Gly Ile Gly Ser Gln Thr Leu Ala Arg
            515                 520                 525

Phe Leu Gly Gly Trp Asn Lys Leu Leu Asp Asp Pro Gly Asn Val Ala
            530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
            595                 600                 605

Arg Ala Gly Ile Ala Arg Ala Glu Met Ala Thr Asn Leu Arg Ala Arg
610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
            675                 680                 685

Ala Val Asn Ala Ala Val Gln Gln Gly Leu Leu Ala Ser Arg Glu Ile
            690                 695                 700

Gly Pro Ala Lys Met Lys Leu Glu Val Leu Asp Arg Val Asn Thr Thr
705                 710                 715                 720
```

Arg Glu Glu Leu Arg His Leu Pro Ala Tyr Arg Ala Gly Arg Val Leu
            725                 730                 735

Glu Val Ser Arg Lys Gln Gln Ala Leu Gly Leu Phe Ile Gly Glu Tyr
        740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 26
<211> LENGTH: 605
<212> TYPE: PRT
<213> ORGANISM: Escherichia coli

<400> SEQUENCE: 26

Met Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Asp
                20                  25                  30

Thr Glu Thr Asp Ser Leu Asp Asn Ile Ser Ala Asn Leu Val Gly Leu
            35                  40                  45

Ser Phe Ala Ile Glu Pro Gly Val Ala Ala Tyr Ile Pro Val Ala His
        50                  55                  60

Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
                85                  90                  95

Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
        115                 120                 125

-continued

```
Val Ala Gly Arg His Asp Met Asp Ser Leu Ala Glu Arg Trp Leu Lys
            130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
        195                 200                 205

Pro Leu Val Pro Val Leu Ser Arg Ile Glu Arg Asn Gly Val Lys Ile
210                 215                 220

Asp Pro Lys Val Leu His Asn His Ser Glu Glu Leu Thr Leu Arg Leu
225                 230                 235                 240

Ala Glu Leu Glu Lys Lys Ala His Glu Ile Ala Gly Glu Glu Phe Asn
                245                 250                 255

Leu Ser Ser Thr Lys Gln Leu Gln Thr Ile Leu Phe Glu Lys Gln Gly
            260                 265                 270

Ile Lys Pro Leu Lys Lys Thr Pro Gly Gly Ala Pro Ser Thr Ser Glu
        275                 280                 285

Glu Val Leu Glu Glu Leu Ala Leu Asp Tyr Pro Leu Pro Lys Val Ile
290                 295                 300

Leu Glu Tyr Arg Gly Leu Ala Lys Leu Lys Ser Thr Tyr Thr Asp Lys
305                 310                 315                 320

Leu Pro Leu Met Ile Asn Pro Lys Thr Gly Arg Val His Thr Ser Tyr
                325                 330                 335

His Gln Ala Val Thr Ala Thr Gly Arg Leu Ser Ser Thr Asp Pro Asn
            340                 345                 350

Leu Gln Asn Ile Pro Val Arg Asn Glu Glu Gly Arg Arg Ile Arg Gln
        355                 360                 365

Ala Phe Ile Ala Pro Glu Asp Tyr Val Ile Val Ser Ala Asp Tyr Ser
370                 375                 380

Gln Ile Glu Leu Arg Ile Met Ala His Leu Ser Arg Asp Lys Gly Leu
385                 390                 395                 400

Leu Thr Ala Phe Ala Glu Gly Lys Asp Ile His Arg Ala Thr Ala Ala
                405                 410                 415

Glu Val Phe Gly Leu Pro Leu Glu Thr Val Thr Ser Glu Gln Arg Arg
            420                 425                 430

Ser Ala Lys Ala Ile Asn Phe Gly Leu Ile Tyr Gly Met Ser Ala Phe
        435                 440                 445

Gly Leu Ala Arg Gln Leu Asn Ile Pro Arg Lys Glu Ala Gln Lys Tyr
450                 455                 460

Met Asp Leu Tyr Phe Glu Arg Tyr Pro Gly Val Leu Glu Tyr Met Glu
465                 470                 475                 480

Arg Thr Arg Ala Gln Ala Lys Glu Gln Gly Tyr Val Glu Thr Leu Asp
                485                 490                 495

Gly Arg Arg Leu Tyr Leu Pro Asp Ile Lys Ser Ser Asn Gly Ala Arg
            500                 505                 510

Arg Ala Ala Ala Glu Arg Ala Ala Ile Asn Ala Pro Met Gln Gly Thr
        515                 520                 525

Ala Ala Asp Ile Ile Lys Arg Ala Met Ile Ala Val Asp Ala Trp Leu
530                 535                 540
```

```
Gln Ala Glu Gln Pro Arg Val Arg Met Ile Met Gln Val His Asp Glu
545                 550                 555                 560

Leu Val Phe Glu Val His Lys Asp Asp Val Asp Ala Val Ala Lys Gln
                565                 570                 575

Ile His Gln Leu Met Glu Asn Cys Thr Arg Leu Asp Val Pro Leu Leu
            580                 585                 590

Val Glu Val Gly Ser Gly Glu Asn Trp Asp Gln Ala His
        595                 600                 605

<210> SEQ ID NO 27
<211> LENGTH: 606
<212> TYPE: DNA
<213> ORGANISM: Artificial Sequence
<220> FEATURE:
<223> OTHER INFORMATION: Synthetic Polynucleotide

<400> SEQUENCE: 27
gccatcagat tgtgtttgtt agtcgctttt ttttttttgga attttttttt tggaattttt      60
tttttgacgc tcagtaatgt gacgatagct gaaaactgta cgataaacgg tacgctgagg     120
gcggaaaaaa tcgtcgggga cattgtaaag gcggcgagcg cggcttttcc gcgccagcgt     180
gaaagcagtg tggactggcc gtcaggtacc cgtactgtca ccgtgaccga tgaccatcct     240
tttgatcgcc agatagtggt gcttccgctg acgtttcgcg gaagtaagcg tactgtcagc     300
ggcaggacaa cgtattcgat gtgttatctg aaagtactga tgaacggtgc ggtgatttat     360
gatggcgcgg cgaacgaggc ggtacaggtg ttctcccgta ttgttgacat gccagcgggt     420
cggggaaacg tgatcctgac gttcacgctt acgtccacac ggcattcggc agatattccg     480
ccgtatacgt ttgccagcga tgtgcaggtt atggtgatta agaaacaggc gctgggcatc     540
agcgtggtct gagtgtgaaa aaaaggtac caaaaaaaac atcgtcgtga gtagtgaacc     600
gtaagc                                                                606

<210> SEQ ID NO 28
<211> LENGTH: 91
<212> TYPE: DNA
<213> ORGANISM: Artificial Sequence
<220> FEATURE:
<223> OTHER INFORMATION: Synthetic Polynucleotide

<400> SEQUENCE: 28
gccatcagat tgtgtttgtt agtcgctttt ttttttttgga attttttttt tggaattttt      60
tttttgacgc tcagtaatgt gacgatagct g                                     91

<210> SEQ ID NO 29
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 29
gcttacggtt cactactcac gacgatgttt tttttggtac cttttttttc acactcagac      60
cacgctgatg c                                                           71

<210> SEQ ID NO 30
<211> LENGTH: 97
<212> TYPE: DNA
<213> ORGANISM: Artificial Sequence
<220> FEATURE:
<223> OTHER INFORMATION: Synthetic Polynucleotide
```

```
<400> SEQUENCE: 30
tttttttttt tttttttttt tttttttttt tttttttttt tttttttttt tttttttttt      60
tttttttttt ggttgtttct gttggtgctg atattgc                               97

<210> SEQ ID NO 31
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 31
gccatcagat tgtgtttgtt agtcgct                                          27

<210> SEQ ID NO 32
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 32
gcttatgttt tcataagctt ttgagctctt ttgcttacgg ttcactactc acgacgatg       59

<210> SEQ ID NO 33
<211> LENGTH: 638
<212> TYPE: DNA
<213> ORGANISM: Artificial Sequence
<220> FEATURE:
<223> OTHER INFORMATION: Synthetic Polynucleotide

<400> SEQUENCE: 33
gccatcagat tgtgtttgtt agtcgctttt tttttttgga atttttttt tggaatttt        60 tttttgacgc tcagtaatgt gacgatagct gaaaactgta cgataaacgg tacgctgagg     120
gcggaaaaaa tcgtcgggga cattgtaaag gcggcgagcg cggcttttcc gcgccagcgt     180
gaaagcagtg tggactggcc gtcaggtacc cgtactgtca ccgtgaccga tgaccatcct     240
tttgatcgcc agatagtggt gcttccgctg acgtttgcg gaagtaagcg tactgtcagc      300
ggcaggacaa cgtattcgat gtgttatctg aaagtactga tgaacggtgc ggtgatttat     360
gatggcgcgg cgaacgaggc ggtacaggtg ttctcccgta ttgttgacat gccagcgggt     420
cggggaaacg tgatcctgac gttcacgctt acgtccacac ggcattcggc agatattccg     480
ccgtatacgt tgccagcga tgtgcaggtt atggtgatta gaaacaggc gctgggcatc       540 agcgtggtct gagtgtgaaa aaaaggtac caaaaaaaac atcgtcgtga gtagtgaacc      600
gtaagcaaaa gagctcaaaa gcttatgaaa acataagc                             638

<210> SEQ ID NO 34
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 34
tttttttttt tttttttttt tttttttttt tttttttttt tttttggtt gtttctgttg       60 gtgctgatat tgc                                                         73

<210> SEQ ID NO 35
```

<211> LENGTH: 3447
<212> TYPE: DNA
<213> ORGANISM: Artificial Sequence
<220> FEATURE:
<223> OTHER INFORMATION: Synthetic Polynucleotide

<400> SEQUENCE: 35

| | | | | | |
|---|---|---|---|---|---|
| gcgctaacaa | cctcctgccg | ttttgcccgt | gcatatcggt | cacgaacaaa | tctgattact | 60 |
| aaacacagta | gcctggattt | gttctatcag | taatcgacct | tattcctaat | taaatagagc | 120 |
| aaatccccctt | attggggta | agacatgaag | atgccagaaa | acatgacct | gttggccgcc | 180 |
| attctcgcgg | caaaggaaca | aggcatcggg | gcaatccttg | cgtttgcaat | ggcgtacctt | 240 |
| cgcggcagat | ataatggcgg | tgcgtttaca | aaaacagtaa | tcgacgcaac | gatgtgcgcc | 300 |
| attatcgcct | agttcattcg | tgaccttctc | gacttcgccg | gactaagtag | caatctcgct | 360 |
| tatataacga | gcgtgtttat | cggctacatc | ggtactgact | cgattggttc | gcttatcaaa | 420 |
| cgcttcgctg | ctaaaaaagc | cggagtagaa | gatggtagaa | atcaataatc | aacgtaaggc | 480 |
| gttcctcgat | atgctggcgt | ggtcggaggg | aactgataac | ggacgtcaga | aaaccagaaa | 540 |
| tcatggttat | gacgtcattg | taggcggaga | gctatttact | gattactccg | atcaccctcg | 600 |
| caaacttgtc | acgctaaacc | caaaactcaa | atcaacaggc | gccggacgct | accagcttct | 660 |
| ttcccgttgg | tgggatgcct | accgcaagca | gcttggcctg | aaagacttct | ctccgaaaag | 720 |
| tcaggacgct | gtggcattgc | agcagattaa | ggagcgtggc | gctttaccta | tgattgatcg | 780 |
| tggtgatatc | cgtcaggcaa | tcgaccgttg | cagcaatatc | tgggcttcac | tgccgggcgc | 840 |
| tggttatggt | cagttcgagc | ataaggctga | cagcctgatt | gcaaaattca | agaagcggg | 900 |
| cggaacggtc | agagagattg | atgtatgagc | agagtcaccg | cgattatctc | cgctctggtt | 960 |
| atctgcatca | tcgtctgcct | gtcatgggct | gttaatcatt | accgtgataa | cgccattacc | 1020 |
| tacaaagccc | agcgcgacaa | aaatgccaga | gaactgaagc | tggcgaacgc | ggcaattact | 1080 |
| gacatgcaga | tgcgtcagcg | tgatgttgct | gcgctcgatg | caaaatacac | gaaggagtta | 1140 |
| gctgatgcta | agctgaaaa | tgatgctctg | cgtgatgatg | ttgccgctgg | tcgtcgtcgg | 1200 |
| ttgcacatca | aagcagtctg | tcagtcagtg | cgtgaagcca | ccaccgcctc | cggcgtggat | 1260 |
| aatgcagcct | cccccccgact | ggcagacacc | gctgaacggg | attatttcac | cctcagagag | 1320 |
| aggctgatca | ctatgcaaaa | acaactggaa | ggaacccaga | agtatattaa | tgagcagtgc | 1380 |
| agatagagtt | gcccatatcg | atgggcaact | catgcaatta | ttgtgagcaa | tacacacgcg | 1440 |
| cttccagcgg | agtataaatg | cctaaagtaa | taaaaccgag | caatccattt | acgaatgttt | 1500 |
| gctgggtttc | tgttttaaca | acattttctg | cgccgccaca | aattttggct | gcatcgacag | 1560 |
| ttttcttctg | cccaattcca | gaaacgaaga | atgatgggt | gatggtttcc | tttggtgcta | 1620 |
| ctgctgccgg | tttgttttga | acagtaaacg | tctgttgagc | acatcctgta | ataagcaggg | 1680 |
| ccagcgcagt | agcgagtagc | atttttttca | tggtgttatt | cccgatgctt | tttgaagttc | 1740 |
| gcagaatcgt | atgtgtagaa | aattaaacaa | accctaaaca | atgagttgaa | atttcatatt | 1800 |
| gttaatattt | attaatgtat | gtcaggtgcg | atgaatcgtc | attgtattcc | cggattaact | 1860 |
| atgtccacag | ccctgacggg | gaacttctct | gcgggagtgt | ccgggaataa | ttaaaacgat | 1920 |
| gcacacaggg | tttagcgcgt | acacgtattg | cattatgcca | acgccccggt | gctgacacgg | 1980 |
| aagaaaccgg | acgttatgat | ttagcgtgga | aagatttgtg | tagtgttctg | aatgctctca | 2040 |
| gtaaatagta | atgaattatc | aaaggtatag | taatatcttt | tatgttcatg | gatatttgta | 2100 |
| acccatcgga | aaactcctgc | tttagcaaga | ttttccctgt | attgctgaaa | tgtgatttct | 2160 |

```
cttgatttca acctatcata ggacgtttct ataagatgcg tgtttcttga gaatttaaca    2220
tttacaacct ttttaagtcc ttttattaac acgtgttat cgttttctaa cacgatgtga     2280
atattatctg tggctagata gtaaatataa tgtgagacgt tgtgacgttt tagttcagaa    2340
taaaacaatt cacagtctaa atcttttcgc acttgatcga atatttcttt aaaaatggca    2400
acctgagcca ttggtaaaac cttccatgtg atacgagggc gcgtagtttg cattatcgtt    2460
tttatcgttt caatctggtc tgacctcctt gtgttttgtt gatgatttat gtcaaatatt    2520
aggaatgttt tcacttaata gtattggttg cgtaacaaag tgcggtcctg ctggcattct    2580
ggagggaaat acaaccgaca gatgtatgta aggccaacgt gctcaaatct tcatacagaa    2640
agatttgaag taatatttta accgctagat gaagagcaag cgcatggagc gacaaaatga    2700
ataaagaaca atctgctgat gatccctccg tggatctgat tcgtgtaaaa aatatgctta    2760
atagcaccat ttctatgagt taccctgatg ttgtaattgc atgtatagaa cataaggtgt    2820
ctctggaagc attcagagca attgaggcag cgttggtgaa gcacgataat aatatgaagg    2880
attattccct ggtggttgac tgatcaccat aactgctaat cattcaaact atttagtctg    2940
tgacagagcc aacacgcagt ctgtcactgt caggaaagtg gtaaaactgc aactcaatta    3000
ctgcaatgcc ctcgtaatta agtgaattta caatatcgtc ctgttcggag ggaagaacgc    3060
gggatgttca ttcttcatca cttttaattg atgtatatgc tctcttttct gacgttagtc    3120
tccgacggca ggcttcaatg acccaggctg agaaattccc ggaccctttt tgctcaagag    3180
cgatgttaat ttgttcaatc atttggttag gaaagcggat gttgcgggtt gttgttctgc    3240
gggttctgtt cttcgttgac atgaggttgc cccgtattca gtgtcgctga tttgtattgt    3300
ctgaagttgt ttttacgtta agttgatgca gatcaattaa tacgatacct gcgtcataat    3360
tgattatttg acgtggtttg atggcctcca cgcacgttgt gatatgtaga tgataatcat    3420 tatcactttta cgggtccttt ccggtga                                       3447
```

<210> SEQ ID NO 36
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 36

```
ggttgtttct gttggtgctg atattgc                                          27
```

<210> SEQ ID NO 37
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 37

```
gccatcagat tgtgtttgtt agtcgctttt ttttttttgga atttttttttt tggaattttt    60 tttttgcgct aacaacctcc tgccgttttg cccgtgcata tcggtcacga acaaatctga    120
ttactaaaca cagtagcctg gatttgttct atcagtaatc gaccttattc ctaattaaat    180
agagcaaatc cccttattgg gggtaagaca tgaagatgcc agaaaaacat gacctgttgg    240
ccgccattct cgcggcaaag gaacaaggca tcggggcaat ccttgcgttt gcaatggcgt    300
accttcgcgg cagatataat ggcggtgcgt ttacaaaaac agtaatcgac gcaacgatgt    360
```

-continued

```
gcgccattat cgcctagttc attcgtgacc ttctcgactt cgccggacta agtagcaatc    420
tcgcttatat aacgagcgtg tttatcggct acatcggtac tgactcgatt ggttcgctta    480
tcaaacgctt cgctgctaaa aaagccggag tagaagatgg tagaaatcaa taatcaacgt    540
aaggcgttcc tcgatatgct ggcgtggtcg gagggaactg ataacggacg tcagaaaacc    600
agaaatcatg gttatgacgt cattgtaggc ggagagctat ttactgatta ctccgatcac    660
cctcgcaaac ttgtcacgct aaacccaaaa ctcaaatcaa caggcgccgg acgctaccag    720
cttctttccc gttggtggga tgcctaccgc aagcagcttg gcctgaaaga cttctctccg    780
aaaagtcagg acgctgtggc attgcagcag attaaggagc gtggcgcttt acctatgatt    840
gatcgtggtg atatccgtca ggcaatcgac cgttgcagca atatctgggc ttcactgccg    900
ggcgctggtt atggtcagtt cgagcataag gctgacagcc tgattgcaaa attcaaagaa    960
gcgggcggaa cggtcagaga gattgatgta tgagcagagt caccgcgatt atctccgctc   1020
tggttatctg catcatcgtc tgcctgtcat gggctgttaa tcattaccgt gataacgcca   1080
ttacctacaa agcccagcgc gacaaaaatg ccagagaact gaagctggcg aacgcggcaa   1140
ttactgacat gcagatgcgt cagcgtgatg ttgctgcgct cgatgcaaaa tacacgaagg   1200
agttagctga tgctaaagct gaaaatgatg ctctgcgtga tgatgttgcc gctggtcgtc   1260
gtcggttgca catcaaagca gtctgtcagt cagtgcgtga agccaccacc gcctccggcg   1320
tggataatgc agcctccccc cgactggcag acaccgctga acgggattat ttcaccctca   1380
gagagaggct gatcactatg caaaaacaac tggaaggaac ccagaagtat attaatgagc   1440
agtgcagata gagttgccca tatcgatggg caactcatgc aattattgtg agcaatacac   1500
acgcgcttcc agcggagtat aaatgcctaa agtaataaaa ccgagcaatc catttacgaa   1560
tgtttgctgg gtttctgttt taacaacatt ttctgcgccg ccacaaattt tggctgcatc   1620
gacagttttc ttctgcccaa ttccagaaac gaagaaatga tgggtgatgg tttcctttgg   1680
tgctactgct gccggtttgt tttgaacagt aaacgtctgt tgagcacatc ctgtaataag   1740
cagggccagc gcagtagcga gtagcatttt tttcatggtg ttattcccga tgctttttga   1800
agttcgcaga atcgtatgtg tagaaaatta aacaaaccct aaacaatgag ttgaaatttc   1860
atattgttaa tatttattaa tgtatgtcag gtgcgatgaa tcgtcattgt attcccggat   1920
taactatgtc cacagccctg acggggaact tctctgcggg agtgtccggg aataattaaa   1980
acgatgcaca cagggtttag cgcgtacacg tattgcatta tgccaacgcc ccggtgctga   2040
cacggaagaa accggacgtt atgatttagc gtggaaagat ttgtgtagtg ttctgaatgc   2100
tctcagtaaa tagtaatgaa ttatcaaagg tatagtaata tcttttatgt tcatggatat   2160
ttgtaaccca tcggaaaact cctgctttag caagattttc cctgtattgc tgaaatgtga   2220
tttctcttga tttcaaccta tcataggacg tttctataag atgcgtgttt cttgagaatt   2280
taacatttac aacctttta agtccttta ttaacacggt gttatcgttt ctaacacga   2340 tgtgaatatt atctgtggct agatagtaaa tataatgtga gacgttgtga cgttttagtt   2400
cagaataaaa caattcacag tctaaatctt ttcgcacttg atcgaatatt tctttaaaaa   2460
tggcaacctg agccattggt aaaaccttcc atgtgatacg agggcgcgta gtttgcatta   2520 tcgttttat cgtttcaatc tggtctgacc tccttgtgtt ttgttgatga tttatgtcaa   2580
atattaggaa tgttttcact taatagtatt ggttgcgtaa caagtgcgg tcctgctggc   2640 attctggagg gaaatacaac cgacagatgt atgtaaggcc aacgtgctca atcttcata   2700 cagaaagatt tgaagtaata ttttaaccgc tagatgaaga gcaagcgcat ggagcgacaa   2760
```

| | |
|---|---:|
| aatgaataaa gaacaatctg ctgatgatcc ctccgtggat ctgattcgtg taaaaaatat | 2820 |
| gcttaatagc accatttcta tgagttaccc tgatgttgta attgcatgta tagaacataa | 2880 |
| ggtgtctctg gaagcattca gagcaattga ggcagcgttg gtgaagcacg ataataatat | 2940 |
| gaaggattat tccctggtgg ttgactgatc accataactg ctaatcattc aaactattta | 3000 |
| gtctgtgaca gagccaacac gcagtctgtc actgtcagga aagtggtaaa actgcaactc | 3060 |
| aattactgca atgccctcgt aattaagtga atttacaata tcgtcctgtt cggagggaag | 3120 |
| aacgcgggat gttcattctt catcactttt aattgatgta tatgctctct tttctgacgt | 3180 |
| tagtctccga cggcaggctt caatgaccca ggctgagaaa ttcccggacc cttttttgctc | 3240 |
| aagagcgatg ttaatttgtt caatcatttg gttaggaaag cggatgttgc gggttgttgt | 3300 |
| tctgcgggtt ctgttcttcg ttgacatgag gttgccccgt attcagtgtc gctgatttgt | 3360 |
| attgtctgaa gttgttttta cgttaagttg atgcagatca attaatacga tacctgcgtc | 3420 |
| ataattgatt atttgacgtg gtttgatggc ctccacgcac gttgtgatat gtagatgata | 3480 |
| atcattatca ctttacgggt cctttccggt gaaaaaaaag gtaccaaaaa aaacatcgtc | 3540 |
| gtgagtagtg aaccgtaagc | 3560 |

<210> SEQ ID NO 38
<211> LENGTH: 1214
<212> TYPE: DNA
<213> ORGANISM: Artificial Sequence
<220> FEATURE:
<223> OTHER INFORMATION: Synthetic Polynucleotide

<400> SEQUENCE: 38

| | |
|---|---:|
| gccatcagat tgtgtttgtt agtcgctttt ttttttgga attttttttt tggaatttt | 60 |
| tttttgacgc tcagtaatgt gacgatagct gaaaactgta cgataaacgg tacgctgagg | 120 |
| gcggaaaaaa tcgtcgggga cattgtaaag gcggcgagcg cggcttttcc gcgccagcgt | 180 |
| gaaagcagtg tggactggcc gtcaggtacc cgtactgtca ccgtgaccga tgaccatcct | 240 |
| tttgatcgcc agatagtggt gcttccgctg acgtttcgcg gaagtaagcg tactgtcagc | 300 |
| ggcaggacaa cgtattcgat gtgttatctg aaagtactga tgaacggtgc ggtgatttat | 360 |
| gatggcgcgg cgaacgaggc ggtacaggtg ttctcccgta ttgttgacat gccagcgggt | 420 |
| cggggaaacg tgatcctgac gttcacgctt acgtccacac ggcattcggc agatattccg | 480 |
| ccgtatacgt ttgccagcga tgtgcaggtt atggtgatta agaaacaggc gctgggcatc | 540 |
| agcgtggtct gagtgtgcat cgtcgtgagt agtgaaccgt aagcaaaaga gctcaaaagc | 600 |
| ttatgaaaac ataagctttt gagctctttt gcttacggtt cactactcac gacgatgcac | 660 |
| actcagacca cgctgatgcc cagcgcctgt ttcttaatca ccataacctg cacatcgctg | 720 |
| gcaaacgtat acggcggaat atctgccgaa tgccgtgtgg acgtaagcgt gaacgtcagg | 780 |
| atcacgtttc cccgacccgc tggcatgtca acaatacggg agaacacctg taccgcctcg | 840 |
| ttcgccgcgc catcataaat caccgcaccg ttcatcagta ctttcagata acacatcgaa | 900 |
| tacgttgtcc tgccgctgac agtacgctta cttccgcgaa acgtcagcgg aagcaccact | 960 |
| atctggcgat caaaaggatg gtcatcggtc acggtgacag tacgggtacc tgacggccag | 1020 |
| tccacactgc tttcacgctg gcgcggaaaa gccgcgctcg ccgcctttac aatgtccccg | 1080 |
| acgatttttt ccgcccctcag cgtaccgttt atcgtacagt tttcagctat cgtcacatta | 1140 |
| ctgagcgtca aaaaaaaaat tccaaaaaaa aaattccaaa aaaaaaagc gactaacaaa | 1200 |

```
cacaatctga tggc                                              1214

<210> SEQ ID NO 39
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 39
tttttttttt tttttttttt tttttttttt tttttttttt tttttttttt ggttgtttct    60
gttggtgctg atattgc                                                   77

<210> SEQ ID NO 40
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 40
gacgctcagt aatgtgacga tatacgctga tgaccatcct tttgatcgcc agatagtggt    60
gcttccgctg acgtttcgcg gaagtaagcg tactgtcgtt ttcgacagta cgcttacttc   120
cgcgaaacgt cagcggaagc accactatct ggcgatcaaa aggatggtca tcagcgtata   180
tcgtcacatt actgagcgtc aaaa                                          204

<210> SEQ ID NO 41
<211> LENGTH: 616
<212> TYPE: DNA
<213> ORGANISM: Artificial Sequence
<220> FEATURE:
<223> OTHER INFORMATION: Synthetic Polynucleotide

<400> SEQUENCE: 41
gccatcagat tgtgtttgtt agtcgctttt ttttttggaa attttttttt tggaattttt    60
tttttgacgc tcagtaatgt gacgatagct gaaaactgta cgataaacgg tacgctgagg   120
gcggaaaaaa tcgtcgggga cattgtaaag gcggcgagcg cggcttttcc gcgccagcgt   180
gaaagcagtg tggactggcc gtcaggtacc cgtactgtca ccgtgaccga tgaccatcct   240
tttgatcgcc agatagtggt gcttccgctg acgtttcgcg gaagtaagcg tactgtcagc   300
ggcaggacaa cgtattcgat gtgttatctg aaagtactga tgaacggtgc ggtgatttat   360
gatggcgcgg cgaacgaggc ggtacaggtg ttctcccgta ttgttgacat gccagcgggt   420
cggggaaacg tgatcctgac gttcacgctt acgtccacac ggcattcggc agatattccg   480
ccgtatacgt ttgccagcga tgtgcaggtt atggtgatta agaaacaggc gctgggcatc   540
agcgtggtct gagtgtgcat cgtcgtgagt agtgaaccgt aagcaaaaga gctcaaaagc   600
ttatgaaaac ataagc                                                   616

<210> SEQ ID NO 42
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 42
gcaatatcag caccaacaga aacaacctt                                      29
```

<210> SEQ ID NO 43
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 43
gatcggaaga gcgcatcgtc gtgagtagtg aaccgtaagc gcatgcatca          50

<210> SEQ ID NO 44
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 44
cgctcttccg atct                                                 14

<210> SEQ ID NO 45
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 45
tttttttttt tt                                                   12

<210> SEQ ID NO 46
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 46
gcttacggtt cactactcac gacgatg                                   27

<210> SEQ ID NO 47
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 47
gcttacggtt cactactcac gacgatgttt ttttggtac cttttttttc accggaaagg    60
acccgtaaag tgataatgat tatcatctac atatcacaac gtgcgtggag gccatcaaac   120
cacgtcaaat aatcaattat gacgcaggta tcgtattaat tgatctgcat caacttaacg   180
taaaaacaac ttcagacaat acaaatcagc gacactgaat acgggcaac ctcatgtcaa    240 cgaagaacag aacccgcaga acaacaaccc gcaacatccg ctttcctaac caatgattg     300 aacaaattaa catcgctctt gagcaaaaag ggtccgggaa tttctcagcc tgggtcattg   360
aagcctgccg tcggagacta acgtcagaaa agagagcata tacatcaatt aaaagtgatg   420
aagaatgaac atcccgcgtt cttccctccg aacaggacga tattgtaaat tcacttaatt   480
acgagggcat tgcagtaatt gagttgcagt tttaccactt tcctgacagt gacagactgc   540
gtgttggctc tgtcacagac taaatagttt gaatgattag cagttatggt gatcagtcaa   600
ccaccaggga ataatccttc atattattat cgtgcttcac caacgctgcc tcaattgctc   660

```
tgaatgcttc cagagacacc ttatgttcta tacatgcaat tacaacatca gggtaactca    720
tagaaatggt gctattaagc atattttta cacgaatcag atccacggag ggatcatcag    780
cagattgttc tttattcatt tgtcgctcc atgcgcttgc tcttcatcta gcggttaaaa    840
tattacttca aatctttctg tatgaagatt tgagcacgtt ggccttacat acatctgtcg    900
gttgtatttc cctccagaat gccagcagga ccgcactttg ttacgcaacc aatactatta    960
agtgaaaaca ttcctaatat ttgacataaa tcatcaacaa aacacaagga ggtcagacca   1020
gattgaaacg ataaaaacga taatgcaaac tacgcgccct cgtatcacat ggaaggtttt   1080
accaatggct caggttgcca tttttaaaga aatattcgat caagtgcgaa aagatttaga   1140
ctgtgaattg ttttattctg aactaaaacg tcacaacgtc tcacattata tttactatct   1200
agccacagat aatattcaca tcgtgttaga aaacgataac accgtgttaa taaaaggact   1260 taaaaggtt gtaaatgtta aattctcaag aaacacgcat cttatagaaa cgtcctatga   1320
taggttgaaa tcaagagaaa tcacatttca gcaatacagg gaaatccttg ctaaagcagg   1380
agttttccga tgggttacaa atatccatga acataaaaga tattactata cctttgataa   1440
ttcattacta tttactgaga gcattcagaa cactacacaa atctttccac gctaaatcat   1500
aacgtccggt ttcttccgtg tcagcaccgg ggcgttggca taatgcaata cgtgtacgcg   1560
ctaaaccctg tgtgcatcgt tttaattatt cccggacact cccgcagaga agttccccgt   1620
cagggctgtg gacatagtta atccgggaat acaatgacga ttcatcgcac ctgacataca   1680
ttaataaata ttaacaatat gaaatttcaa ctcattgttt agggtttgtt taattttcta   1740
cacatacgat tctgcgaact tcaaaaagca tcgggaataa caccatgaaa aaaatgctac   1800
tcgctactgc gctggccctg cttattacag gatgtgctca acagacgttt actgttcaaa   1860
acaaaccggc agcagtagca ccaaaggaaa ccatcaccca tcatttcttc gtttctggaa   1920
ttgggcagaa gaaaactgtc gatgcagcca aaatttgtgg cggcgcagaa aatgttgtta   1980
aaacagaaac ccagcaaaca ttcgtaaatg gattgctcgg ttttattact ttaggcatt   2040 atactccgct ggaagcgcgt gtgtattgct cacaataatt gcatgagttg cccatcgata   2100
tgggcaactc tatctgcact gctcattaat atacttctgg gttccttcca gttgtttttg   2160
catagtgatc agcctctctc tgagggtgaa ataatcccgt tcagcggtgt ctgccagtcg   2220 ggggggaggct gcattatcca cgccggaggc ggtggtggct tcacgcactg actgacagac   2280
tgctttgatg tgcaaccgac gacgaccagc ggcaacatca tcacgcagag catcattttc   2340
agctttagca tcagctaact ccttcgtgta ttttgcatcg agcgcagcaa catcacgctg   2400
acgcatctgc atgtcagtaa ttgccgcgtt cgccagcttc agttctctgg cattttttgtc   2460 gcgctgggct ttgtaggtaa tggcgttatc acggtaatga ttaacagccc atgacaggca   2520
gacgatgatg cagataacca gagcggagat aatcgcggtg actctgctca tacatcaatc   2580
tctctgaccg ttccgcccgc ttctttgaat tttgcaatca ggctgtcagc cttatgctcg   2640
aactgaccat aaccagcgcc cggcagtgaa gcccagatat tgctgcaacg gtcgattgcc   2700
tgacggatat caccacgatc aatcataggt aaagcgccac gctccttaat ctgctgcaat   2760
gccacagcgt cctgactttt cggagagaag tctttcaggc caagctgctt gcggtaggca   2820
tcccaccaac gggaaagaag ctggtagcgt ccggcgcctg ttgatttgag ttttgggttt   2880
agcgtgacaa gtttgcgagg gtgatcggag taatcagtaa atagctctcc gcctacaatg   2940
acgtcataac catgatttct ggttttctga cgtccgttat cagttccctc cgaccacgcc   3000
agcatatcga ggaacgcctt acgttgatta ttgatttcta ccatcttcta ctccggcttt   3060
```

```
tttagcagcg aagcgtttga taagcgaacc aatcgagtca gtaccgatgt agccgataaa    3120
cacgctcgtt atataagcga gattgctact tagtccggcg aagtcgagaa ggtcacgaat    3180
gaactaggcg ataatggcgc acatcgttgc gtcgattact gttttgtaa acgcaccgcc     3240 attatatctg ccgcgaaggt acgccattgc aaacgcaagg attgcccga tgccttgttc     3300 ctttgccgcg agaatggcgg ccaacaggtc atgtttttct ggcatcttca tgtcttaccc    3360
ccaataaggg gatttgctct atttaattag gaataaggtc gattactgat agaacaaatc    3420
caggctactg tgtttagtaa tcagatttgt tcgtgaccga tatgcacggg caaaacggca    3480
ggaggttgtt agcgcaaaaa aaaaattcca aaaaaaaat tccaaaaaaa aaaagcgact    3540
aacaaacaca atctgatggc                                                3560

<210> SEQ ID NO 48
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 48
gccatcagat tgtgtttgtt agtcgctttt tttttttgga attttttttt tggaattttt     60
tttttgcgct aacaacctcc tgccg                                          85

<210> SEQ ID NO 49
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 49
gccatcagat tgtgtttgtt agtcgctttt tttttttgga attttttttt tggaattttt     60
tttttgcgct aacaacctcc tgccg                                          85
```

UNITED STATES PATENT AND TRADEMARK OFFICE
CERTIFICATE OF CORRECTION

| | | |
|---|---|---|
| PATENT NO. | : 10,669,578 B2 | Page 1 of 1 |
| APPLICATION NO. | : 15/120186 | |
| DATED | : June 2, 2020 | |
| INVENTOR(S) | : James Anthony Clarke et al. | |

It is certified that error appears in the above-identified patent and that said Letters Patent is hereby corrected as shown below:

On the Title Page

Item (72):
"Inventors: James Anthony Clarke, Kidlington (GB); Marion Louise Crawford, Oxford (GB); James White, Oxford (GB)"
Should read:
-- Inventors: James Anthony Clarke, Oxford (GB); Marion Louise Crawford, Oxford (GB); James White, Oxford (GB) --

Signed and Sealed this
Fourteenth Day of July, 2020

Andrei Iancu
*Director of the United States Patent and Trademark Office*